(12) United States Patent
Tomashek et al.

(10) Patent No.: US 8,263,379 B2
(45) Date of Patent: Sep. 11, 2012

(54) MODIFIED FAMILY 6 GLYCOSIDASES WITH ALTERED SUBSTRATE SPECIFICITY

(75) Inventors: John Tomashek, Ontario (CA); James Lavigne, Ontario (CA); Annie Tremblay, Ontario (CA); Patrick St-Pierre, Ontario (CA)

(73) Assignee: Iogen Energy Corporation, Ontario (CA)

( * ) Notice: Subject to any disclaimer, the term of this patent is extended or adjusted under 35 U.S.C. 154(b) by 402 days.

(21) Appl. No.: 12/504,070

(22) Filed: Jul. 16, 2009

(65) Prior Publication Data

US 2010/0016570 A1    Jan. 21, 2010

Related U.S. Application Data

(60) Provisional application No. 61/081,079, filed on Jul. 16, 2008.

(51) Int. Cl.
| | |
|---|---|
| C12N 9/24 | (2006.01) |
| C12N 1/00 | (2006.01) |
| C12P 21/06 | (2006.01) |
| C12P 7/06 | (2006.01) |
| C07H 21/04 | (2006.01) |
| C07H 1/00 | (2006.01) |
| C07K 1/00 | (2006.01) |
| C12C 11/00 | (2006.01) |
| A21D 2/00 | (2006.01) |
| A23B 7/00 | (2006.01) |

(52) U.S. Cl. ............... 435/200; 435/254.11; 435/254.1; 435/254.6; 435/69.1; 435/161; 536/23.2; 536/123.1; 530/350; 426/11; 426/20; 426/54

(58) Field of Classification Search ............... 435/200, 435/254.11, 254.22, 254.1, 254.6, 69.1, 161; 536/23.2, 123.1; 530/350; 426/11, 20, 54
See application file for complete search history.

(56) References Cited

U.S. PATENT DOCUMENTS

2009/0186381 A1    7/2009    Lavigne et al.

FOREIGN PATENT DOCUMENTS

| CA | 2477175 | 8/2003 |
| WO | 2004/056981 | 7/2004 |
| WO | 2008/025164 | 3/2008 |
| WO | 2008/095033 | 8/2008 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Chica et al., Semi-rational approaches to engineering enzyme activity: combining the benefits of directed evolution and rational design. Curr. Opi. Biotechnol., 2005, vol. 16: 378-384.*
Guo et al., Protein tolerance to random amino acid change. PNAS., 2004, vol. 101 (25): 9205-9210.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Sen et al., Developments in directed evolution for improving enzyme functions. Appl. Biochem. Biotechnol., 2007, vol. 143: 212-223.*
Andrews et al., "Substrate Specificity in Glycoside Hydrolase Family 10", J. Biolog. Chem., vol. 275, No. 30 (2000) 23027-33.
Bauer et al., "β-1,4-glucan-cellobiohydrolase [*Emericella nidulans*]", GenBank Acc. No. ABF50873 (2006).
Birren et al., "hypothetical protein SS1G_00892 [*Sclerotinia sclerotiorum* 1980]", GenBank Acc. No. EDN91489 (2007).
Birren et al., "hypothetical protein SNOG_06409 [*Phaeosphaeria nodorum* SN15]", GenBank Acc. No. EAT86240 (2006).
Coutinho et al., "Carbohydrate-active Enzymes: an Integrated Database Approach", Recent Advances in Carbohydrate Bioengineering—The Royal Society of Chemistry (1999) 3-12.
Davies, et al., "Structure and function of Humicola insolens family 6 cellulases: structure of the endoglucanase, Cel6B, at 1.6 Å Resolution", Biochem. J., vol. 348 (2000) 201-7.
Enari, et al. "Glucanolytic brewer's yeast", Proc. 21st. Congr. Euro. Brew. Conv.(1987) 529-36.
Henricksson, et al, "Hydrolysis of barley (1→3), (1→4)-β-D-glucan by a cellobiohydrolase II preparation from *Trichoderma reesei*", Carbohydrate Polymers, vol. 26 (1995) 109-19.
Koivula et al., "The active site of *Trichoderma reesei* cellobiohydrolase II: the role of tyrosine 169", Protein Eng., vol. 9, No. 8 (1996) 691-99.
Koivula et al., "Tryptophan 272: an essential determinant of crystalline cellulose degradation by *Trichoderma reesei* cellobiohydrolase Cel6A", FEBS Lett., vol. 429 (1998) 341-46.

(Continued)

*Primary Examiner* — Ganapathirama Raghu
(74) *Attorney, Agent, or Firm* — Fitzpatrick, Cella, Harper & Scinto

(57) ABSTRACT

A modified Family 6 glycosidase enzyme comprising amino acid substitutions at one or more positions selected from the group 182, 367, 399, 400 and 427 is provided (the position determined form alignment of a parental Family 6 glycosidase with SEQ ID NO: 1). Genetic constructs and genetically modified microbes comprising nucleic sequences encoding the modified Family 6 glycosidase are also provided. Family 6 glycosidase of the invention display decreased hydrolysis activity of beta 1-4 linked polysaccharides and increased hydrolysis activity of beta 1-3, 1-4 linked polysaccharides compared with a parental Family 6 glycosidase. Such glycosidases find use in a variety of applications in industry, e.g., in hydrolysis of beta 1-3, 1-4 linked polysaccharides during the processing of cereal grains or the production of alcohol, animal feed or food products.

18 Claims, 20 Drawing Sheets

OTHER PUBLICATIONS

Koivula et al., "The Active Site of Cellobiohydrolase Cel6A from *Trichoderma reesei*: The Roles of Aspartic Acids D221 and D175", J. Am. Chem. Soc., vol. 124 (2002) 10015-24.

Meinke et al., "Enhancement of the Endo-β-1,4-glucanase Activity of an Exocellobiohydrolase by Deletion of a Surface Loop", J. Biol. Chem., vol. 270, No. 9 (1995) 4383-86.

Rouvinen et al., "Three-Dimensional Structure of Cellobiohydrolyase II from *Trichoderma reesei*", Science, vol. 249 (1990) 380-86.

Spezio et al., "Crystal Structure of the Catalytic Domain of a Thermophilic Endocellulase", Biochem., vol. 32, No. 38 (1993) 9906-16.

Tao et al., "Milestones in directed enzyme evolution", Curr. Opin. Chem. Biol., vol. 6 (2002) 858-64.

Varrot et al., "Crystal structure of the catalytic core domain of the family 6 cellobiohydrolase II, Cel6A, from *Humicola insolens*, at 1.92 Å resolution", Biochem. J., vol. 337 (1999) 297-304.

Varrot et al., "Structure of the *Humicola insolens* cellobiohydrolase Cel6A D416A mutant in complex with a non-hydrolysable substrate analogue, methyl cellobiosyl-4-thio-β-cellobioside, at 1/9 Å", Acta. Crystallogr., vol. 58 (2002) 2201-04.

Varrot et al., "*Mycobacterium tuberculosis* Strains Posses Functional Cellulases", J. Biol. Chem., vol. 280, No. 21 (2005) 20181-184.

Wohlfahrt et al, "Probing pH-Dependent Functional Elements in Proteins: Modification of Carboxylic Acid Pairs in *Trichoderma reesei* Cellobiohydrolase Cel6A", Biochem., vol. 42, No. 34 (2003) 10095-103.

Zhang, Š. et al., "Site-directed mutation of noncatalytic residues of *Thermobifida fusca* exocellulase Cel6B", Euro. Journ. Of Biochem., vol. 267 (2000) 3101-15.

Zhang et al., "Effects of noncatalytic residue mutations on substrate specificity and ligand binding of *Thermobifida fusca* endocellulase Cel6A" Euro. Journ. of Biochem., vol. 267 (2000) 244-52.

Zou et al., "Crystallographic evidence for substrate ring distortion and protein conformational changes during catalysis in cellobiohydrolase Cel6A from *Trichoderma reesei*", Structure, vol. 7, No. 9 (1999) 1035-45.

Erratum (re Rouvinen et al., "Res. Art. Three-dimensional structure of cellobiohydrolase II from *Trichoderma ressei*") in: Science vol. 249 (1990) 1359.

* cited by examiner

```
SEQ ID NO: 1   83 SGTATYSGNPFVG--------VTPWANAYYASEVSSLAIP 114
SEQ ID NO: 2      ---ATYSGNPFVG--------VTPWANAYYASEVSSLAIP
SEQ ID NO: 3      ---ATYSGNPFVG--------VTPWANAYYASEVSSLAIP
SEQ ID NO: 4      ---ATYSGNPFVG--------VTPWANAYYASEVSSLAIP
SEQ ID NO: 5      ---ATYSGNPFVG--------VTPWANAYYASEVSSLAIP
SEQ ID NO: 6      ---ATYSGNPFVG--------VTPWANAYYASEVSSLAIP
SEQ ID NO: 7      ---ATASGNPFSG--------YQLYVNPYYSSEVQSIAIP
SEQ ID NO: 8      ---ASASGNPFSG--------YQLYVNPYYSSEVASLAIP
SEQ ID NO: 9      ---ATAGGNPFEG--------YDLYVNPYYKSEVESLAIP
SEQ ID NO: 10     ---ASATGNPFEG--------YQLYANPYYKSQVESSAIP
SEQ ID NO: 11     ---AAASGNPFSG--------YQLYANPYYSSEVHTLAIP
SEQ ID NO: 12     ---ASASGNPFEG--------YQLYANPYYASEVISLAIP
SEQ ID NO: 13     ---PVATNNPFSG--------VDLWANNYYRSEVSTLAIP
SEQ ID NO: 14     ---PAASDNPYAG--------VDLWANNYYRSEVMNLAVP
SEQ ID NO: 15     ---ASFTGNPFLG--------VQGWANSYYSSEIYNHAIP
SEQ ID NO: 16     ---VQATGNPFEG--------YQLYANPYYSSEVMTLAVP
SEQ ID NO: 17     ---ASATGNPFEG--------YQLYVNPYYKSQVESSAIP
SEQ ID NO: 18     ---ASFTGNPFAG--------VNLFPNKFYSSEVHTLAIP
SEQ ID NO: 19     ---ASYNGNPFSG--------VQLWANTYYSSEVHTLAIP
SEQ ID NO: 20     ---ASYNGNPFSG--------VQLWANTYYSSEVHTLAIP
SEQ ID NO: 21     ---ATYTGNPFLG--------VNQWANNFYRSEIMNIAVP
SEQ ID NO: 22     ---ASYNGNPFEG--------VQLWANNYYRSEVHTLAIP
SEQ ID NO: 23     -------GNPFEG--------VQLWANNYYRSEVHTLAIP
SEQ ID NO: 24     ---AAPSGNPFAG--------KNFYANPYYSSEVHTLAMP
SEQ ID NO: 25     ------AGNPYTG--------KTVWLSPFYADEVAQAAAD
SEQ ID NO: 26     ---TPAAGNPFVG--------VTPFLSPYYAAEVAAAADA
SEQ ID NO: 27     ---TPAAGNPFTG--------YEIYLSPYYANEIAAAVTQ
SEQ ID NO: 28     ---TPAAGNPFT---------EQIYLSPYYANEIAAAVTQ
SEQ ID NO: 29     ---QANSSNPFAG--------HTIYPNPYYSNEIDEFAIP
SEQ ID NO: 30     ---PPSANNPWTG--------FQIFLSPYYANEVAAAAKQ
SEQ ID NO: 31     ---VPAAGNPYTG--------YEIYLSPYYAAEAQAAAAQ
SEQ ID NO: 32     ---LDASTNVFQQ--------YTLHPNNFYRAEVEAAAEA
SEQ ID NO: 33     ---TPDAGNPYIGYDVSHVLWCQIYLSPYYADEVAAAVSA
SEQ ID NO: 34     ---TPAAGNPFTG--------FQVYLSPYYSAEIASAAAA
SEQ ID NO: 35     ---LDASTNVWKK--------YTLHANKFYRTEVEAAVAA
SEQ ID NO: 36     ---LDASTNVFSK--------YTLHPNSFYRAEVEAAAEA
```

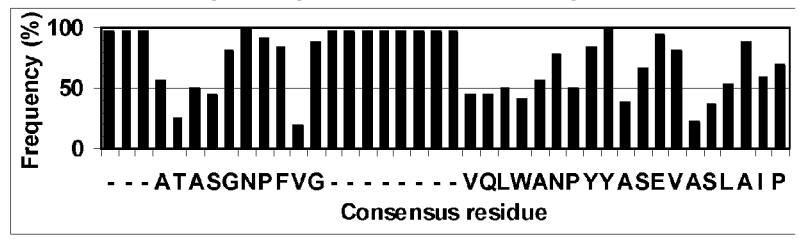

Figure 1

```
SEQ ID NO: 1    115  SLTG---AMATAAAAVAK*VPSFMWLDTLDKTP-LMEQTLA  150
SEQ ID NO: 2         SLTG---AMATAAAAVAKVPSFMWLDTLDKTP-LMEQTLA
SEQ ID NO: 3         SLTG---AMATAAAAVAKVPSFMWLDTLDKTP-LMEQTLA
SEQ ID NO: 4         SLTG---AMATAAAAVAKVPSFMWLDTFDKTP-LMEQTLA
SEQ ID NO: 5         SLTG---AMATAAAAVAKVPSSMWLDTFDKTP-LMEQTLA
SEQ ID NO: 6         SLTG---AMATAAAAVAKVPSFMWLDTLDKTP-LMEQTLA
SEQ ID NO: 7         SLTGTLSSLAPAATAAAKVPSFVWLDVAAKVP-TMATYLA
SEQ ID NO: 8         SLTGSLSSLQAAATAAAKVPSFVWLDTAAKVP-TMGDYLA
SEQ ID NO: 9         SMTG---SLAEKASAAANVPSFHWLDTTDKVP-QMGEFLE
SEQ ID NO: 10        SLSAS--SLVAQASAAADVPSFYWLDTADKVP-TMGEYLE
SEQ ID NO: 11        SLTG---SLAAAATKAAEIPSFVWLDTAAKVP-TMGTYLA
SEQ ID NO: 12        SLSS---ELVPKASEVAKVPSFVWLDQAAKVP-SMGDYLK
SEQ ID NO: 13        KLS---GAMATAAAKVADVPSFQWMDT-YDHISFMEDSLA
SEQ ID NO: 14        KLS---GAKATAAAKVADVPSFQWMDT-YDHISLMEDTLA
SEQ ID NO: 15        SMT---GSLAAQASAVAKVPTFQWLDRNVTVDTLMKSTLE
SEQ ID NO: 16        SMTG---SLAEQATHAAEIPSFHWLDTTAKVP-TMGEYLA
SEQ ID NO: 17        SLSAS--SLVAQASAAADVPSFYWLDTADKVP-TMGEYLD
SEQ ID NO: 18        SLTG---SLVAKASAVAQVPSFQWLDIAAKVETLMPGALA
SEQ ID NO: 19        SLS---PELAAKAAKVAEVPSFQWLDRNVTVDTLFSGTLA
SEQ ID NO: 20        SLS---PELAAKAAKVAEVPSFQWLDRNVTVDTLFSGTLA
SEQ ID NO: 21        SLS---GAMATAAAKVADVPTFQWIDK-MDKLPLIDEALA
SEQ ID NO: 22        QITD--PALRAAASAVAEVPSFQWLDRNVTVDTLLVETLS
SEQ ID NO: 23        QITD--PALRAAASAVAEVPSFQWLDRNVTVDTLLVQTLS
SEQ ID NO: 24        SLPA---SLKPAATAVAKVGSFVWMDTMAKVP-LMDTYLA
SEQ ID NO: 25        ISNP---SLATKAASVAKIPTFVWFDTVAKVP-DLGGYLA
SEQ ID NO: 26        ITDS---TLKAKAASVAKIPTFTWLDSVAKVP-DLGTYLA
SEQ ID NO: 27        ISDP---TTAAAAAKVANIPTFIWLDQVAKVP-DLGTYLA
SEQ ID NO: 28        ISDP---TTAAAAAKVANIPTFIWLDQVAKVP-DLGTYLA
SEQ ID NO: 29        ALQETDPALVEKAALVKEVGTFFWIDVVAKVP-DIGPYLQ
SEQ ID NO: 30        ITDP---TLSSKAASVANIPTFTWLDSVAKIP-DLGTYLA
SEQ ID NO: 31        ISDA---TQKAKALKVAQIPTFTWFDVIAKTS-TLGDYLA
SEQ ID NO: 32        ISDS---ALAEKARKVADVGTFLWLDTIENIG-RLEPALE
SEQ ID NO: 33        ISNP---ALAAKAASVANIPTFIWFDVVAKVP-TLGTYLA
SEQ ID NO: 34        VTDS---SLKAKAASVANIPTFTWLDSVAKVP-DLGTYLA
SEQ ID NO: 35        ISDS---SLAAKAAKVANVGSFLWLDSIENIG-KLEPALE
SEQ ID NO: 36        ISDS---TLKAQALKVADVGSFLWIDTISAIS-RIEPGVS
```

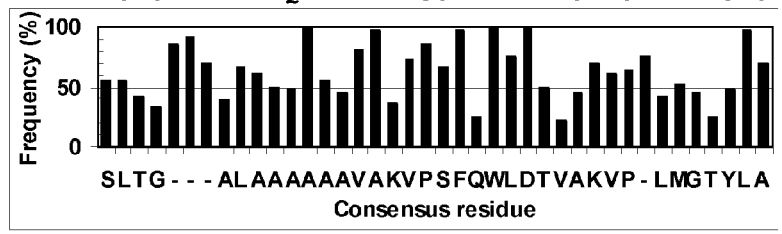

Figure 1 (Cont'd)

```
SEQ ID NO: 1    151 DIRTANKNGGN--YAGQFVVYDLPDRDCAALASNGEYSIA 188
SEQ ID NO: 2        DIRTANKNGGN--YAGQFVVYDLPDRDCAALASNGEYSIA
SEQ ID NO: 3        DIRTANKNGGN--YAGQFVVYDLPDRDCAALASNGEYSIA
SEQ ID NO: 4        DIRTANKNGGN--YAGQFVVYDLPDRDCAALASNGEYSIA
SEQ ID NO: 5        DIRTANKNGGN--YAGQFVVYDLPDRDCAALASNGEYSIA
SEQ ID NO: 6        DIRTANKNGGN--YAGQFVVYDLPDRDCAALASNGEYSIA
SEQ ID NO: 7        DIRSQNAAGANPPIAGQFVVYDLPDRDCAALASNGEFAIS
SEQ ID NO: 8        DIQSQNAAGANPPIAGQFVVYDLPDRDCAALASNGEYSIA
SEQ ID NO: 9        DIKTKNAAGANPPTAGIFVVYDLPDRDCAALASNGEFLIS
SEQ ID NO: 10       DIQTQNAAGASPPIAGIFVVYDLPDRDCSALASNGEYSIS
SEQ ID NO: 11       NIEAANKAGASPPIAGIFVVYDLPDRDCAAAASNGEYTVA
SEQ ID NO: 12       DIQSQNAAGADPPIAGIFVVYDLPDRDCAAAASNGEFSIA
SEQ ID NO: 13       DIRKANKAGGN--YAGQFVVYDLPDRDCAAAASNGEYSLD
SEQ ID NO: 14       DIRKANKAGGK--YAGQFVVYDLPNRDCAAAASNGEYSLD
SEQ ID NO: 15       EIRAANKAGANPPYAAHFVVYDLPDRDCAAAASNGEFSIA
SEQ ID NO: 16       DIKEQNDAGANPPIAGIFVVYNLPDRDCAALASNGELSIA
SEQ ID NO: 17       DIQTQNAAGANPPIAGIFVVYDLPDRDCAALASNGEYAIS
SEQ ID NO: 18       DVRAANAAGGN--YAAQLVVYDLPDRDCAAAASNGEFSIA
SEQ ID NO: 19       EIRAANQRGANPPYAGIFVVYDLPDRDCAAAASNGEWSIA
SEQ ID NO: 20       EIRAANQRGANPPYAGIFVVYDLPDRDCAAAASNGEWSIA
SEQ ID NO: 21       DVRAANARGGN--YASILVVYNLPDRDCAAAASNGEFAIA
SEQ ID NO: 22       EIRAANQAGANPPYAAQIVVYDLPDRDCAAAASNGEWAIA
SEQ ID NO: 23       EIREANQAGANPQYAAQIVVYDLPDRDCAAAASNGEWAIA
SEQ ID NO: 24       DIKAKNAAGAN--LMGTFVVYDLPDRDCAALASNGELKID
SEQ ID NO: 25       DAR------SKN-QLVQIVVYDLPDRDCAALASNGEFSLA
SEQ ID NO: 26       DASALQKSSGQP-QVVQIVVYDLPDRDCAAKASNGEFSIA
SEQ ID NO: 27       DASAKQKSEGKN-YLVQIVVYDLPDRDCAALASNGEFTIA
SEQ ID NO: 28       DASAKQKSEGKN-YLVQIVVYDLPDRDCAALASNGEFTIA
SEQ ID NO: 29       GIQEANAAGQNPPYIGAIVVYDLPNRDCAAAASNGEFSLE
SEQ ID NO: 30       SASALGKSTGTK-QLVQIVIYDLPDRDCAAKASNGEFSIA
SEQ ID NO: 31       EASALGKSSGKK-YLVQIVVYDLPDRDCAALASNGEFSIA
SEQ ID NO: 32       DVPCENIVG-------LVIYDLPGRDCAAKASNGELKVG
SEQ ID NO: 33       DALSIQQSTGRN-QLVQIVVYDLPDRDCAALASNGEFSIA
SEQ ID NO: 34       DASSIQTKTGQK-QLVPIVVYELPDRDCAAKASNGEFSIA
SEQ ID NO: 35       DVPCDHILG-------LVIYDLPGRDCAAKASNGELAVG
SEQ ID NO: 36       DQPCDHILG-------LVIYDLPGRDCAAKASNGELKVG
```

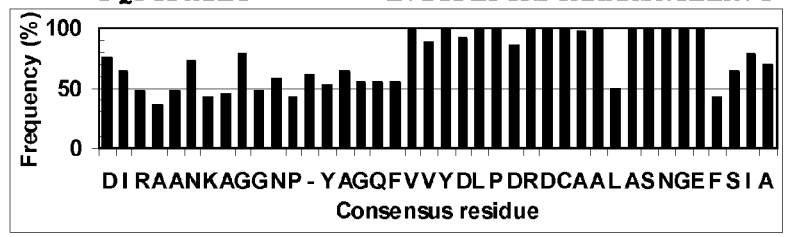

Figure 1 (Cont'd)

```
SEQ ID NO: 1    189 DGGVAKYK-NYIDTIRQIVV-----------------EY 209
SEQ ID NO: 2        DGGVAKYK-NYIDTIRQIVV-----------------EY
SEQ ID NO: 3        DGGVAKYK-NYIDTIRQIVV-----------------EY
SEQ ID NO: 4        DGGVDKYK-NYIDTIRQIVV-----------------EY
SEQ ID NO: 5        DGGVDKYK-NYIDTIRQIVV-----------------EY
SEQ ID NO: 6        DGGVAKYK-NYIDTIRQIVV-----------------EY
SEQ ID NO: 7        DGGVQHYK-DYIDSIREILV-----------------EY
SEQ ID NO: 8        DNGVEHYK-SYIDSIREILV-----------------QY
SEQ ID NO: 9        DGGVEKYK-AYIDSIREQVE-----------------KY
SEQ ID NO: 10       DGGVEKYK-AYIDSIREQVE-----------------TY
SEQ ID NO: 11       NNGVANYK-AYIDSIVAQLK-----------------AY
SEQ ID NO: 12       NNGVALYK-QYIDSIREQLT-----------------TY
SEQ ID NO: 13       KDGKNKYK-AYIAD-QGILQ-----------------DY
SEQ ID NO: 14       KDGANKYK-AYIAKIKGILQ-----------------NY
SEQ ID NO: 15       NGGVANYK-TYINAIRKLLI-----------------EY
SEQ ID NO: 16       DGGVEKYK-EYIDAIRAHAV-----------------EY
SEQ ID NO: 17       DGGVEKYK-AYIDSIREQVE-----------------TY
SEQ ID NO: 18       DGGVVKYK-AYIDAIRKQLL-----------------AY
SEQ ID NO: 19       NNGANNYK-RYIDRIRELLI-----------------QY
SEQ ID NO: 20       NNGANNLQ-RYIDRIRELLI-----------------QY
SEQ ID NO: 21       DGGVAKYK-NYIDEIRKLVI-----------------KY
SEQ ID NO: 22       NNGANNYK-GYINRIREILI-----------------SF
SEQ ID NO: 23       NNGVNNYK-AYINRIREILI-----------------SF
SEQ ID NO: 24       EGGVEKYKTQYIDKIAAIIK-----------------KY
SEQ ID NO: 25       NDGLNKYK-NYVDQIAAQIK-----------------QF
SEQ ID NO: 26       DGGQAKYY-DYIDQIVAQIK-----------------KF
SEQ ID NO: 27       DNGEANYH-DYIDQIVAQIK-----------------QY
SEQ ID NO: 28       DNGEANYH-DYIDQIVAQIK-----------------QY
SEQ ID NO: 29       DGGEEKYR-GYIDGIREQIE-----------------KY
SEQ ID NO: 30       NNGQANYE-NYIDQIVAQIQ-----------------QF
SEQ ID NO: 31       NNGLNNYK-GYIDQLVAQIK-----------------KY
SEQ ID NO: 32       --ELDRYKTEYIDKIAEILK-----------------AH
SEQ ID NO: 33       NNGLANYK-NYVDQIVAQIARTCCPLVTSAITDLACLSEY
SEQ ID NO: 34       DAGAENYK-DYIDQIVPQIK-----------------QF
SEQ ID NO: 35       --ELSRYKTEYIDAIVKILK-----------------AH
SEQ ID NO: 36       --ELAKYKSQYIDPIAALLK-----------------KY
```

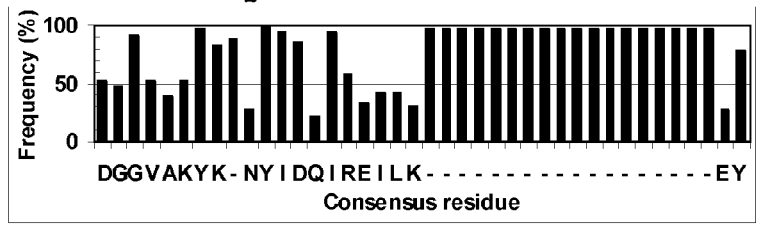

Figure 1 (Cont'd)

```
SEQ ID NO: 1   210 SDIRTLLVIEPDSLANLVTNLGTPKCANAQSAYLECINYA 249
SEQ ID NO: 2       SDIRTLLVIEPDSLANLVTNLGTPKCANAQSAYLECINYA
SEQ ID NO: 3       SDIRTLLVIEPDSLANLVTNLGTPKCANAPSAYLECINYA
SEQ ID NO: 4       SDIRTLLVIEPDSLANLVTNLGTPKCANAQSAYLECINYA
SEQ ID NO: 5       SDIRTLLVIEPDSLANLVTNLGTPKCANAQSAYLECINYA
SEQ ID NO: 6       SDIRTILVIEPDSLANLVTNLGTPKCANAQSAYLECINYA
SEQ ID NO: 7       SDVHVILVIEPDSLANLVTNLNVAKCANAQSAYLECTNYA
SEQ ID NO: 8       SDVHTLLVIEPDSLANLVTNLNVAKCANAESAYLECTNYA
SEQ ID NO: 9       SDTQIILVIEPDSLANLVTNLNVQKCANAQDAYLECTNYA
SEQ ID NO: 10      SDVQTILIIEPDSLANLVTNLDVAKCANAESAYLECTNYA
SEQ ID NO: 11      PDVHTILIIEPDSLANMVTNLSTAKCAEAQSAYYECVNYA
SEQ ID NO: 12      SDVHTILVIEPDSLANVVTNLNVPKCANAQDAYLECINYA
SEQ ID NO: 13      SDTRIILVIEPDSLANMVTNMNVPKCANAASAYKELTIHA
SEQ ID NO: 14      SDTKVILVIEPDSLANLVTNLNVDKCAKAESAYKELTVYA
SEQ ID NO: 15      SDIRTILVIEPDSLANLVTNTNVAKCANAASAYRECTNYA
SEQ ID NO: 16      SDTNIILIIEPDSLANLVTNLNVEKCANAQDAYLECTNYA
SEQ ID NO: 17      SDVQTILIIEPDSLANLVTNLDVAKCANAQSAYLECTNYA
SEQ ID NO: 18      SDVRTILVIEPDSLANMVTNMGVPKCAGAKDAYLECTIYA
SEQ ID NO: 19      SDIRTILVIEPDSLANMVTNMNVQKCSNAASTYKELTVYA
SEQ ID NO: 20      SDIRTILVIEPDSLANMVTNMNVQKCSNAASTYKELTVYA
SEQ ID NO: 21      NDLRIILVIEPDSLANMVTNMNVAKCQNAASAYRECTNYA
SEQ ID NO: 22      SDVRTILVIEPDSLANMVTNMNVAKCSGAASTYRELTIYA
SEQ ID NO: 23      SDVRTILVIEPDSLANMVTNMNVPKCSGAASTYRELTIYA
SEQ ID NO: 24      PDVKINLAIEPDSLANMVTNMGVQKCSRAAPYYKELTAYA
SEQ ID NO: 25      PDVSVVAVIEPDSLANLVTNLNVQKCANAQSAYKEGVIYA
SEQ ID NO: 26      PDVRVIAVIEPDSLANLVTNLNVQKCANAQTTYKACVTYA
SEQ ID NO: 27      PDVHVVAVIEPDSLANLVTNLSVAKCANAQTTYLECVTYA
SEQ ID NO: 28      PDVHVVAVIEPDSLANLVTNLSVAKCANAQTTYLECVTYA
SEQ ID NO: 29      PDVRVALVIEPDSLANMVTNLNVPKCAESEQAYRDGVAYA
SEQ ID NO: 30      PDVRVVAVIEPDSLANLVTNLNVQKCANAKTTYLACVNYA
SEQ ID NO: 31      PDVRVVAVIEPDSLANLVTNLNVSKCANAQTAYKAGVTYA
SEQ ID NO: 32      SNTAFALVIEPDSLPNLVTNSDLQTCQQSASGYREGVAYA
SEQ ID NO: 33      PQIRVVAVVEPDSLANMVTNLNVPKCAGAQAAYTEGVTYA
SEQ ID NO: 34      PDVRVVAVIEPDSLANLVTNLNVQKCANGG-TYKASVTYA
SEQ ID NO: 35      PKTAFALVIEPDSLPNLVTNSDLQTCKDSASGYRDGVAYA
SEQ ID NO: 36      NNHAFALLIEPDSLPNLVTNSDLSACQQSAAGYRDGVAYA
```

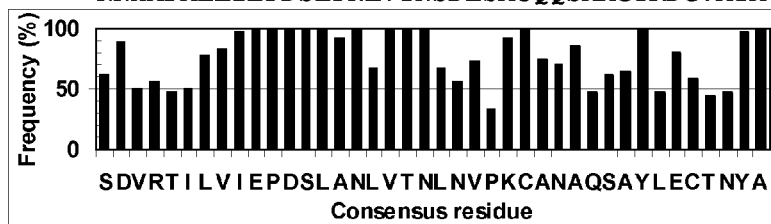

Figure 1 (Cont'd)

```
SEQ ID NO: 1    250 VTQLNLPNVAMYLDAGHAGWLGWPANQDPAAQLFANVYKN 289
SEQ ID NO: 2        VTQLNLPNVAMYLDAGHAGWLGWPANQDPAAQLFANVYKN
SEQ ID NO: 3        VTQLNLPNVAMYLDAGHAGWLGWPANQDPAAQLFANVYKN
SEQ ID NO: 4        VTQLNLPNVAMYLDAGHAGWLGWPANQDPAAQLFANVYKN
SEQ ID NO: 5        VTQLNLPNVAMYLDAGHAGWLGWPANQDPAAQLFANVYKN
SEQ ID NO: 6        ITQLNLPNIAMYLDAGHAGWLGWPANQDPAAQLFANVYKN
SEQ ID NO: 7        VTQLNLPNVAMYLDAGHAGWLGWPANLQPAANLYAGVYSD
SEQ ID NO: 8        LTQLNLPNVAMYLDAGHAGWLGWPANQQPAADLFASVYKN
SEQ ID NO: 9        LTQLNLPNVAMYLDAGHAGWLGWPANIGPAAELYASVYKN
SEQ ID NO: 10       LEQLNLPNVAMYLDAGHAGWLGWPANIGPAAQLYASVYKN
SEQ ID NO: 11       LINLNLANVAMYIDAGHAGWLGWSANLSPAAQLFATVYKN
SEQ ID NO: 12       ITQLDLPNVAMYLDAGHAGWLGWQANLAPAAQLFASVYKN
SEQ ID NO: 13       LKELNLPNVSMYIDAGHGGWLGWPANLPPAAQLYGQLYKD
SEQ ID NO: 14       IKELNLPNVSMYLDAGHGGWLGWPANIGPAAKLYAQIYKD
SEQ ID NO: 15       ITQLDLPHVAQYLDAGHGGWLGWPANIQPAATLFADIYKA
SEQ ID NO: 16       ITQLDLPNVSMYLDAGHAGWLGWPANIGPAAQLFAGVYQD
SEQ ID NO: 17       LEQLNLPNVAMYLDAGHAGWLGWPANIGPAAELYASVYKN
SEQ ID NO: 18       VKQLNLPHVAMYLDGGHAGWLGWPANLQPAADLFGKLYAD
SEQ ID NO: 19       LKQLNLPHVAMYMDAGHAGWLGWPANIQPAAELFAQIYRD
SEQ ID NO: 20       LKQLNLPHVAMYMDAGHAGWLGWPANIQPAAELFAQIYRD
SEQ ID NO: 21       LTNLDLPNVAQYMDAGHAGWLGWPANITPAAQLFAEVYKQ
SEQ ID NO: 22       LKQLDLPHVAMYMDAGHAGWLGWPANIQPAAELFAKIYED
SEQ ID NO: 23       LKQLDLPHVAMYMDAGHAGWLGWPANIQPAAELFAKIYED
SEQ ID NO: 24       LKTLNFNNVDMYMDGGHAGWLGWDANIGPTAKLFAEVYKA
SEQ ID NO: 25       VQKLNAVGVTMYIDAGHAGWLGWPANLSPAAQLFAQIYRD
SEQ ID NO: 26       LNQLASVGVYQYMDAGHAGWLGWPANIQPAAQLFADMFKS
SEQ ID NO: 27       MQQLSAVGVTMYLDAGHAGWLGWPANLSPAAQLFTSLYSN
SEQ ID NO: 28       MQQLSAVGVTMYLDAGHAGWLGWPANLSPAAQLFTSLYSN
SEQ ID NO: 29       LKQLDLPNVWTYIDAGHSGWLGWPANIEPAAEIFVEVWNA
SEQ ID NO: 30       LTNLAKVGVYMYMDAGHAGWLGWPANLSPAAQLFTQVWQN
SEQ ID NO: 31       LQQLNSVGVYMYLDAGHAGWLGWPANLNPAAQLFSQLYRD
SEQ ID NO: 32       LKQLNLPNVVMYIDAGHGGWLGWDANLKPGAQELASVYKS
SEQ ID NO: 33       LQKLNTVGVYSYVDAGHAGWLGWPANLGPAAQLFANLYTN
SEQ ID NO: 34       LQQLSSVGVTMYMDAGHAGWLGWPANIQPGSEVFAEMFKS
SEQ ID NO: 35       LRNLNLPNVVMYIDAGHGGWLGWDANLKPGAQELAKAYKA
SEQ ID NO: 36       LKTLNLPNVVMYIDAGHGGWLGWNDNLKPGAEELAKAYKA
```

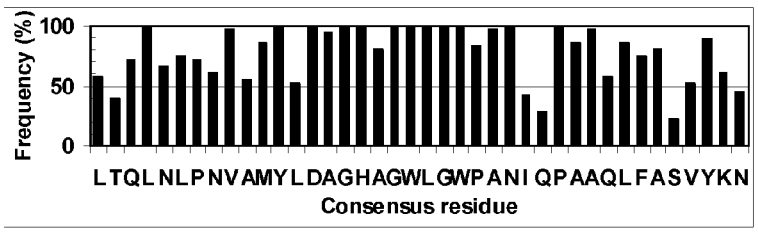

Figure 1 (Cont'd)

```
SEQ ID NO: 1   290 ASSPRALRGLATNVANYNGWNIT----SPPSYTQGNÅVYN 325
SEQ ID NO: 2       ASSPRALRGLATNVANYNGWNIT----SPPSYTQGNAVYN
SEQ ID NO: 3       ASSPRALRGLATNVANYNGWNIT----SPPSYTQGNAVYN
SEQ ID NO: 4       ASSPRALRGLATNVANYNGWNIT----SPPSYTQGNAVYN
SEQ ID NO: 5       ASSPRALRGLATNVANYNGWNIT----SPPSYTQGNAVYN
SEQ ID NO: 6       ASSPSALRGLATNVANYNGWNIT----SPPSYTQGNAVYN
SEQ ID NO: 7       AGSPAALRGLATNVANYNAWAID----TCPSYTQGNSVCD
SEQ ID NO: 8       ASSPAAVRGLATNVANYNAWTIS----SCPSYTQGNSVCD
SEQ ID NO: 9       ASSPAAVRGLATNVANYNAFSID----SCPSYTQGSTVCD
SEQ ID NO: 10      ASSPAAVRGLATNVANFNAWSID----SCPSYTSGNDVCD
SEQ ID NO: 11      ASAPASLRGLATNVANYNAWSIS----SPPSYTSGDSNYD
SEQ ID NO: 12      ASSPASVRGLATNVANYNAWSIS----RCPSYTQGDANCD
SEQ ID NO: 13      AGKPSRLRGLVTNVSNYNAWKLS----SKPDYTESNPNYD
SEQ ID NO: 14      AGKPSRVRGLVTNVSNYNGWKLS----TKPDYTESNPNYD
SEQ ID NO: 15      AGKPKSVRGLVTNVSNYNGWSLS----SAPSYTTPNPNYD
SEQ ID NO: 16      AGAPAALRGLATNVANYNAFSID----TCPSYTSQNAVCD
SEQ ID NO: 17      ASSPAAVRGLATBVANFNAWSID----TCPSYTSGNDVCD
SEQ ID NO: 18      AGKPSQLRGMATNVANYNAWDLT----TAPSYTTPNPNFD
SEQ ID NO: 19      AGRPAAVRGLATNVANYNAWSIA----SPPSYTSPNPNYD
SEQ ID NO: 20      AGRPAAVRGLATNVANYNAWSIA----SPPSYTSPNPNYD
SEQ ID NO: 21      AGSPKSVRGLAINVSNYNAWSVS----SPPPYTSPNPNYD
SEQ ID NO: 22      AGKPRAVRGLATNVANYNAWSIS----SPPPYTSPNPNYD
SEQ ID NO: 23      AGKPRAVRGLATNVANYNAWSVS----SPPPYTSPNPNYD
SEQ ID NO: 24      AGSPRGVRGIVTNVSNYNALRVS----SCPSITQGNKNCD
SEQ ID NO: 25      AGSPRNLRGIATNVANFNALRAS----SPDPITQGNSNYD
SEQ ID NO: 26      ANSSKFVRGLATNVANYNALSAA----SPDPITQGDPNYD
SEQ ID NO: 27      AGSPSGVRGLATNVANYNALVAT----TPDPITQGDPNYD
SEQ ID NO: 28      AGSPSGVRGLATNVANYNALVAT----TPDPITQGDPNYD
SEQ ID NO: 29      AGRPKSTRGFATNVSNYNGYSLS----TAPPYTEPNPNFD
SEQ ID NO: 30      AGKSPFIKGLATNVANYNALQAA----SPDPITQGNPNYD
SEQ ID NO: 31      AGSPQYVRGLATNVANYNALSAS----SPDPVTQGNPNYD
SEQ ID NO: 32      AGSPSQVRGISTNVAGWNAWDQEPGEFSDASDAQYNKCQN
SEQ ID NO: 33      AGSPSFFRGLATNVANYNLLNAP----SPDPVTSPNANYD
SEQ ID NO: 34      ADFVAFVRAFATNVREYNALTAA----FPRPITQGNPNYD
SEQ ID NO: 35      AGSPKQVRGIATNVAGWNQWDLTPGEFSKASDAKYNKCQN
SEQ ID NO: 36      AGSPKQFRGFATNVAGWNAWDLTPGEFSSASDAQWNKCQN
```

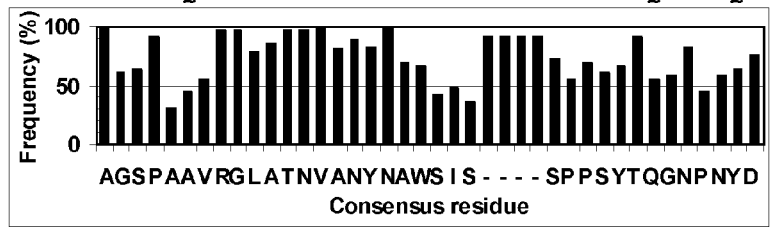

Figure 1 (Cont'd)

```
SEQ ID NO: 1   326 EKLYIH----------------AIGPLLANHGWSNAFFI 348
SEQ ID NO: 2       EKLYIH----------------AIGRLLANHGWSNAFFI
SEQ ID NO: 3       EKLYIH----------------AIGPLLANHGWSNAFFI
SEQ ID NO: 4       EQLYIH----------------AIGPLLANHGWSNAFFI
SEQ ID NO: 5       EQLYIH----------------AIGPLLANHGWSNAFFI
SEQ ID NO: 6       EKLYIH----------------AIGPLLANHGWSNAFFI
SEQ ID NO: 7       EKDYIN----------------ALAPLLRAQGFD-AHFI
SEQ ID NO: 8       EQQYIN----------------AIAPLLQAQGFD-AHFI
SEQ ID NO: 9       EKTYIN----------------NFAPQLKSAGFD-AHFI
SEQ ID NO: 10      EKSYIN----------------AIAPELSSAGFD-AHFI
SEQ ID NO: 11      EKLYIN----------------ALSPLLTSNGWPNAHFI
SEQ ID NO: 12      EEDYVN----------------ALGPLFQEQGFP-AYFI
SEQ ID NO: 13      EQKYIH----------------ALSPLLEQEGWPGAKFI
SEQ ID NO: 14      EQRYIN----------------AFAPLLAQEGWSNVKFI
SEQ ID NO: 15      EKKYIE----------------AFSPLLNAAGFP-AQFI
SEQ ID NO: 16      EKGYIN----------------SFAPELSAAGWD-AHFI
SEQ ID NO: 17      EKSYIN----------------AFAPELSXAGFD-AHFI
SEQ ID NO: 18      EKKYIS----------------AFAPLLAAKGWS-AHFI
SEQ ID NO: 19      EKHYIE----------------AFAPLLRNQGFD-AKFI
SEQ ID NO: 20      EKHYIE----------------AFAPLLRNQGFD-AKFI
SEQ ID NO: 21      ERHFVE----------------AFAPLLRQNGWD-AKFI
SEQ ID NO: 22      EKHYIE----------------AFRPLLEARGFP-AQFI
SEQ ID NO: 23      EKHYIE----------------AFRPLLEARGFP-AQFI
SEQ ID NO: 24      EERYIN----------------ALAPLLKNEGFP-AHFI
SEQ ID NO: 25      EIHYI-----------------EALAPMLSNAGFP-AHFI
SEQ ID NO: 26      ELHYIN----------------ALGPMLAQQGFP-AQFV
SEQ ID NO: 27      EMLYIE----------------ALAPLLGS--FP-AHFI
SEQ ID NO: 28      EMLYIE----------------ALAPLLGS--FP-AHFI
SEQ ID NO: 29      EVRYIN----------------AFRPLLEARGFP-AYFI
SEQ ID NO: 30      EIHYIN----------------ALAPLLQQAGWD-ATFI
SEQ ID NO: 31      ELHYIN----------------ALAPALQSGGFP-AHFI
SEQ ID NO: 32      EKIYIN----------------TFGAELKSAGMP-NHAI
SEQ ID NO: 33      EIHYINVSDCFVLIWTSLTICIIALAPELSSRGFP-AHFI
SEQ ID NO: 34      EFPYIQ----------------RVRPMLKSPGFP-AQFV
SEQ ID NO: 35      EKLYLD----------------NFGPALKSAGMP-NHAI
SEQ ID NO: 36      EKIYVE----------------TFGPLLKNAGMP-NHAI
```

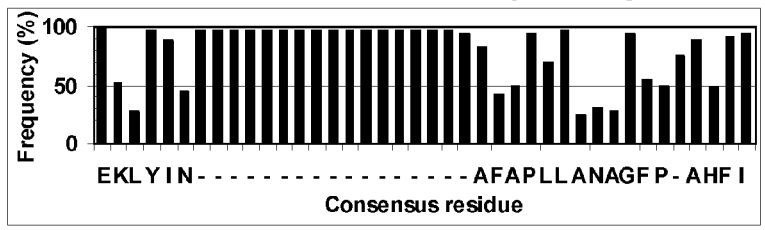

Figure 1 (Cont'd)

```
SEQ ID NO: 1    349  TDQGRSGKQPTGQQQWGDWCNVIGTGFGIRPSANTGDSLL  388
SEQ ID NO: 2         TDQGRSGKQPTGQQQWGDWCNVIGTGFGIRPSANTGDSLL
SEQ ID NO: 3         TDQGRSGKQPTGQQQWGDWCNVIGTGFGIRPSANTGDSLL
SEQ ID NO: 4         TDQGRSGKQPTGQQQWGDWCNVIGTGFGIRPSANTGDSLL
SEQ ID NO: 5         TDQGRSGKQPTGQQQWGDWCNVIGTGFGIRPSANTGDSLL
SEQ ID NO: 6         TDQGRSGKQPTGQQQWGDWCNVIGTGFGIRPSSNTGDSLL
SEQ ID NO: 7         TDTGRNGKQPTGQQAWGDWCNVIGTGFGARPSTNTGDSLL
SEQ ID NO: 8         VDTGRNGKQPTGQQAWGDWCNVINTGFGERPTTDTGDALV
SEQ ID NO: 9         VDTGRNGNQPTGQSQWGDWCNVKNTGFGVRPTTDTGDELV
SEQ ID NO: 10        TDTGRNGKQPTGQSAWGDWCNVKDTGFGAQPTTDTGDELA
SEQ ID NO: 11        MDTSRNGVQPTKQQAWGDWCNVIGTGFGVQPTTNTGDPLE
SEQ ID NO: 12        IDTSRNGVRPTKQSQWGDWCNVIGTGFGVRPTTDTGNPLE
SEQ ID NO: 13        VDQGRSGKQPTGQKAWGDWCNAPGTGFGLRPSANTGDALV
SEQ ID NO: 14        VDQGRSGKQPTGQKAQGDWCNAKGTGFGLRPSTNTGDALA
SEQ ID NO: 15        VDTGRSGKQPTGQIEQGDWCNAIGTGFGVRPTTNTGSSLA
SEQ ID NO: 16        VDTGRNGKQPTGQIEWGDWCNVKGTGFGVRPTTDTGDELV
SEQ ID NO: 17        TDTGRNGKQPTGQSAWGDWGNVKDTGFGAXPTTDTGNELA
SEQ ID NO: 18        IDQGRSGKQPTGQKEWGHWCNQQGVGFGRRPSANTGSELA
SEQ ID NO: 19        VDTGRNGKQPTGQLEWGHWCNVKGTGFGVRPTANTGHELV
SEQ ID NO: 20        VDTGRNGKQPTGQLEWGHWCNVKGTGFGVRPTANTGHELV
SEQ ID NO: 21        VDQGRSGRQPTGQQEWGHWCNAIGTGFGQRPTSNTGHADV
SEQ ID NO: 22        VDQGRSGKQPTGQKEWGHWCNAIGTGFGMRPTANTGHQYV
SEQ ID NO: 23        VDQGRSGKQPTGQKEWGHWCNAIGTGFGMRPTANTGHQYV
SEQ ID NO: 24        VDQGRSGKVPTNQQEWGDWCNVSGAGFGTRPTTNTGNALI
SEQ ID NO: 25        VDQGRSGVQ-NIRDQWGDWCNVKGAGFGQRPTTNTGSSLI
SEQ ID NO: 26        VDQGRSGQQ-NLRQQWGDWCNIKGAGFGTRPTTNTGSSLI
SEQ ID NO: 27        VDQGRSGVQ-DIRQQWGDWCNVLGAGFGTQPTTNTGSSLI
SEQ ID NO: 28        VDQGRSGVQ-DIRQQWGDWCNVLGAGFGTQPTTNTGSSLI
SEQ ID NO: 29        VDQGRSGVQPTAQIEQGHWCNVIDTGFGTRPTTDTGNEYV
SEQ ID NO: 30        VDQGRSGVQ-NIRQQWGDWCNIKGAGFGTRPTTNTGSQFI
SEQ ID NO: 31        VDQGRSGVQ-NIRQQWGDWCNVKGAGFGQRPTLSTGSSLI
SEQ ID NO: 32        IDTGRNGVT-GLRDEWGDWCNVNGAGFGVRPTANTGDELA
SEQ ID NO: 33        VDQGRSAVQ-GIRGAWGDWCNVDNAGFGTRPTTSTGSSLI
SEQ ID NO: 34        VDQGRAGQQ-NFRQQWGDWCNIKGAGFGTRPTTSTGNPLI
SEQ ID NO: 35        VDTGRNGVS-GLRQEWGNWCNVNGAGFGVRPTSSTGHDLA
SEQ ID NO: 36        VDVGRNAVQ-GLREEWGHWCNVNGAGFGVRPTTSTGSSLT
```

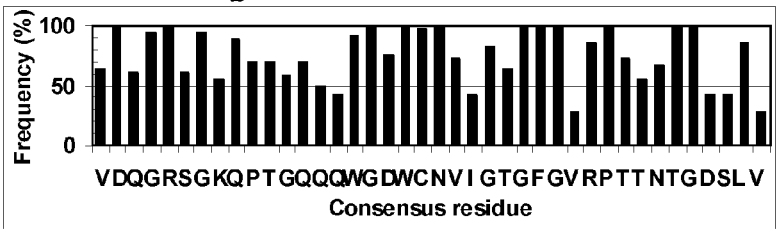

Figure 1 (Cont'd)

```
SEQ ID NO: 1   389  DSFVWVKPGGECDGTS-DSSAPRFDSHCALP-DALQPAPQ  426
SEQ ID NO: 2        DSFVWVKPGGECDGTS-DSSAPRFDSHCALP-DALQPAPQ
SEQ ID NO: 3        DSFVWVKPGGECDGTS-DSSAPRFDSHCALP-DALQPAPQ
SEQ ID NO: 4        DSFVWIKPGGECDGTS-DSSAPRFDSHCALP-DALQPAPQ
SEQ ID NO: 5        DSFVWIKPGGECDGTS-DSSAPRFDSHCALP-DALQPAPQ
SEQ ID NO: 6        DSFVWVKPGGECDGTS-DSSAPRFDSHCALP-DALQPAPQ
SEQ ID NO: 7        DAFVWVKPGGESDGTS-DTSAARYDAHCGYS-DALQPAPE
SEQ ID NO: 8        DAFVWVKPGGESDGTS-DSSATRYDAHCGYS-DALQPAPE
SEQ ID NO: 9        DAFVWVKPGGESDGTS-DTSAERYDAHCGYA-DALTPAPE
SEQ ID NO: 10       DAFVWVKPGGESDGTS-DTSSSRYDAHCGYS-DALQPAPE
SEQ ID NO: 11       DAFVWVKPGGESDGTS-NSSATRYDFHCGYS-DALQPAPE
SEQ ID NO: 12       DAFVWVKPGGESDGTS-NTTSPRYDYHCGLS-DALQPAPE
SEQ ID NO: 13       DAFVWVKPGGESDGTS-DTSAARYDYHCGID-GAVKPAPE
SEQ ID NO: 14       DAFVWVKPGGESDGTS-DTSAARYDYHCGLD-DALKPAPE
SEQ ID NO: 15       DAFVWVKPGGESDGTS-DTSATRYDYHCGLS-DALKPAPE
SEQ ID NO: 16       DAFVWVKPGGESDGTS-DQSAERYDAHCGAA-AALQPAPE
SEQ ID NO: 17       DAFVWXNPGGKSDGTS-DTSSSRYDAHCGYS-DALQPAPE
SEQ ID NO: 18       DAFVWIKPGGECDGVS-DPTAPRFDHFCGTDYGAMSDAPQ
SEQ ID NO: 19       DAFVWVKPGGESDGTSADTSAARYDYHCGLS-DALTPAPE
SEQ ID NO: 20       DAFVWVKPGGESDGTS-DTSAARYDYHCGLS-DALTPAPE
SEQ ID NO: 21       DAFVWIKPGGECDGTS-DTSAARYDHFCGNP-DALKPAPE
SEQ ID NO: 22       DAFVWVKPGGECDGTS-DTTAARYDYHCGLE-DALKPAPE
SEQ ID NO: 23       DAFVWVKPGGECDGTS-DTTAARYDYHCGLE-DALKPAPE
SEQ ID NO: 24       DAIVWVKPGGESDGTS-DTSAARYDAHCGRN-SAFKPAPE
SEQ ID NO: 25       DAIVWVKPGGECDGTS-DNSSPRFDSHCSLS-DAHQPAPE
SEQ ID NO: 26       DAIVWVKPGGESDGTS-NSSSPRFDSTCSLS-DATQPAPE
SEQ ID NO: 27       DSIVWVKPGGECDGTS-NTSSPRYDAHCGLP-DATPNAPE
SEQ ID NO: 28       DSIVWVKPGGECDGTS-NTSSPRYDAHCGLP-DATPNAPE
SEQ ID NO: 29       DSIVWVKPGGESDGTS-DTSAERYDYHCGLE-DALKPAPE
SEQ ID NO: 30       DSIVWVKPGGECDGTS-NSSSPRYDSTCSLP-DAAQPAPE
SEQ ID NO: 31       DAIVWIKPGGECDGTT-NTSSPRYDSHCGLS-DATPNAPE
SEQ ID NO: 32       DAFVWVKPGGECDGTS-DSSAARYDSFCGKP-DAFKPSPE
SEQ ID NO: 33       DAIVWVKPGGESDGTS-DTSAVRYDGHCGLA-SAKKPAPE
SEQ ID NO: 34       DAIIWVKPGGESDGTS-NSSSPRYDSTLLSV-RRDDPAPE
SEQ ID NO: 35       DAFVWVKPGGESDGTS-DSSATRYDSFCGKS-DAYQPSPE
SEQ ID NO: 36       DALLWVKPGGESDGTS-DTSATRYDSFCGMS-DAYKPSPE
```

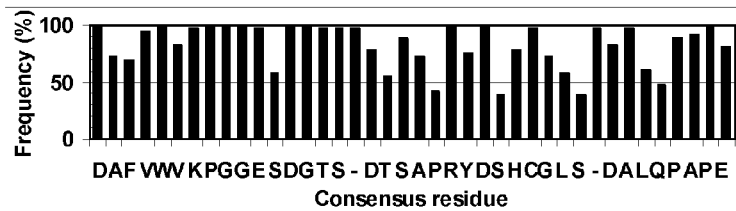

Figure 1 (Cont'd)

```
SEQ ID NO: 1    427 AG------AWFQAYFVQLLTNANPSFL- 447
SEQ ID NO: 2        AG------AWFQAYFVQLLTNANPSFL-
SEQ ID NO: 3        AG------AWFQAYFVQLLTNANPSFL-
SEQ ID NO: 4        AG------AWFQAYFVQLLTNANPSFL-
SEQ ID NO: 5        AG------AWFQAYFVQLLTNANPSFL-
SEQ ID NO: 6        AG------AWFQAYFVQLLTNANPSFL-
SEQ ID NO: 7        AG------TWFQAYFVQLLQNANPSF--
SEQ ID NO: 8        AG------TWFQAYFVQLLTNANPAF--
SEQ ID NO: 9        AG------TWFQAYFEQLVENANPSL--
SEQ ID NO: 10       AG------TWFQAYFEQLLTNANPSL--
SEQ ID NO: 11       AG------TWFQAYFVQLLTNANPALV-
SEQ ID NO: 12       AG------TWFQAYFEQLLTNANPLF--
SEQ ID NO: 13       AG------TWFQAYFEQLLKNANPSFL-
SEQ ID NO: 14       AG------TWFQAYFEQLLDNANPSFL-
SEQ ID NO: 15       AG------QWFQAYFEQLLKNANPAF--
SEQ ID NO: 16       AG------TWFQAYFEQLVANANPPLSS
SEQ ID NO: 17       AG------TWFQAYFEQLLTNANPSL--
SEQ ID NO: 18       AG------QWFQKYFEMLLTNANPPL--
SEQ ID NO: 19       AG------QWFQAYFEQLLINANPPL--
SEQ ID NO: 20       AG------QWFQAYFEQLLINANPPF--
SEQ ID NO: 21       AG------EWFQAYFEQLLRNANPAF--
SEQ ID NO: 22       AG------QWFQAYFEQLLRNANPPF--
SEQ ID NO: 23       AG------QWFNEYFIQLLRNANPPF--
SEQ ID NO: 24       AG------TWFQAYFEMLLKNANPALA-
SEQ ID NO: 25       AG------TWFQAYFETLVANANPAL--
SEQ ID NO: 26       AG------TWFQTYFETLVSKANPPL--
SEQ ID NO: 27       AG------TWFQAYFETLVEKANPPL--
SEQ ID NO: 28       AG------TWFQAYFETLVEKANPPL--
SEQ ID NO: 29       AG------QWFQAYFEQLLRNANPPF--
SEQ ID NO: 30       AG------TWFQAYFQTLVSAANPPL--
SEQ ID NO: 31       AG------QWFQAYFETLVRNASPPL--
SEQ ID NO: 32       AG------TWNQAYFEMLLKNANPSF--
SEQ ID NO: 33       AMASVYSHSSFQAYFEMLVANAVPAL--
SEQ ID NO: 34       AG------TWFQAYFETLVSKPTRPL--
SEQ ID NO: 35       AG------SWNQDYFEMLVKNAKPSF--
SEQ ID NO: 36       AG------QWNQDYFEMLLRNAKPQF-
```

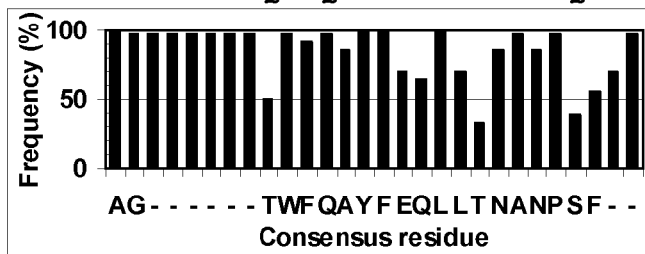

Figure 1 (Cont'd)

| SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|
| 1 | ID | 0.989 | 0.989 | 0.980 | 0.978 | 0.978 | 0.724 | 0.724 | 0.678 | 0.676 | 0.673 | 0.667 | 0.656 | 0.656 | 0.658 | 0.654 | 0.654 | 0.653 | 0.651 | 0.650 | 0.648 | 0.636 | 0.631 | 0.595 | 0.580 | 0.571 | 0.568 | 0.565 | 0.548 | 0.549 | 0.540 | 0.494 | 0.474 | 0.469 | 0.467 | 0.451 |
| 2 | 0.989 | ID | 0.994 | 0.986 | 0.983 | 0.983 | 0.727 | 0.727 | 0.681 | 0.679 | 0.675 | 0.670 | 0.659 | 0.659 | 0.661 | 0.657 | 0.657 | 0.656 | 0.653 | 0.653 | 0.651 | 0.639 | 0.633 | 0.597 | 0.582 | 0.573 | 0.570 | 0.567 | 0.550 | 0.550 | 0.542 | 0.498 | 0.475 | 0.471 | 0.468 | 0.452 |
| 3 | 0.989 | 0.994 | ID | 0.986 | 0.983 | 0.983 | 0.727 | 0.730 | 0.681 | 0.682 | 0.675 | 0.670 | 0.662 | 0.662 | 0.663 | 0.657 | 0.657 | 0.659 | 0.656 | 0.655 | 0.653 | 0.636 | 0.636 | 0.600 | 0.582 | 0.573 | 0.570 | 0.567 | 0.553 | 0.553 | 0.542 | 0.498 | 0.475 | 0.473 | 0.471 | 0.455 |
| 4 | 0.980 | 0.986 | 0.986 | ID | 0.997 | 0.975 | 0.724 | 0.730 | 0.678 | 0.676 | 0.670 | 0.667 | 0.662 | 0.662 | 0.655 | 0.654 | 0.657 | 0.659 | 0.651 | 0.650 | 0.653 | 0.636 | 0.631 | 0.597 | 0.582 | 0.570 | 0.567 | 0.564 | 0.547 | 0.548 | 0.548 | 0.495 | 0.473 | 0.471 | 0.465 | 0.446 |
| 5 | 0.978 | 0.983 | 0.983 | 0.997 | ID | 0.972 | 0.722 | 0.727 | 0.675 | 0.673 | 0.667 | 0.664 | 0.659 | 0.659 | 0.653 | 0.652 | 0.654 | 0.656 | 0.648 | 0.647 | 0.651 | 0.633 | 0.628 | 0.595 | 0.579 | 0.567 | 0.564 | 0.561 | 0.550 | 0.545 | 0.545 | 0.493 | 0.470 | 0.469 | 0.463 | 0.444 |
| 6 | 0.978 | 0.983 | 0.983 | 0.975 | 0.972 | ID | 0.727 | 0.724 | 0.684 | 0.682 | 0.678 | 0.675 | 0.662 | 0.667 | 0.666 | 0.663 | 0.660 | 0.656 | 0.653 | 0.653 | 0.656 | 0.636 | 0.631 | 0.595 | 0.576 | 0.575 | 0.573 | 0.570 | 0.550 | 0.550 | 0.542 | 0.495 | 0.478 | 0.471 | 0.471 | 0.452 |
| 7 | 0.724 | 0.727 | 0.727 | 0.724 | 0.722 | 0.727 | ID | 0.871 | 0.791 | 0.789 | 0.746 | 0.756 | 0.638 | 0.644 | 0.685 | 0.765 | 0.789 | 0.656 | 0.692 | 0.691 | 0.625 | 0.638 | 0.644 | 0.659 | 0.584 | 0.567 | 0.564 | 0.570 | 0.597 | 0.567 | 0.567 | 0.510 | 0.492 | 0.509 | 0.478 | 0.467 |
| 8 | 0.724 | 0.727 | 0.730 | 0.730 | 0.727 | 0.724 | 0.871 | ID | 0.791 | 0.780 | 0.773 | 0.786 | 0.633 | 0.638 | 0.691 | 0.780 | 0.802 | 0.840 | 0.702 | 0.702 | 0.620 | 0.669 | 0.653 | 0.670 | 0.579 | 0.572 | 0.586 | 0.583 | 0.608 | 0.556 | 0.572 | 0.510 | 0.497 | 0.536 | 0.483 | 0.472 |
| 9 | 0.678 | 0.681 | 0.681 | 0.678 | 0.675 | 0.684 | 0.780 | 0.791 | ID | 0.840 | 0.697 | 0.740 | 0.606 | 0.617 | 0.664 | 0.807 | 0.831 | 0.618 | 0.687 | 0.681 | 0.618 | 0.634 | 0.620 | 0.651 | 0.564 | 0.553 | 0.560 | 0.574 | 0.602 | 0.535 | 0.563 | 0.534 | 0.491 | 0.530 | 0.498 | 0.476 |
| 10 | 0.676 | 0.679 | 0.682 | 0.676 | 0.673 | 0.682 | 0.789 | 0.821 | 0.840 | ID | 0.736 | 0.760 | 0.604 | 0.621 | 0.665 | 0.772 | 0.953 | 0.621 | 0.680 | 0.673 | 0.605 | 0.632 | 0.613 | 0.632 | 0.557 | ID | 0.561 | 0.559 | 0.586 | 0.517 | 0.553 | 0.519 | 0.480 | 0.504 | 0.480 | 0.467 |
| 11 | 0.673 | 0.675 | 0.675 | 0.670 | 0.667 | 0.678 | 0.746 | 0.773 | 0.697 | 0.736 | ID | 0.755 | 0.625 | 0.606 | 0.658 | 0.712 | 0.709 | 0.681 | 0.681 | 0.674 | 0.603 | 0.625 | 0.639 | 0.643 | 0.583 | 0.553 | 0.561 | 0.612 | 0.574 | 0.582 | 0.582 | 0.506 | 0.508 | 0.516 | 0.501 | 0.476 |
| 12 | 0.667 | 0.670 | 0.670 | 0.667 | 0.664 | 0.675 | 0.756 | 0.786 | 0.740 | 0.760 | 0.755 | ID | 0.595 | 0.598 | 0.675 | 0.703 | 0.746 | 0.618 | 0.676 | 0.675 | 0.601 | 0.639 | 0.625 | 0.626 | 0.579 | 0.591 | 0.593 | 0.591 | 0.610 | 0.558 | 0.582 | 0.501 | 0.489 | 0.522 | 0.468 | 0.465 |
| 13 | 0.656 | 0.659 | 0.662 | 0.662 | 0.659 | 0.662 | 0.638 | 0.633 | 0.606 | 0.604 | 0.625 | 0.595 | ID | 0.853 | 0.663 | 0.607 | 0.583 | 0.641 | 0.677 | 0.676 | 0.671 | 0.674 | 0.672 | 0.619 | 0.543 | 0.506 | 0.512 | 0.509 | 0.570 | 0.504 | 0.531 | 0.512 | 0.456 | 0.446 | 0.463 | 0.444 |
| 14 | 0.656 | 0.659 | 0.662 | 0.662 | 0.659 | 0.667 | 0.644 | 0.638 | 0.617 | 0.621 | 0.606 | 0.598 | 0.853 | ID | 0.679 | 0.621 | 0.604 | 0.613 | 0.672 | 0.671 | 0.657 | 0.858 | 0.650 | 0.621 | 0.546 | 0.512 | 0.517 | 0.515 | 0.592 | 0.501 | 0.531 | 0.509 | 0.451 | 0.452 | 0.468 | 0.457 |
| 15 | 0.658 | 0.661 | 0.663 | 0.655 | 0.653 | 0.666 | 0.685 | 0.691 | 0.664 | 0.665 | 0.658 | 0.675 | 0.663 | 0.679 | ID | 0.669 | 0.849 | 0.676 | 0.763 | 0.752 | 0.707 | 0.771 | 0.752 | 0.606 | 0.542 | 0.563 | 0.543 | 0.543 | 0.631 | 0.516 | 0.546 | 0.490 | 0.474 | 0.489 | 0.485 | 0.482 |
| 16 | 0.654 | 0.657 | 0.657 | 0.654 | 0.652 | 0.663 | 0.765 | 0.760 | 0.807 | 0.772 | 0.712 | 0.703 | 0.607 | 0.621 | 0.669 | ID | 0.761 | 0.618 | 0.669 | 0.674 | 0.614 | 0.631 | 0.620 | 0.638 | 0.569 | 0.554 | 0.560 | 0.557 | 0.596 | 0.541 | 0.554 | 0.498 | 0.498 | 0.513 | 0.471 | 0.455 |
| 17 | 0.654 | 0.657 | 0.657 | 0.657 | 0.654 | 0.660 | 0.789 | 0.802 | 0.831 | 0.953 | 0.709 | 0.746 | 0.583 | 0.604 | 0.849 | 0.761 | ID | 0.619 | 0.677 | 0.663 | 0.597 | 0.627 | 0.608 | 0.621 | 0.541 | 0.537 | 0.548 | 0.545 | 0.583 | 0.498 | 0.537 | 0.497 | 0.463 | 0.493 | 0.461 | 0.459 |
| 18 | 0.653 | 0.656 | 0.659 | 0.659 | 0.656 | 0.656 | 0.653 | 0.640 | 0.618 | 0.621 | 0.609 | 0.618 | 0.641 | 0.613 | 0.676 | 0.631 | 0.619 | ID | 0.677 | 0.671 | 0.636 | 0.884 | 0.679 | 0.598 | 0.538 | 0.528 | 0.537 | 0.534 | 0.572 | 0.509 | 0.537 | 0.482 | 0.453 | 0.462 | 0.465 | 0.457 |
| 19 | 0.651 | 0.653 | 0.656 | 0.651 | 0.648 | 0.653 | 0.644 | 0.653 | 0.664 | 0.680 | 0.681 | 0.676 | 0.677 | 0.672 | 0.763 | 0.669 | ID | 0.677 | ID | 0.989 | 0.700 | 0.838 | 0.808 | 0.629 | 0.571 | 0.547 | 0.547 | 0.543 | 0.572 | 0.501 | 0.578 | 0.490 | 0.474 | 0.520 | 0.485 | 0.483 |
| 20 | 0.650 | 0.653 | 0.655 | 0.650 | 0.647 | 0.653 | 0.691 | 0.670 | 0.651 | 0.673 | 0.674 | 0.675 | 0.676 | 0.671 | 0.752 | 0.674 | 0.663 | 0.671 | 0.989 | ID | 0.699 | 0.337 | 0.807 | 0.622 | 0.564 | 0.543 | 0.547 | 0.543 | 0.596 | 0.541 | 0.554 | 0.498 | 0.513 | 0.520 | 0.485 | 0.482 |
| 21 | 0.648 | 0.651 | 0.653 | 0.653 | 0.651 | 0.656 | 0.625 | 0.620 | 0.618 | 0.605 | 0.603 | 0.601 | 0.671 | 0.657 | 0.707 | 0.614 | 0.597 | 0.619 | 0.700 | 0.699 | ID | 0.703 | 0.686 | 0.607 | 0.532 | 0.542 | 0.537 | 0.534 | 0.532 | 0.528 | 0.539 | 0.497 | 0.463 | 0.493 | 0.471 | 0.476 |
| 22 | 0.636 | 0.639 | 0.642 | 0.635 | 0.633 | 0.636 | 0.638 | 0.669 | 0.634 | 0.632 | 0.639 | 0.645 | 0.674 | 0.858 | 0.771 | 0.631 | 0.627 | 0.884 | 0.838 | 0.837 | 0.703 | ID | 0.961 | 0.601 | 0.547 | 0.552 | 0.543 | 0.534 | 0.543 | 0.509 | 0.537 | 0.482 | 0.461 | 0.500 | 0.485 | 0.466 |
| 23 | 0.631 | 0.633 | 0.636 | 0.636 | 0.628 | 0.631 | 0.644 | 0.653 | 0.620 | 0.613 | 0.625 | 0.625 | 0.672 | 0.650 | 0.752 | 0.620 | 0.608 | 0.679 | 0.808 | 0.807 | 0.686 | 0.961 | ID | 0.601 | 0.544 | 0.530 | 0.530 | 0.530 | 0.628 | 0.527 | 0.543 | 0.490 | 0.479 | 0.500 | 0.483 | 0.460 |
| 24 | 0.595 | 0.597 | 0.600 | 0.597 | 0.595 | 0.595 | 0.659 | 0.670 | 0.651 | 0.632 | 0.643 | 0.626 | 0.619 | 0.621 | 0.606 | 0.638 | 0.621 | 0.598 | 0.629 | 0.622 | 0.607 | 0.609 | 0.601 | ID | 0.593 | 0.570 | 0.570 | 0.567 | 0.594 | 0.528 | 0.549 | 0.527 | 0.495 | 0.531 | 0.486 | 0.502 |
| 25 | 0.580 | 0.582 | 0.582 | 0.582 | 0.579 | 0.576 | 0.584 | 0.579 | 0.564 | 0.557 | 0.583 | 0.570 | 0.543 | 0.546 | 0.542 | 0.569 | 0.541 | 0.538 | 0.571 | 0.564 | 0.532 | 0.547 | 0.544 | 0.593 | ID | 0.720 | 0.720 | 0.717 | 0.532 | 0.717 | 0.742 | 0.494 | 0.643 | 0.645 | 0.483 | 0.467 |
| 26 | 0.571 | 0.573 | 0.573 | 0.570 | 0.567 | 0.575 | 0.567 | 0.572 | 0.571 | 0.553 | 0.579 | 0.591 | 0.506 | 0.512 | 0.563 | 0.554 | 0.537 | 0.528 | 0.567 | 0.563 | 0.542 | 0.552 | 0.543 | 0.570 | 0.720 | ID | 0.750 | 0.747 | 0.545 | 0.794 | 0.750 | 0.473 | 0.599 | 0.772 | 0.471 | 0.460 |
| 27 | 0.568 | 0.570 | 0.570 | 0.567 | 0.564 | 0.573 | 0.594 | 0.586 | 0.563 | 0.561 | 0.615 | 0.583 | 0.512 | 0.517 | 0.543 | 0.560 | 0.548 | 0.537 | 0.547 | 0.537 | 0.537 | 0.543 | 0.530 | 0.570 | 0.720 | 0.750 | ID | 0.991 | 0.785 | 0.755 | 0.780 | 0.463 | 0.635 | 0.677 | 0.457 | 0.443 |
| 28 | 0.565 | 0.567 | 0.567 | 0.564 | 0.561 | 0.570 | 0.591 | 0.583 | 0.574 | 0.559 | 0.612 | 0.581 | 0.509 | 0.515 | 0.543 | 0.557 | 0.545 | 0.534 | 0.543 | 0.543 | 0.534 | 0.534 | 0.530 | 0.567 | 0.717 | 0.747 | 0.991 | ID | 0.542 | 0.755 | 0.772 | 0.460 | 0.635 | 0.677 | 0.454 | 0.441 |
| 29 | 0.548 | 0.550 | 0.553 | 0.550 | 0.547 | 0.550 | 0.597 | 0.608 | 0.602 | 0.586 | 0.574 | 0.610 | 0.570 | 0.592 | 0.631 | 0.596 | 0.583 | 0.572 | 0.610 | 0.612 | 0.601 | 0.636 | 0.628 | 0.594 | 0.532 | 0.545 | 0.545 | 0.542 | ID | 0.528 | 0.547 | 0.470 | 0.485 | 0.515 | 0.445 | 0.478 |
| 30 | 0.549 | 0.550 | 0.553 | 0.548 | 0.545 | 0.550 | 0.539 | 0.556 | 0.535 | 0.517 | 0.571 | 0.558 | 0.504 | 0.501 | 0.516 | 0.541 | 0.498 | 0.509 | 0.545 | 0.571 | 0.528 | 0.335 | 0.527 | 0.528 | 0.717 | 0.794 | 0.755 | 0.755 | 0.528 | ID | 0.738 | 0.449 | 0.603 | 0.697 | 0.449 | 0.419 |
| 31 | 0.540 | 0.542 | 0.542 | 0.548 | 0.545 | 0.542 | 0.567 | 0.572 | 0.563 | 0.553 | 0.539 | 0.582 | 0.531 | 0.531 | 0.546 | 0.554 | 0.537 | 0.537 | 0.578 | 0.578 | 0.539 | 0.563 | 0.543 | 0.559 | 0.742 | 0.750 | 0.780 | 0.772 | 0.547 | 0.738 | ID | 0.471 | 0.640 | 0.663 | 0.476 | 0.482 |
| 32 | 0.494 | 0.498 | 0.498 | 0.495 | 0.493 | 0.495 | 0.510 | 0.510 | 0.534 | 0.519 | 0.506 | 0.501 | 0.512 | 0.531 | 0.490 | 0.498 | 0.497 | 0.482 | 0.505 | 0.504 | 0.487 | 0.490 | 0.482 | 0.527 | 0.494 | 0.473 | 0.463 | 0.460 | 0.470 | 0.449 | 0.471 | ID | 0.410 | 0.435 | 0.476 | 0.482 |
| 33 | 0.474 | 0.475 | 0.475 | 0.473 | 0.470 | 0.478 | 0.492 | 0.497 | 0.491 | 0.480 | 0.508 | 0.489 | 0.456 | 0.451 | 0.474 | 0.498 | 0.463 | 0.453 | 0.487 | 0.481 | 0.461 | 0.479 | 0.474 | 0.495 | 0.643 | 0.599 | 0.635 | 0.635 | 0.485 | 0.603 | 0.640 | 0.410 | ID | 0.550 | 0.415 | 0.405 |
| 34 | 0.469 | 0.471 | 0.473 | 0.471 | 0.468 | 0.471 | 0.509 | 0.536 | 0.530 | 0.504 | 0.516 | 0.522 | 0.446 | 0.452 | 0.489 | 0.513 | 0.493 | 0.462 | 0.520 | 0.513 | 0.468 | 0.500 | 0.489 | 0.531 | 0.645 | 0.772 | 0.677 | 0.677 | 0.515 | 0.697 | 0.663 | 0.435 | 0.550 | ID | 0.441 | 0.413 |
| 35 | 0.467 | 0.468 | 0.471 | 0.465 | 0.463 | 0.471 | 0.478 | 0.483 | 0.498 | 0.490 | 0.485 | 0.468 | 0.463 | 0.468 | 0.485 | 0.471 | 0.461 | 0.463 | 0.483 | 0.485 | 0.471 | 0.463 | 0.483 | 0.486 | 0.467 | 0.471 | 0.454 | 0.454 | 0.445 | 0.457 | 0.476 | 0.476 | 0.415 | 0.825 | ID | 0.780 |
| 36 | 0.451 | 0.452 | 0.455 | 0.446 | 0.444 | 0.452 | 0.467 | 0.472 | 0.476 | 0.467 | 0.476 | 0.465 | 0.463 | 0.457 | 0.482 | 0.455 | 0.459 | 0.457 | 0.483 | 0.482 | 0.476 | 0.466 | 0.460 | 0.502 | 0.467 | 0.460 | 0.443 | 0.441 | 0.478 | 0.419 | 0.482 | 0.482 | 0.405 | 0.413 | 0.780 | ID |

Figure 2 c)
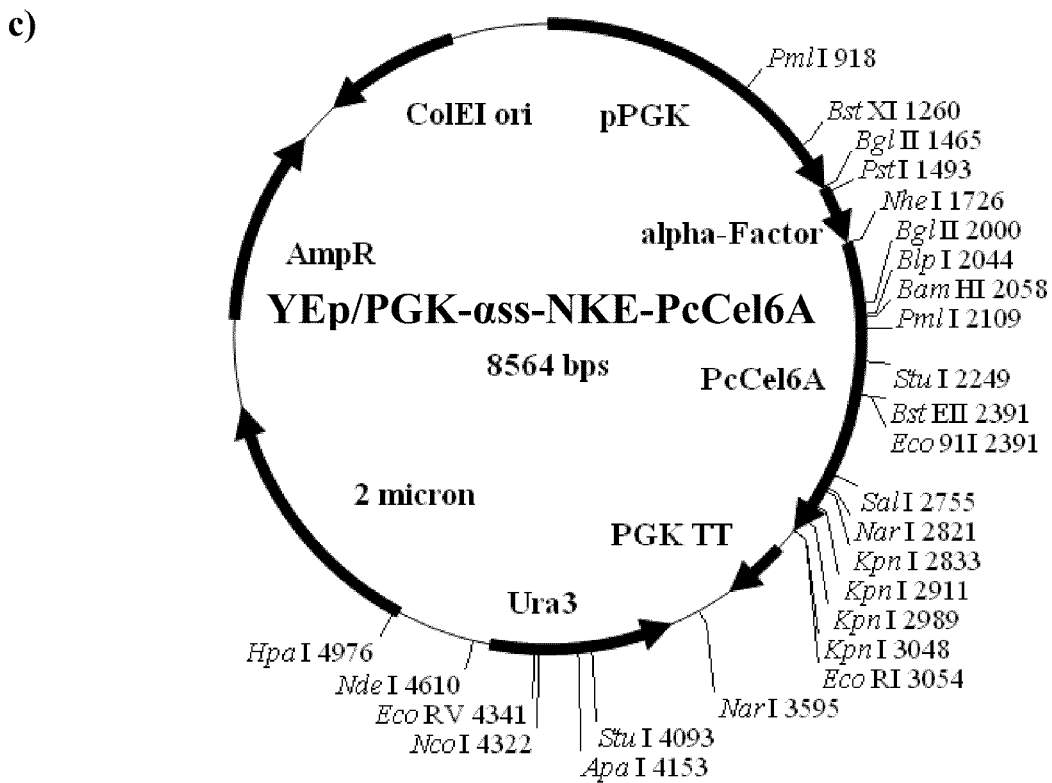
d)
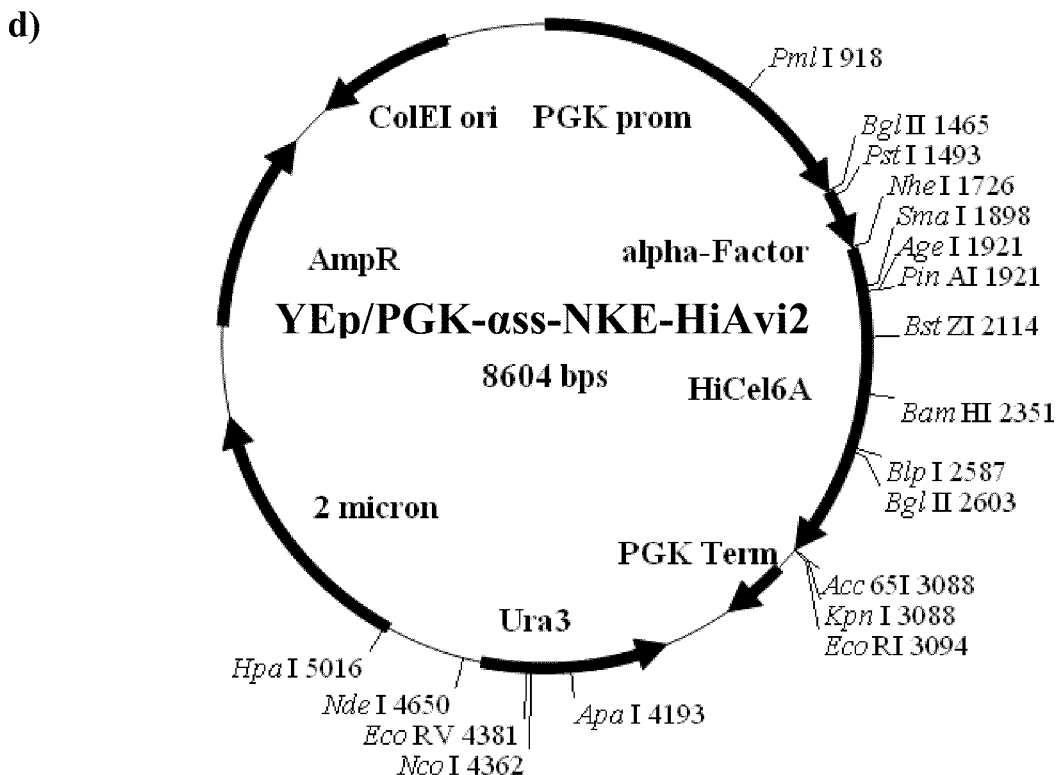
Figure 3 (cont'd)

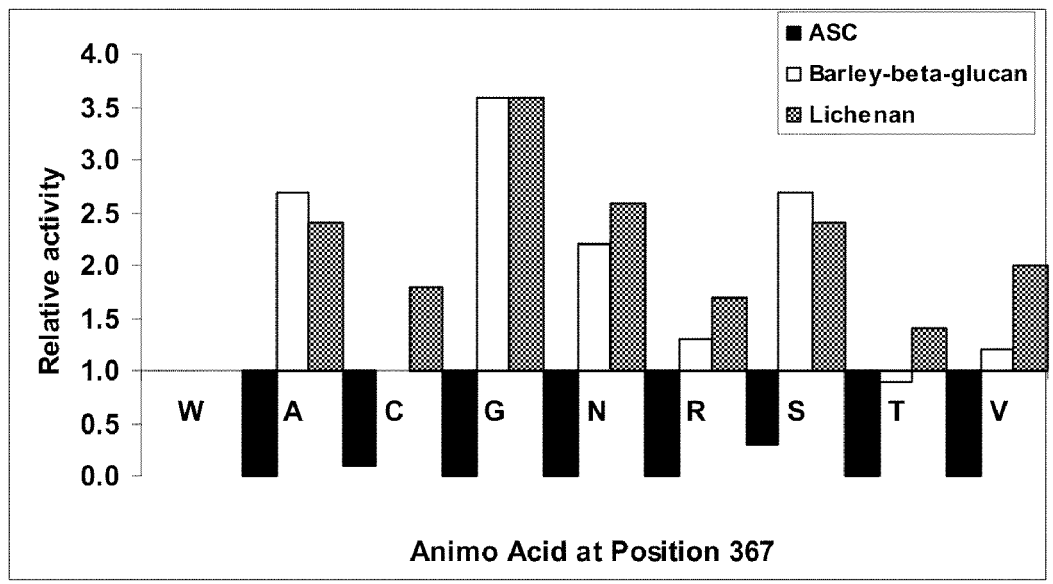
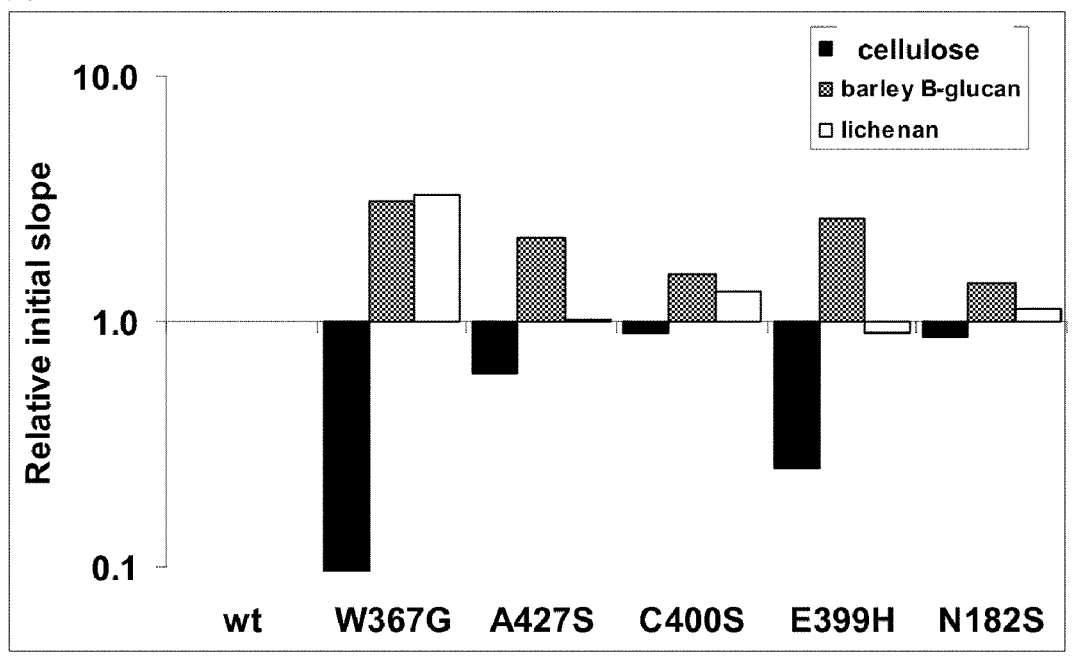
Figure 4

A.
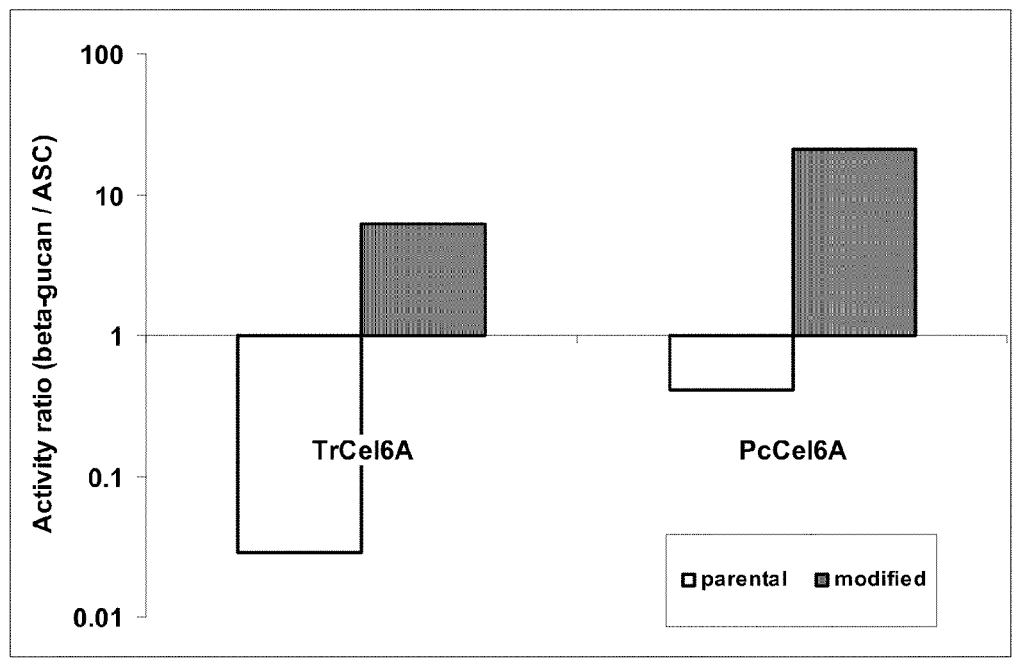
B.
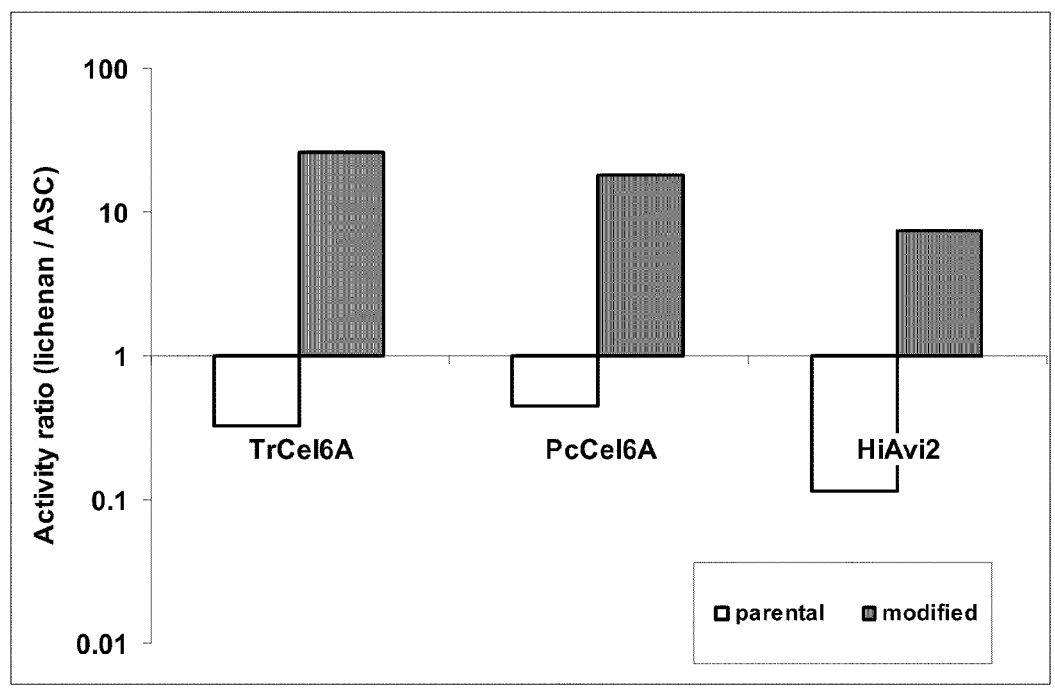
Figure 5

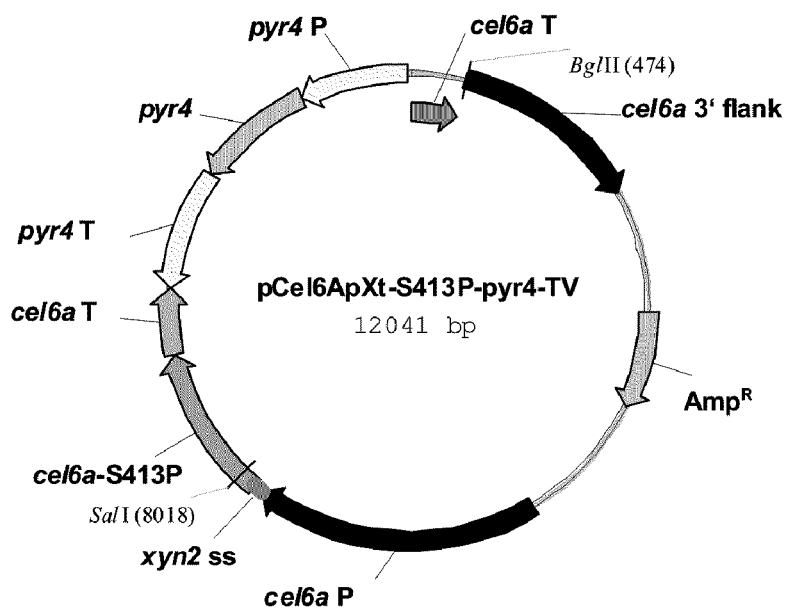
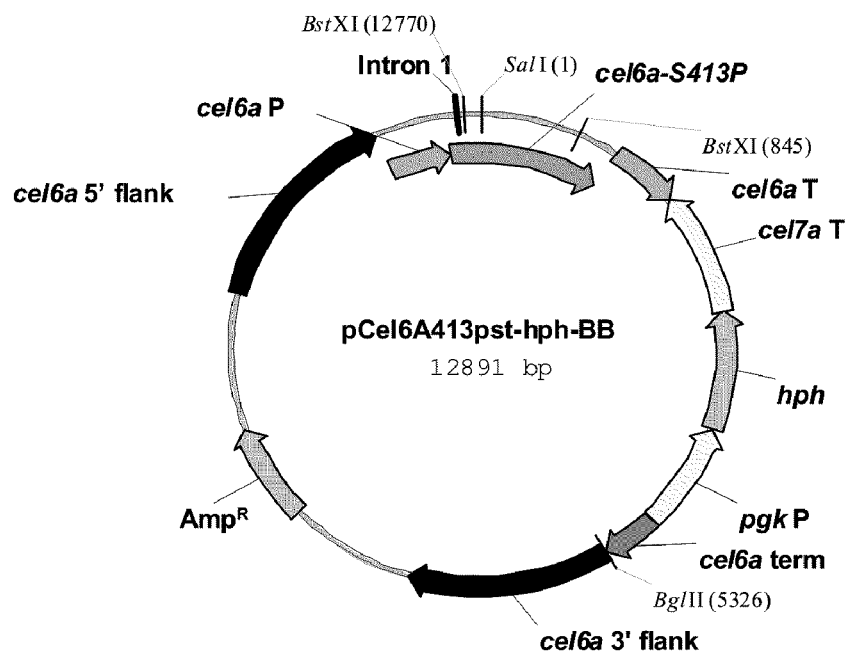
Figure 6

MODIFIED FAMILY 6 GLYCOSIDASES WITH ALTERED SUBSTRATE SPECIFICITY

TECHNICAL FIELD

The present invention relates to modified glycosyl hydrolase (GH) enzymes. More specifically, the invention relates to modified enzymes of the GH Family 6 (GH6) with altered substrate specificity. The present invention also relates to genetic constructs comprising nucleotide sequences that encode and direct the expression and secretion of modified GH enzymes, methods for the production of modified GH enzymes from host strains, and the use of the modified GH enzymes.

BACKGROUND OF THE INVENTION

Glycosyl hydrolases (GHs) are a large group of enzymes that cleave glycosidic bonds between individual carbohydrate monomers in large polysaccharide molecules. For example, cellulases cleave the beta 1-4 bond between glucose monomers in the cellulose polymer; arabinofuranosidases cleave the alpha 1-2 and/or alpha 1-3 bonds between arabinose and xylose in arabinoxylan; amylases cleave the alpha 1-4 bonds between glucose molecules in starch, etc. As a result of the diversity of polysaccharide molecules, there are also many different GH enzymes. However, these enzymes all share one of two common mechanisms, called inverting and retaining, for introducing a water molecule at a glycosidic bond thus cleaving the polysaccharide. The majority of GH enzymes utilize the retaining mechanism.

The GH enzymes are grouped into more than 100 different families based on commonality in their primary and tertiary structures and their catalytic mechanism (CAZy website, URL: cazy.org: Coutinho and Henrissat, 1999). Some GH enzymes families are grouped into larger clans. Depending upon the particular family (all numbers are according to the CAZy website as of 13 March 2008), it may have only a few known examples (e.g., family GH82) or many (e.g. family GH34); more than half of the families have fewer than 200 members. Similarly, all the members of a particular family may represent essentially a single activity, which is to say activity against a single specific substrate (e.g., GH11, all of which are xylanases), whereas other families may have enzymes that cover a wide range of activities (e.g., GH5, comprising cellulases, xylanases, mannanases, chitosanases, galactanases, etc.). Individually, most enzymes have their highest activity for a single substrate, although there are examples of particular enzymes that have high activity against several substrates (e.g. Cel7B from *Trichoderma reesei*, which has both cellulase and xylanase activity).

The GH Family 6 belongs to no clan; it comprises over 100 members, all of which exhibit primarily cellulase activity using the inverting mechanism. Both endo- and exo-cellulases have been identified from a variety of bacterial and fungal sources. In addition, some GH6 members, including Cel6A from *Trichoderma reesei*, have been shown to have hydrolytic activity against beta-glucan, which is a linear polymer of glucose with mixed linkages (Henriksson et al., 1995).

The beta-glucans form a large group of industrially important polysaccharides. Because of their mixed linkages, the beta-glucans have higher solubility in aqueous solutions than more regular polymers such as cellulose. In the soluble form, the beta-glucans confer viscosity and/or gel-like properties to a solution. There are two major types: beta 1-3, 1-6 glucan, also known as laminaran because a major source of this glucan is *Laminaria* brown algae (kelp), and beta 1-3, 1-4 glucan, also known as lichenan because a major source of this glucan is lichen. However, beta 1-3, 1-4 glucan is also found as a major component of oat and barley endosperm. Hydrolysis of beta 1-3, 1-4 glucan from grains is desirable on the industrial scale to reduce viscosity in processes such as brewing, in the production of grain ethanol for fuel, and also to increase nutrient accessibility in animal feeds. In particular, *Trichoderma reesei* Cel6A expressed in brewer's yeast is used to aid in the malting and brewing processes (Enari et al., 1987).

Some efforts to engineer GH enzymes in order to switch their activity from one substrate to another have been made, although experts in protein engineering generally concede that this is one of the more difficult protein engineering challenges (cf. Tao and Cornish, 2002). The research group of W. M de Vos identified three key amino acid residues of a GH1 beta-glucosidase that determined substrate specificity based on a structural comparison to a beta-galactosidase from the same family. By converting the residues of the beta-glucosidase to those found in the beta-galactosidase, they converted the beta-glucosidase into a beta-galactosidase. Similarly, key residues of a GH10 xylanase that discriminate between xylan and cellulose have been identified and mutagenized to change the enzyme from a xylanase to a cellulase (Andrews et al., 2000).

The GH6 family of enzymes have been the target of mutational and protein engineering studies. The exocellulase Cel6A from *Trichoderma reesei*, the exocellulase Cel6A from *Humicola insolens*, and the cellulases Cel6A (endo) and Cel6B (exo) from *Thermobifida fusca* are representative enzymes that have been particularly well characterized. Specific sites of investigation include what are known as the loop regions. These are the principal determinants of whether an enzyme is an endocellulase (lacking loops) or an exocellulase (possessing loops). Mutations in the loops (Varrot et al., 2002) or deletion of the loops (Meinke et al., 1995) will alter the interaction between Cel6A and cellulose. An extensive series of point mutations were studied in the two *T. fusca* enzymes, Cel6A and Cel6B (Zhang et al., 2000a; Zhang et al., 2000b). Changes in the relative activities towards different substrates—specifically filter paper, carboxymethyl cellulose, swollen cellulose and bacterial microcrystalline cellulose—were observed. Other studies have examined the role of aromatic amino acids in substrate binding (Koivula et al., 1996; Koivula et al., 1998; Zou et al., 1999) and the role of charged amino acids in activity and stability (Koivula et al., 2002; Wohlfahrt et al., 2003).

*T. reesei* Cel6A (or TrCel6A) is one of the two major cellobiohydrolases secreted by this fungus and has been shown to be efficient in the enzymatic hydrolysis of crystalline cellulose, with low but measurable activity in the hydrolysis of beta 1,3-1,4 mixed linkage glucans such betaglucan and lichenan. The tryptophan amino acid residue at position 367 (W367) of the *Trichoderma reesei* Cel6A represents a highly conserved residue within a strongly conserved region of the enzyme (FIG. 1). Generally, mutation of conserved residues results in enzyme inactivation, or a severe loss of activity.

SUMMARY OF THE INVENTION

The present invention relates to modified glycosyl hydrolase (GH) enzymes. More specifically, to modified enzymes of the GH Family 6 (GH6) with altered substrate specificity. The present invention also relates to genetic constructs comprising nucleotide sequences that encode and direct the expression and secretion of modified GH enzymes, methods for the production of modified GH enzymes from host strains, and the use of the modified GH enzymes.

It is an object of the invention to provide a modified glycosidase with an altered substrate specificity.

The present invention provides modified glycosidase with an altered substrate preference from EC 3.2.1.91 (cellulase) to EC 3.2.1.73 (beta-glucanase).

The present invention relates to a modified Family 6 glycosidase comprising one or more amino acid substitutions selected from the group consisting of: N182X, W367X, E399X, C/S400X and A427X, the modified Familiy 6 glycosidase having an amino acid sequence in which the amino acids corresponding to those from position 83 to position 447 of TrCel6A (SEQ ID NO: 1) exhibit from about 47% to about 99.9% identity to amino acids 83-447 (TrCel6A numbering) of SEQ ID NO: 1. Furthermore, the one or more amino acid substitutions may be selected from the group consisting of N182S, N182R, N182G, N182A, W367A, W367C, W367G, W367N, W367R, W367S, W367T, W367V, E399H, E399S, E399T, C400V, C400M, C400T, C400S, A427V, A427L, and A427S.

The present invention also provides a modified Family 6 glycosidase comprising one or more amino acid substitutions selected from the group consisting of: N182X, W367X, E399X, C/S400X and A427X, the modified Family 6 glycosidase having an amino acid sequence in which the amino acids corresponding to those from position 83 to position 447 of TrCel6A (SEQ ID NO: 1) exhibit from about 70% to about 99.9% identity to amino acids 83-447 (TrCel6A numbering) of any one of SEQ ID NO: 1 through SEQ ID NO: 36. Furthermore, the one or more amino acid substitutions may be selected from the group consisting of N182S, N182R, N182G, N182A, W367A, W367C, W367G, W367N, W367R, W367S, W367T, W367V, E399H, E399S, E399T, C400V, C400M, C400T, C400S, A427V, A427L, and A427S.

The position of the one or more amino acid substitution defined above may be determined from sequence alignment of the amino acids corresponding to positions 83-447 of SEQ ID NO: 1 of a parental Family 6 glycosidase enzyme with amino acids 83-447 of the *Trichoderma reesei* Cel6A amino acid sequence as defined in SEQ ID NO: 1.

The modified Family 6 glyocosidase may be derived from a parental Family 6 glycosidase that is otherwise identical to the modified Family 6 glycosidase except for the substitution of the naturally occurring amino acid at one or more of positions 182, 367, 399, 400 and 427. For example, this invention includes a modified Family 6 glycosidase as defined above and further comprising a proline residue at position 413.

The modified Family 6 glycosidase comprising these mutations may be from a filamentous fungus, such as *Trichoderma reesei*.

The present invention also relates to a modified Family 6 glycosidase as defined above and that has from about a 1.2-fold increase in activity in the hydrolysis of beta 1-3, 1-4-linked or beta 1-3, 1-6-linked polysaccharides and may also exhibit at least a 1.2-fold decrease in activity in the hydrolysis of beta 1-4-linked polysaccharides relative to a parental Family 6 glycosidase from which it is derived.

The present invention also relates to a modified Family 6 glycosidases selected from the group consisting of:

| | |
|---|---|
| TrCel6A-N182S-S413P; | (SEQ ID NO: 83) |
| TrCel6A-N182R-D350E-S413P; | (SEQ ID NO: 84) |
| TrCel6A-N182G-S413P; | (SEQ ID NO: 85) |
| TrCel6A-N182A-S413P; | (SEQ ID NO: 86) |
| TrCel6A-W367A-S413P; | (SEQ ID NO: 37) |
| TrCel6A-W367C-S413P; | (SEQ ID NO: 38) |
| TrCel6A-W367G-S413P; | (SEQ ID NO: 39) |
| TrCel6A-W367N-S413P; | (SEQ ID NO: 40) |
| TrCel6A-W367R-S413P; | (SEQ ID NO: 41) |
| TrCel6A-W367S-S413P; | (SEQ ID NO: 42) |
| TrCel6A-W367T-S413P; | (SEQ ID NO: 43) |
| TrCel6A-W367V-S413P; | (SEQ ID NO: 44) |
| HiAvi2-W367G; | (SEQ ID NO: 45) |
| PcCel6A-W367G; | (SEQ ID NO: 46) |
| TrCel6A-S25G-T60S-E399H-S413P; | (SEQ ID NO: 87) |
| TrCel6A-E399T-S413P; | (SEQ ID NO: 88) |
| TrCel6A-E399S-S413P; | (SEQ ID NO: 89) |
| TrCel6A-C400V-S413P; | (SEQ ID NO: 90) |
| TrCel6A-C400M-S413P; | (SEQ ID NO: 91) |
| TrCel6A-C400T-S413P; | (SEQ ID NO: 92) |
| TrCel6A-C400S-S413P; | (SEQ ID NO: 93) |
| TrCel6A-A427V-S413P; | (SEQ ID NO: 94) |
| TrCel6A-A427L-S413P; and | (SEQ ID NO: 95) |
| TrCel6A-A427S-S413P. | (SEQ ID NO: 96) |

The present invention relates to genetic constructs comprising a nucleic acid sequence encoding a modified Family 6 glycosidase comprising one or more amino acid substitutions selected from the group consisting of: N182X, W367X, E399X, C/S400X and A427X, the modified Family 6 glycosidase having an amino acid sequence that exhibits from 47% to 99.9% identity to amino acids 83-447 (TrCel6A numbering) of SEQ ID NO: 1 or an amino acid sequence that exhibits from 70% to 99.9% identity to amino acids 83-447 (TrCel6A numbering) of any one of SEQ ID NO: 1 through SEQ ID NO: 36. The nucleic acid sequence may be operably linked to other nucleic acid sequences regulating its expression and secretion from a host microbe. Preferably, the other nucleic sequences regulating the expression and secretion of the modified Family 6 glycosidase are derived from the host microbe used for expression of the modified Family 6 glycosidase. The host microbe may be a yeast, such as *Saccharomyces cerevisiae*, or a filamentous fungus, such as *Trichoderma reesei*.

The invention also relates to a genetic construct as defined above, wherein the modified Family 6 glycosidase encoded by the genetic construct further comprises a substitution of the amino acid at position 413 with a proline or any other additional mutations at positions other than 182, 367, 399, 400 or 427.

The invention also relates to a genetically modified microbe comprising a genetic construct encoding the modified Family 6 glycosidase and capable of expression and secretion of a modified Family 6 glycosidase comprising one or more amino acid substitutions selected from the group consisting of: N182X, W367X, E399X, C/S400X and A427X, the modified Family 6 glycosidase having an amino acid sequence that exhibits 70% to 99.9% identity to amino acids 83-447 (TrCel6A numbering) of SEQ ID NO: 1 or an amino acid sequence that exhibits from 70% to 99.9% identity to amino acids 83-447 (TrCel6A numbering) of any one of SEQ ID NO: 1 through SEQ ID NO: 36. In one embodiment, the genetically modified microbe is capable of expression and secretion of a modified Family 6 glycosidase further comprising a substitution of the amino acid at position 413 with a proline or any other additional mutations at positions other than 182, 367, 399, 400 or 427. The genetically modified microbe may be a yeast or filamentous fungus. For example, the genetically modified microbe may be a species of Saccharomyces, Pichia, Hansenula, Trichoderma, Hypocrea, Aspergillus, Fusarium, Humicola or Neurospora.

The present invention also relates to a process for hydrolysing a beta 1-3, 1-4 -linked polysaccharide substrate with modified Family 6 glycosidase.

The invention also relates to a process of producing the modified Family 6 glycosidase as defined above, including transformation of a yeast or fungal host with a genetic construct comprising a DNA sequence encoding the modified Family 6 glycosidase, selection of recombinant yeast or fungal strains expressing the modified Family 6 glycosidase, culturing the selected recombinant strains in submerged liquid fermentations under conditions that induce the expression of the modified Family 6 glycosidase and recovering the modified Family 6 glycosidase by separation of the culture filtrate from the host microbe.

The inventors have made the surprising discovery that although substitution of N182, W367, E399, C/S400 or A427 by another amino acid generally results in loss of activity against the beta 1-4 linked substrate cellulose, several of these mutations significantly increase the activity of the enzyme towards beta 1-3, 1-4 glucans. Since these amino acids all participate in substrate binding within the active site, the inventors postulate, without wishing to be bound by theory, that the altered substrate specificity of such modified Family 6 glycosidases may be a consequence of an expansion of the enzyme active site to accommodate the branched beta 1-3, 1-4 linked substrates. This altered substrate specificity has potential value applied to industries where reduction of viscosity caused by beta 1-3, 1-4 glucan is desirable, as described above. The modified Family 6 glycosidase exhibits at least about 1.2-fold increase in activity on a beta-1-3, 1-4 linked polysaccharide and may also exhibit at least a 1.2-fold decrease in activity on a beta 1-4 linked polysaccharide such as cellulose. For example, the modified Family 6 glycosidase may exhibit from about a 1.2—to about a 4-fold increase in activity on a beta 1-3, 1-4 linked polysaccharide and may also exhibit from about a 1.2-fold to about a 10-fold decrease in activity on a beta 1-4 linked polysaccharide such as cellulose The modified Family 6 glycosidases of the present display increased activity on beta 1-3, 1-4 -linked polysaccharides and decreased activity on beta 1-4 linked polysaccharides relative to the parental Family 6 glycosidase from which they are derived.

Such glycosidases find use in a variety of applications in industry that require high activity on beta 1-3, 1-4 -linked or beta 1-3, 1-6-linked polysaccharide substrates. For example, modified Family 6 glycosidases, as described herein, may be used in industrial grain processing applications such as brewing, production of grain ethanol for fuel, and also to increase nutrient accessibility in animal feeds.

DESCRIPTION OF THE DRAWINGS

These and other features of the invention will become more apparent from the following description in which reference is made to the appended drawings wherein:

FIG. 1 shows an amino acid sequence alignment among selected fungal glycosidases from Glycosyl Hydrolase Family 6 and a consensus Family 6 glycosidase sequence. A graphical representation of the frequency of occurrence of the amino acid at each position of the consensus Family 6 glycosidase among the 36 fungal Family 6 glycosidases is shown underneath the aligned sequences. The catalytic aspartic acid residues at the equivalent positions 175 and 221 in TrCel6A are indicated by arrows. The highly conserved amino acids at the equivalent of positions 182, 367, 399, 400 and 427 in TrCel6A are indicated with an asterisk. For cellulases with a cellulose-binding domain, only the catalytic core sequences are presented.

FIG. 2 shows an identity matrix for the alignment of the amino acids corresponding to amino acids 83-447 of SEQ ID NO: 1 for each of 36 Family 6 glycosidase amino acid sequences to each other.

FIG. 4 shows the relative activity of modified TrCel6A glycosidases on cellulose, barley beta-glucan and lichenan to the activity of a parental TrCel6A glycosidase on each substrate.

FIG. 5 shows the relative activity of parental and modified TrCel6A, PcCel6A and HiAvi2 glycosidases on (A) barley betaglucan: cellulose and (B) lichenan: cellulose.

FIG. 6 shows the maps of Trichoderma transformation vectors pCel6Apst-S413P-pyr4-TV (A) and pCel6A413pst-hph-BB (B).

DESCRIPTION OF PREFERRED EMBODIMENT

Figure 3:
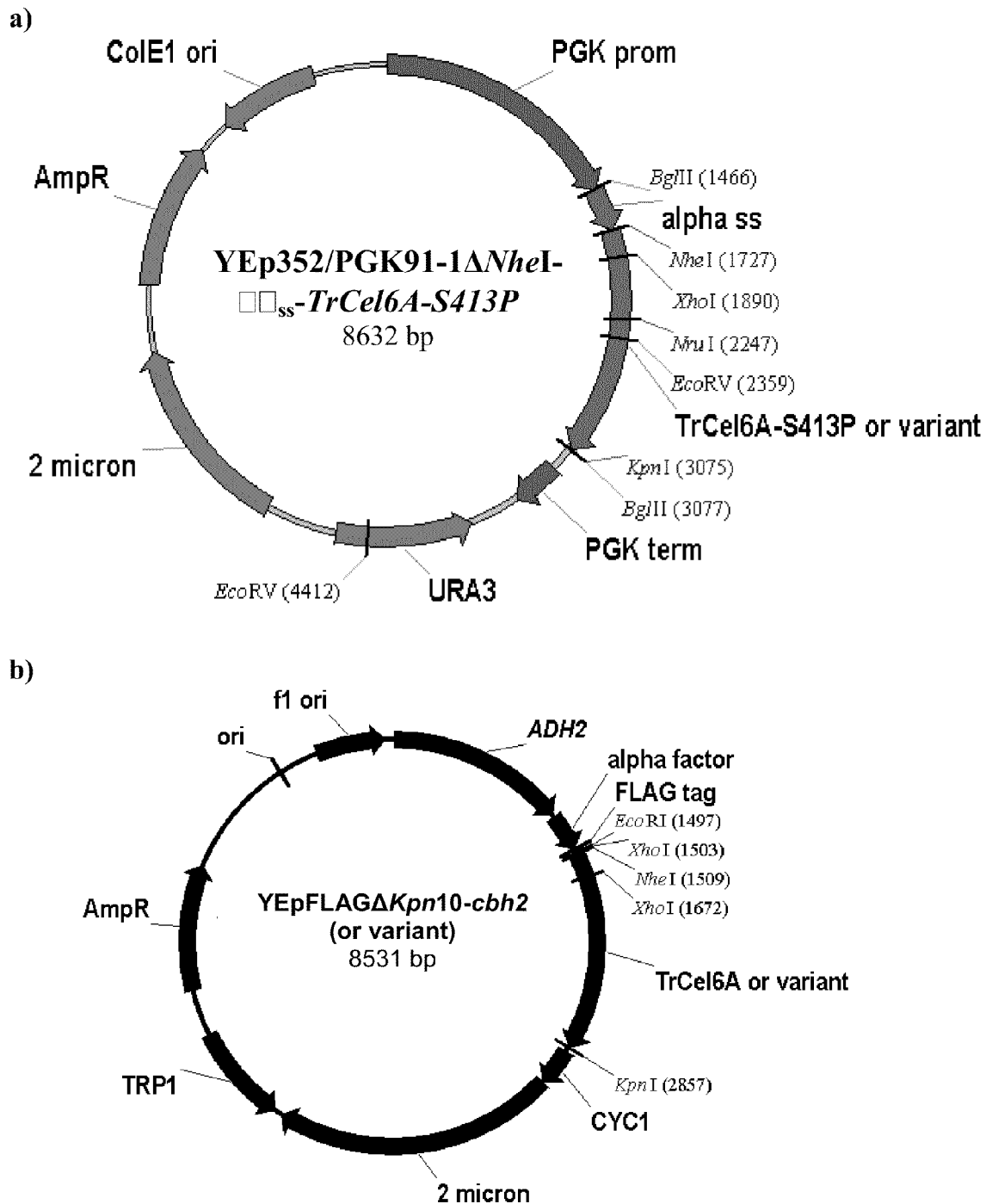
FIG. 3 depicts plasmid vectors a) YEp352/PGK91-1ΔN-heI-α$_{ss}$-TrCel6A-S413P, and b) YEpFLAGΔKpn10-cbh2 directing the expression and secretion of native and modified TrCel6A from recombinant Saccharomyces cerevisiae, c) YEp/PGK-αss-NKE-PcCel6A directing the expression and secretion of native and modified PcCel6A from recombinant Saccharomyces cerevisiae (The same organization if found for the PcCel6 variants cloned in the same vectors), d) YEp/PGK-αss-NKE-HiAvi2 directing the expression and secretion of native and modified HiAvi2 from recombinant Saccharomyces cerevisiae (The same organization if found for the HiAvi2 variants cloned in the same vectors).

The present invention relates to modified glycosidases. More specifically, the invention relates to modified Family 6 glycosidases with altered substrate specificity. The present invention also relates to genetic constructs comprising nucleotide sequences encoding for modified Family 6 glycosidases, methods for the production of the modified Family 6 glycosidase from host strains and the use of the modified Family 6 glycosidase in the hydrolysis of beta-glucan.

The following description is of a preferred embodiment by way of example only and without limitation to the combination of features necessary for carrying the invention into effect.

Modified Glycosidases of Glycosyl Hydrolase Family 6

A glycosyl hydrolase enzyme is classified as a Family 6 glycosidase if exhibits similarity in its primary, secondary and tertiary protein structures to those of other Family 6 glycosidases. For example, all Family 6 glycosidases comprise two aspartic acid (D) residues which may serve as catalytic residues. These aspartic acid residues are found at positions 175 and 221 (see FIG. 1; based on TrCel6A, Trichoderma reesei Cel6A, amino acid numbering). Most of the Family 6 glycosidases identified thus far are mesophilic; however, this family also includes thermostable cellulases from Thermobifida fusca (TfCel6A and TfCel6B) and the alkalophilic cellulases from Humicola insolens (HiCel6A and HiCel6B). Family 6 glycosidases also share a similar three dimensional structure: an alphalbeta-barrel with a central beta-barrel containing seven parallel beta-strands connected by five alpha-helices. The three dimensional structures of several Family 6 glycosidases are known, such as TrCel6A (Rouvinen, J., et al. 1990), Thermobifida fusca endo-beta-1,4-glucanase Cel6A (TfCel6A, Spezio, M., et al. 1993), Humicola insolens cellobiohydrolase Cel6A (HiCel6A, Varrot, A., et al. 1999), Humicola insolens endo-beta-1,4-glucanase Cel6B (HiCel6B, Davies, G. J., et al. 2000) and Mycobacterium tuberculosis H37Rv Cel6A (MtCel6A, Varrot, A., et al. 2005).

As shown in FIGS. 1 and 2, there is a high degree of conservation of primary amino acid sequence among Family 6 glycosidases. Multiple alignment across 36 currently known Family 6 glycosidase amino acid sequences of fungal origin shows that the most naturally occurring Family 6 glycosidases exhibit from about 47% to about 100% amino acid sequence identity to amino acids 83-447 comprising the catalytic domain of TrCel6A (Table 1) and from about 70% to 100% amino acid sequence identity to at least one other Family 6 glycosidase. Family 6 glycosidases of bacterial origin show a much lower degree of amino acid sequence identity to TrCel6A or to other Family 6 glycosidases of fungal origin.

There are several positions where a particular amino acid is universally conserved at the same corresponding position across all Family 6 members. For example, W135, W269, W272 and W367 are highly conserved amino acids that interact with the glucose subunits in the cellulose substrate at the −2, +1, +2 and +4 subsites in the active site tunnel of TrCel6A. N182, E399, and A427 are other highly conserved residues found in the −2 subsite in the active site tunnel of TrCel6A.

TABLE 1

% Amino Acid Sequence Identity of Fungal Family 6 Glycosidases to TrCel6A

| SEQ ID | Organism | Protein | Identity with TrCel6A catalytic domain (83-447) (%) |
|---|---|---|---|
| 2 | Hypocrea koningii | cellobiohydrolase II (Cbh2) | 98.9 |
| 3 | Trichoderma viride CICC 13038 | cellobiohydrolase II (CbhII; Cbh2) | 98.9 |
| 4 | Hypocrea koningii 3.2774 | cellobiohydrolase II (Cbh2; CbhII) | 98.1 |
| 5 | Hypocrea koningii AS3.2774 | cbh2 | 97.8 |
| 6 | Trichoderma parceramosum | cellobiohydrolase II (CbhII) | 97.8 |
| 7 | Aspergillus nidulans FGSC A4 | cellobiohydrolase (AN5282.2) | 72.4 |
| 8 | Aspergillus niger CBS 513.88 | An12g02220 | 72.4 |
| 9 | Aspergillus oryzae RIB 40 | AO090038000439 | 67.8 |
| 10 | Aspergillus niger CBS 513.88 | An08g01760 | 67.7 |
| 11 | Acremonium cellulolyticus Y-94 | cellobiohydrolase II (Acc2) | 67.3 |
| 12 | Talaromyces emersonii | cellobiohydrolase II (CbhII) | 66.8 |
| 13 | Gibberella zeae K59 | Cel6 - Cel6 | 66.1 |
| 14 | Fusarium oxysporum | endoglucanase B | 66.1 |
| 15 | Neurospora crassa OR74A | NCU09680.1 (64C2.180) | 65.9 |
| 16 | Aspergillus nidulans FGSC A4 | AN1273.2 | 65.5 |
| 17 | Aspergillus tubingensis | unnamed protein product (fragment) | 65.5 |
| 18 | Magnaporthe grisea 70-15 | MG05520.4 | 65.4 |
| 19 | Chaetomium thermophilum | unnamed protein product | 65.1 |
| 20 | Chaetomium thermophilum CT2 | cellobiohydrolase (Cbh2) | 65.0 |
| 21 | Stilbella annulata | unnamed protein product | 64.9 |
| 22 | Humicola insolens | avicelase 2 (Avi2) | 63.7 |
| 23 | Humicola insolens | cellobiohydrolase (CBHII) - Cel6A | 63.1 |
| 24 | Cochliobolus heterostrophus C4 | cellobiohydrolase II (CEL7) | 59.6 |
| 25 | Agaricus bisporus D649 | cellobiohydrolase II (Cel3; Cel3A) | 57.7 |
| 26 | Polyporus arcularius 69B-8 | cellobiohydrolase II (Cel2) | 57.1 |
| 27 | Lentinula edodes Stamets CS-2 | cellulase - Cel6B | 56.3 |
| 28 | Lentinula edodes L54 | cellobiohydrolase (CbhII-1) | 56.0 |
| 29 | Malbranchea cinnamomea | unnamed protein product | 54.9 |
| 30 | Phanerochaete chrysosporium | cellobiohydrolase II | 54.9 |
| 31 | Volvariella volvacea | cellobiohydrolase II-I (CbhII-I) | 53.8 |
| 32 | Chrysosporium lucknowense | cellobiohydrolase (EG6; CBH II) - Cel6A | 49.5 |
| 33 | Pleurotus sajor-caju | cellobiohydrolase II | 47.2 |
| 34 | Trametes versicolor | ORF | 47.0 |
| 35 | Neurospora crassa OR74A | NCU03996.1 | 46.8 |
| 36 | Magnaporthe grisea 70-15 | MG04499.4 | 45.1 |

By "TrCel6A numbering", it is meant the numbering corresponding to the position of amino acids based on the amino acid sequence of TrCel6A (Table 1; FIG. 1; SEQ ID NO: 1). As set forth below, and as is evident by FIG. 1, Family 6 glycosidases exhibit a substantial degree of sequence similarity. Therefore, by aligning the amino acids to optimize the sequence similarity between glycosidase enzymes, and by using the amino acid numbering of TrCel6A as the basis for numbering, the positions of amino acids within other Family 6 glycosidases can be determined relative to TrCel6A.

Methods to align amino acid sequences are well known and available to those of skill in the art and include BLAST (Basic Local Alignment Search Tool, URL: blast.ncbi.nlm.nih.gove/Blast.chi; Altschul et al., 1990; using the published default settings) which is useful for aligning two sequences and CLUSTALW (URL: ebi.cak.ak/Tools/clustalw2/index.html) for alignment of two or more sequences.

By "modified Family 6 glycosidase" or "modified glycosidase", it is meant a Family 6 glycosidase which comprises one or more amino acid substitutions, introduced by genetic engineering techniques, selected from the group consisting of: N182X(i.e. N at position 182 is substituted by X), W367X, E399X, C/S400X, and A427X, where X is any amino acid and the position is determined from sequence alignment of the modified Family 6 glycosidase with a *Trichoderma reesei* Cel6A amino acid sequence as defined in SEQ ID NO: 1. For example, the modified Family 6 glycosidase comprises one or more amino acid substitutions selected from the group consisting of: N182S, N182R, N182G, N182A, W367A, W367C, W367G, W367N, W367R, W367S, W367T, W367V, E399H, E399S, E399T, C400V, C400M, C400T, C400S, A427V, A427L, and A427S.

It will be understood that modified Family 6 glycosidase may be derived from any Family 6 glycosidase. For example, the modified Family 6 glycosidase may be derived from a wild-type glycosidase or from a glycosidase that already contains other amino acid substitutions.

A "modified Family 6 glycosidase" may also be defined as an enzyme capable of hydrolyzing polysaccharides using an inverting mechanism and having one or more amino acid substitutions, introduced by genetic engineering techniques, selected from the group consisting of: N182X, W367X, E399X, C/S400X, and A427X, which is characterized by having an amino acid sequence that is from about 47% to about 99.9% identical to the amino acids 83 to 447 of the TrCel6A amino acid sequence (SEQ ID NO: 1) or having an amino acid sequence that is from about 70% to about 99.9% identical to amino acids 83-447 (TrCel6A) of any of the Family 6 glycosidases of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, and SEQ ID NO: 36. For example, a modified Family 6 glycosidase may have an amino acid sequence that is about 47%, 50%, 55%, 60%, 65%, 70%, 75%, 80%, 85%, 90%, 95% or 99.9% identical to the amino acids 83-447 of SEQ ID NO: 1 or that is about 70%, 72%, 74%, 76%, 78%, 80%, 82%, 84%, 86%, 88%, 90%, 92%. 94%, 96%. 98% or 99.9% identical to at amino acids 83-447 (TrCel6A numbering) of any of the Family 6 glycosidases of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, and SEQ ID NO: 36. One of skill in the art recognizes that the amino acid sequence of a given Family 6 glycosidase may be modified by the addition, deletion or substitution of one or more amino acids and still be considered a modified Family 6 glycosidase. Non-limiting examples of Family 6 glycosidases that may be modified following the general approach and methodology as outlined herein are provided in Table 1.

Examples of Family 6 glycosidases useful for the present invention, which are not meant to be limiting, include *Trichoderma reesei* Cel6A, *Humicola insolens* Cel6A, *Phanerochaete chrysosporium* Cel6A, *Cellulomonas fimi* Cel6B, *Thermobifida fusca* Cel6B. Preferably, the modified Family 6 glycosidase of the present invention comprises a modified *Trichoderma reesei* Cel6A glycosidase.

As used herein in respect of modified Family 6 glycosidase amino acid sequences, "derived from" refers to the isolation of a target nucleic acid sequence element encoding the desired modified Family 6 glycosidase using genetic material or nucleic acid or amino acid sequence information specific to the corresponding parental Family 6 glycosidase. As is known by one of skill in the art, such material or sequence information can be used to generate a nucleic acid sequence encoding the desired modified Family 6 glycosidase using one or more molecular biology techniques including, but not limited to, cloning, sub-cloning, amplification by PCR, in vitro synthesis, and the like.

In one embodiment of the invention, the modified Family 6 glycosidase comprises an amino acid sequence that is from about 70% to 99.9% identical to amino acids 83-447 of SEQ ID NO: 1 and exhibits from about a 1.2-fold, for example from about 1.2-fold to 4-fold, increase in activity in the hydrolysis of beta 1-3, 1-4-linked polysaccharides and may also exhibit at least a 1.2-fold, for example from about 1.2-fold to 10-fold, decrease in activity in the hydrolysis of beta 1-4-linked polysaccharides relative to a parental Family 6 glycosidase from which it is derived.

In another embodiment of the invention, the modified Family 6 glycosidase comprises an amino acid sequence that is from about 80% to about 99.9% identical to amino acids 83-447 (TrCel6A numbering) of any one of SEQ ID NO: 1 through 36 and exhibits from about a 1.2-fold increase in activity in the hydrolysis of beta 1-3, 1-4-linked polysaccharides and may also exhibit at least a 1.2-fold decrease in activity in the hydrolysis of beta 1-4 -linked polysaccharides relative to a parental Family 6 glycosidase from which it is derived.

In other embodiments of the invention, the modified Family 6 glycosidase comprises an amino acid sequence that is from about 90% to about 99.9% identical to amino acids 83-447 of SEQ ID NO: 1 or from about 95% to about 99.9% identical to amino acids 83-447 (TrCel6A numbering) of any one of SEQ ID NO: 1 through 36 and exhibits from about a 1.2-fold increase in activity in the hydrolysis of beta 1-3, 1-4-linked polysaccharides and may also exhibit at least a 1.2-fold decrease in activity in the hydrolysis of beta 1-4 -linked polysaccharides relative to a parental Family 6 glycosidase from which it is derived.

Techniques for altering amino acid sequences include, but are not limited to, site-directed mutagenesis, cassette mutagenesis, random mutagenesis, synthetic oligonucleotide construction, cloning and other genetic engineering techniques (Eijsink V G, et al. 2005). It will be understood that the modified Family 6 glycosidase may be derived from any Family 6 glycosidase—i.e., it may be derived from a naturally-occurring or "wild-type" Family 6 glycosidase or from a Family 6 glycosidase that already contains other amino acid substitutions.

By "wild type" or "native" Family 6 glycosidase, it is meant a Family 6 glycosidase having an amino acid sequence as encoded by the genome of the organism that naturally produces such Family 6 glycosidase without the introduction of any substitutions, deletions, insertions, or modifications. For example, by wild type TrCel6A, wild type HiCel6A and wild type PcCel6A it is meant the cellulases of SEQ ID NO: 1, SEQ ID NO: 23 and SEQ ID NO: 30 respectively, without any amino acid substitutions.

For the purposes of the present invention, a "parental Family 6 glycosidase" or "parental glycosidase" is a Family 6 glycosidase that does not contain the amino acid substitution(s) in the modified Family 6 glycosidases, namely at one or more position selected from the group consisting of 182, 367, 399, 400 and 427 (TrCel6A numbering) but that is otherwise identical to the modified Family 6 glycosidase. As such, the parental Family 6 glycosidase may be a Family 6 glycosidase that contains amino acid substitutions at other positions that have been introduced by genetic engineering or other techniques. However, a parental Family 6 glycosidase does not include those Family 6 enzymes in which one or more of the naturally occurring amino acid at positions 182, 367, 399, 400 and 427 are, respectively, tryptophan, asparagine, tryptophan, glutamic acid, cysteine or serine, and alanine.

Alternatively, after production of a modified Family 6 glycosidase comprising amino acid substitutions at one or more of positions 182, 367, 300, 400 and 427, the modified Family 6 glycosidase may be subsequently further modified to contain additional amino acid substitutions.

In order to assist one of skill in the art regarding those amino acid positions of a given Family 6 glycosidase at which amino acid substitutions (other than N182X, W367X, E399X, C/S400X and W427X) may be made and produce an active enzyme, an alignment of 36 Family 6 glycosidases derived from fungal sources is provided in FIG. 1 along with a graph showing the frequency of occurrence of each amino acid of the consensus sequence at each position. Using the information provided in FIG. 1, one of skill in the art would recognize regions of low sequence conservation among Family 6 glycosidases and could introduce additional amino acid substitutions in these regions.

Altering the Substrate Specificity of Family 6 Glycosidases

The substrate specificity of the modified Family 6 glycosidase is determined by incubation of the enzyme in the presence of several different polysaccharides substrate and measuring the release of soluble sugars from those substrates. The release of soluble sugars can be measured by subsequent chemical or chemienzymatic assays known to one of skill in the art, including reaction with dinitrosalisylic acid (DNS). Hydrolysis of polysaccharides can also be monitored by chromatographic methods that separate and quantify soluble mono-, di- and oligo-saccharidses released by the enzyme activity. In addition, soluble calorimetric substrates may be incorporated into agar-medium on which a host microbe expressing and secreting a parental or modified Family 6 glycosidase is grown. In such an agar-plate assay, activity of the glycosidase is detected as a colored or colorless halo around the individual microbial colony expressing and secreting an active glycosidase. The practice of the present invention is not limited by the method used to assess the substrate specificity of the modified Family 6 glycosidase.

The effect of amino acid substitutions at positions 182, 367, 399, 400 and 427 was determined via a comparative study of the substrate specificity of modified and the parental TrCel6A glycosidases. As shown in FIGS. 4 and 5 and summarized for activity on barley beta 1-3, 1-4 glucan in Table 2

TABLE 2

Altered Substrate Specificity of Modified Family 6 Glycosidases

| Amino acid substitution | Relative activity on barley beta 1-3, 1-4 glucan |
|---|---|
| None (TrCel6A-S413P) | 1.0 |
| N182S | 1.53 |
| N182R | 1.69 |
| N182G | 1.60 |
| N182A | 1.55 |
| W367A | 2.70 |
| W367C | 1.00 |
| W367G | 3.60 |
| W367N | 2.20 |
| W367R | 1.30 |
| W367S | 2.70 |
| W367T | 0.91 |
| W367V | 1.20 |
| E399H | 2.58 |
| E399T | 2.52 |
| E399S | 2.80 |
| C400V | 2.09 |
| C400M | 1.97 |
| C400T | 2.12 |
| C400S | 1.59 |
| A427V | 1.67 |
| A427L | 1.95 |
| A427S | 1.68 |

In a preferred embodiment, the modified Family 6 glycosidase exhibits at least a 1.2-fold, for example from about 1.2-fold to about 4-fold, increase in its hydrolysis activity of beta 1-3, 1-4 linked polysaccharides and may also exhibit at least a 1.2-fold, for example from about 1.2-fold to about 10-fold, decrease in its hydrolysis activity of beta 1-4 linked polysaccharides.

Figure 9:
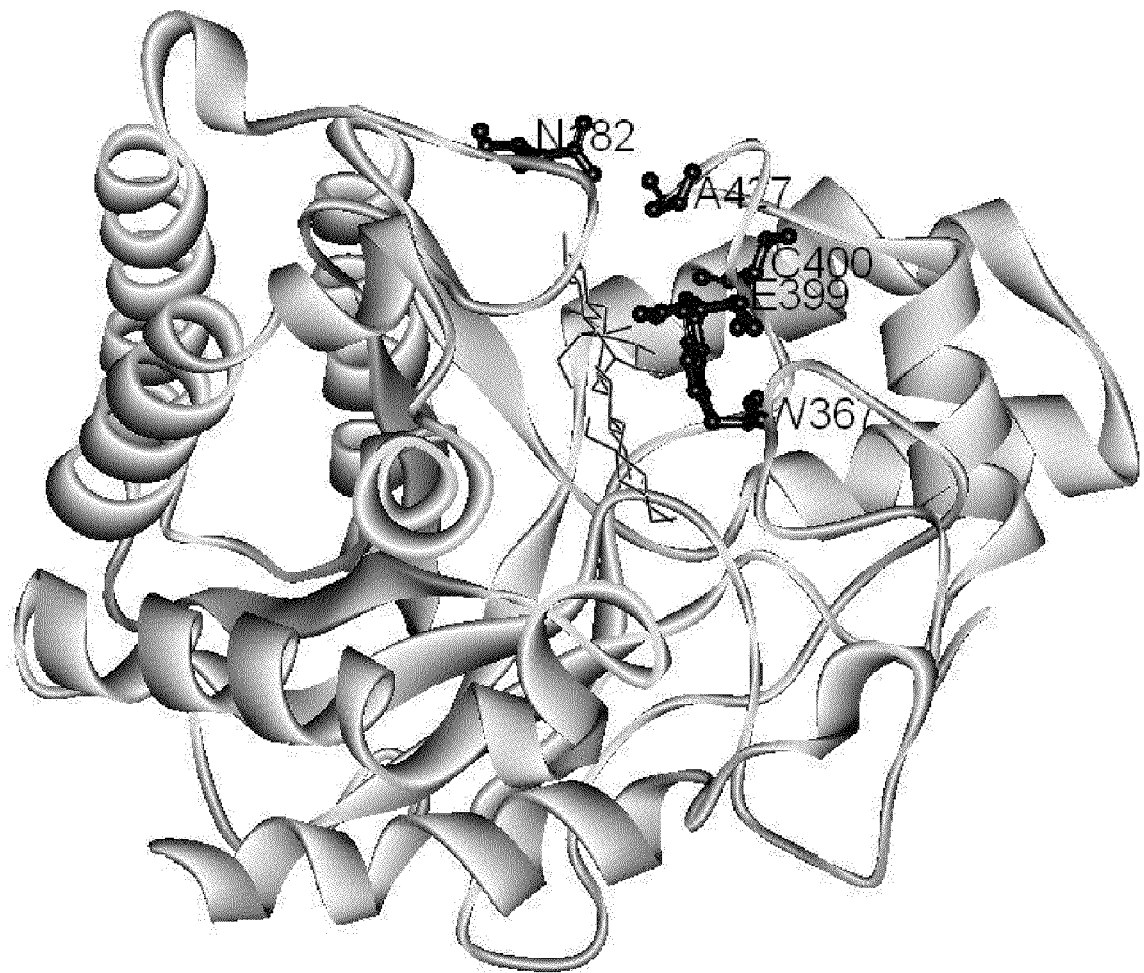
FIG. 9 shows the crystal structure of TrCel6A (using coordinates from PDB file 1QK2) represented in ribbon form with the active-site ligand (cellotetraose) in black sticks and the amino acids at positions 182, 367, 399, 400 and 427 represented as black ball-and-sticks and are labeled. Residues 403 to 424 were removed for ease of visualization.

Without wishing to be bound by theory, the inventors hypothesize that the increased activity on beta 1-3, 1-4 glucans exhibited by the modified Family 6 glycosidases is due to the location of the substituted amino acids within or near the active site of the enzyme. FIG. 9 shows that, for TrCel6A, amino acids W367, E399, C400 are involved in substrate binding while amino acids N182 and A427 are located within the loop regions that enclose the active site tunnel. Therefore, mutations of these highly conserved amino acids may result in a more open or flexible geometry within the TrCel6A active site that allow for the accommodation of the branched beta 1-3, 1-4 glucans.

Genetic Constructs Encoding Modified Family 6 Glycosidase

The present invention also relates to genetic constructs comprising a nucleic acid sequence encoding the modified Family 6 glycosidase. The modified glycosidase-encoding nucleic acid sequence may be operably linked to regulatory nucleic acid sequences directing the expression and secretion of the modified Family 6 glycosidase from a host microbe. By "regulatory DNA sequences" it is meant a promoter and a DNA sequence encoding a secretion signal peptide. The regulatory DNA sequences are preferably functional in a fungal host. The regulatory DNA sequences may be derived from genes that are highly expressed and secreted in the host microbe under industrial fermentation conditions. In a preferred embodiment, the regulatory sequences are derived from one or more of the *Trichoderma reesei* cellulase or hemicellulase genes.

The genetic construct may further comprise a selectable marker gene to enable isolation of a genetically modified microbe transformed with the construct as is commonly known to those of skill in the art. The selectable marker gene may confer resistance to an antibiotic or the ability to grow on medium lacking a specific nutrient to the host organism that otherwise could not grow under these conditions. The present invention is not limited by the choice of selectable marker gene, and one of skill in the art may readily determine an appropriate gene. In a preferred embodiment, the selectable marker gene confers resistance to hygromycin, phleomycin, kanamycin, geneticin, or G418, complements a deficiency of the host microbe in one of the trp, arg, leu, pyr4, pyr, ura3, ura5, his, or ade genes or confers the ability to grow on acetamide as a sole nitrogen source.

The genetic construct may further comprise other nucleic acid sequences, for example, transcriptional terminators, nucleic acid sequences encoding peptide tags, synthetic sequences to link the various nucleic acid sequences together, origins of replication, and the like. The practice of the present invention is not limited by the presence of any one or more of these other nucleic acid sequences.

Genetically Modified Microbes Producing Modified Family 6 Glycosidases

The modified Family 6 glycosidase may be expressed and secreted from a genetically modified microbe produced by transformation of a host microbe with a genetic construct encoding the modified Family 6 glycosidase. The host microbe may be a yeast or a filamentous fungus, particularly those microbes that are members of the phylum *Ascomycota*. Genera of yeasts useful as host microbes for the expression of modified TrCel3A beta-glucosidases of the present invention include *Saccharomyes, Pichia, Hansen ula, Kluyveromyces, Yarrowia*, and *Arxula*. Genera of fungi useful as microbes for the expression of modified TrCel3A beta-glucosidases of the present invention include *Trichoderma, Hypocrea, Aspergillus, Fusarium, Humicola, Neurospora, and Penicillium*. Typically, the host microbe is one from which the gene(s) encoding any or all Family 6 glycosidase have been deleted. In a most preferred embodiment, the host microbe is an industrial strain of *Trichoderma reesei*.

The genetic construct may be introduced into the host microbe by any number of methods known by one skilled in the art of microbial transformation, including but not limited to, treatment of cells with $CaCl_2$, electroporation, biolistic bombardment, PEG-mediated fusion of protoplasts (e.g. White et al., WO 2005/093072). After selecting the recombinant fungal strains expressing the modified Family 6 glycosidase, the selected recombinant strains may be cultured in submerged liquid fermentations under conditions that induce the expression of the modified Family 6 glycosidase. Preferably, the modified Family 6 glycosidase is produced in submerged liquid culture fermentation and separated from the cells at the end of the fermentation. The cells may be separated by filtration, centrifugation, or other processes familiar to those skilled in the art. The cell-free glycosidase-containing fraction may then be concentrated (for example, via ultrafiltration), preserved, and/or stabilized prior to use.

Therefore the present invention also provides a process for producing a modified Family 6 glycosidase. The method comprises growing a genetically modified microbe comprising a nucleotide sequences encoding a modified Family 6 glycosidase, in a culture medium under conditions that induce expression and secretion of the modified Family 6 glycosidase, and recovering the modified Family 6 glycosidase from the culture medium. The modified Family 6 glycosidase comprising one or more amino acid substitution at a position selected from the group consisting of N182X, W367X, E399X, C/S400X, and A427X, the position determined from alignment of a parental Family 6 glycosidase amino acid sequence with a *Trichoderma reesei* Cel6A amino acid sequence as defined in SEQ ID NO: 1, wherein amino acids 83-447 (TrCel6A numbering) of the modified Family 6 glycosidase are from about 47% to about 99.9% identical to amino acids 83-447 of SEQ ID NO: 1, or from about 70-90% identical to amino acids 83-447 of any one of SEQ ID NO: 1 through 36.

Production of Modified TrCel3A Beta-Glucosidases

A modified Family 6 glycosidase of the present invention may be produced in a fermentation process using a genetically modified microbe comprising a genetic construct encoding the modified Family 6 glycosidase, e.g., in submerged liquid culture fermentation.

Submerged liquid fermentations of microorganisms, including *Trichoderma* and related filamentous fungi, are typically conducted as a batch, fed-batch or continuous process. In a batch process, all the necessary materials, with the exception of oxygen for aerobic processes, are placed in a reactor at the start of the operation and the fermentation is allowed to proceed until completion, at which point the product is harvested. A batch process for producing the modified Family 6 glycosidase of the present invention may be carried out in a shake-flask or a bioreactor.

In a fed-batch process, the culture is fed continuously or sequentially with one or more media components without the removal of the culture fluid. In a continuous process, fresh medium is supplied and culture fluid is removed continuously at volumetrically equal rates to maintain the culture at a steady growth rate, One of skill in the art is aware that fermentation medium comprises a carbon source, a nitrogen source and other nutrients, vitamins and minerals which can be added to the fermentation media to improve growth and enzyme production of the host cell. These other media components may be added prior to, simultaneously with or after inoculation of the culture with the host cell.

For the process for producing the modified Family 6 glycosidase of the present invention, the carbon source may comprise a carbohydrate that will induce the expression of the modified Family 6 glycosidase from a genetic construct in the genetically modified microbe. For example, if the genetically modified microbe is a strain of *Trichoderma*, the carbon source may comprise one or more of cellulose, cellobiose, sophorose, and related oligo- or poly-saccharides known to induce expression of cellulases and beta-glucosidase in *Trichoderma*.

In the case of batch fermentation, the carbon source may be added to the fermentation medium prior to or simultaneously with inoculation. In the cases of fed-batch or continuous operations, the carbon source may also be supplied continuously or intermittently during the fermentation process. For example, when the genetically modified microbe is a strain of *Trichoderma*, the carbon feed rate is between 0.2 and 2.5 g carbon/L of culture/h, or any amount therebetween.

The process for producing the modified Family 6 glycosidase of the present invention may be carried at a temperature from about 20° C. to about 40° C., or any temperature therebetween, for example from about 25° C. to about 37° C., or any temperature therebetween, or from 20, 22, 25, 26, 27, 28, 29, 30, 32, 35, 37, 40° C. or any temperature therebetween.

The process for producing the modified Family 6 glycosidase of the present invention may be carried out at a pH from about 3.0 to 6.5, or any pH therebetween, for example from about pH 3.5 to pH 5.5, or any pH therebetween, for example from about pH 3.0, 3.2, 3.4, 3.5, 3.7, 3.8, 4.0, 4.1, 4.2, 4.3, 4.4, 4.5, 4.6, 4.7, 4.8, 4.9, 5.0, 5.2, 5.4, 5.5, 5.7, 5.8, 6.0, 6.2, 6.5 or any pH therebetween.

Following fermentation, the fermentation broth containing the modified Family 6 glycosidase may be used directly, or the modified Family 6 glycosidase may be separated from the fungal cells, for example by filtration or centrifugation. Low molecular solutes such as unconsumed components of the fermentation medium may be removed by ultra-filtration. The modified Family 6 glycosidase may be concentrated, for example, by evaporation, precipitation, sedimentation or filtration. Chemicals such as glycerol, sucrose, sorbitol and the like may be added to stabilize the cellulase enzyme. Other chemicals, such as sodium benzoate or potassium sorbate, may be added to the cellulase enzyme to prevent growth of microbial contamination.

The Use of Modified Family 6 Glycosidase

The modified Family 6 glycosidase of the present invention is used for the enzymatic hydrolysis of polysaccharides containing both beta 1-3, 1-4 and/or beta 1-3, 1-6 glycosidic linkages. More preferably, the modified Family 6 glycosidase of the present invention is used for the enzymatic hydrolysis of beta 1-3, 1-4 glucans present in cereal grains. The modified Family 6 glycosidases of the present invention may be used in industrial processes such as brewing, production of grain ethanol for fuel, and also to increase nutrient accessibility in animal feeds.

By the term "enzymatic hydrolysis", it is meant a process by which glycosidase enzymes or mixtures, including those comprising the modified Family 6 glycosidase of the present invention, act on polysaccharides to convert all or a portion thereof to soluble sugars.

EXAMPLES

The present invention will be further illustrated in the following examples. However, it is to be understood that these examples are for illustrative purposes only and should not be used to limit the scope of the present invention in any manner.

Example 1

Strains and Vectors

*Saccharomyces cerevisiae* strain BY4742 (MATα his3Δ1 leu2Δ0 lys2Δ0 ura3Δ0 Δkre2) was obtained from ATCC (#4014317). The YEp352/PGK91-1 vector was obtained from the National Institute of Health. The YEpFLAGΔKpn 10-S413P vector is described in U.S. Publication No. 2008/0076152A1. The YEpFLAG-1 vector was obtained from Sigma as a part of the Amino-Terminal Yeast FLAG Expression Kit.

Example 2

Cloning of Modified Glycosidase Genes and Transformation of *Saccharomyces cerevisiae* a. Cloning of the TrCel6A-S413P gene into the YEp352/PGK91-1 vector and transformation of *S. cerevisiae* BY4742

In order to facilitate cloning using NheI and KpnI restriction enzymes, the unique NheI site at position 1936 of the YEp352/PGK91-1 vector was blunted using the DNA Polymerase I large (Klenow) fragment to generate YEp352/PGK91-1ΔNheI. The TrCel6A-S413P gene was amplified by PCR from YEpFLAGΔKpn10-S413P vector (U.S. Publication No. 2008/0076152A1) using primers 5'NheCel6A and 3'BglKpnCel6A. In parallel, the yeast (α-factor leader sequence was amplified by PCR from the YEpFLAG- 1 vector (Sigma) using primers (5'BglAlphaSS and 3'NheAlphaSS) to introduce BglII at the 5' end and an NheI site at 3' end of the amplicon. SEQ ID NOS: 47-50 were utilized as primer sequences.

```
                                          (SEQ ID NO: 47)
5'BglAlphaSS:   5'ACC AAA AGA TCT ATG AGA TTT CCT
                TCA ATT (SEQ ID NO: 48)
3'NheAlphaSS:   5'TGA GCA GCT AGC CCT TTT ATC CAA
                AGA TAC (SEQ ID NO: 49)
5'NheCel6A:     5'AAA AGG GCT AGC TGC TCA AGC GTC
                TGG GGC (SEQ ID NO: 50)
3'BglKpnCel6A:  5'GAG CTC AGA TCT GGT ACC TTA CAG
                GAA CGA TGG GTT
```

The yeast alpha-factor leader sequence was isolated by BglII/NheI digestion and a three piece ligation performed with the TrCel6A-S413P gene (isolated by NheI/BglII digestion) and YEp352/PGK91-1ΔNheI vector (isolated by BglII digestion). The resulting vector YEp352/PGK91-1>NheI-α$_{ss}$-TrCel6A-S413P (FIG. 3) was transformed in yeast strain BY4742 using the procedure described by Gietz, R. D. and Woods, R. A. (2002).

b. Cloning of the Pccel6a, Pccel6A-W361G, HiAvi2 and HiAvi2-W374G genes into the YEp/PGK-α$_{ss}$-NKE and transforation in yeast Generation of YEep/PGK-alphass-NKE: Vector YEp352/PGK91-1 was digested with NheI and EcoRI and the plasmid band was isolated from gel. A DNA adapter was made by annealing of AT046 and AT047 5'-phosphorylated primers and was ligated with the digested vector. To eliminate possible concatemerization, the plasmid was then digested with KpnI and self-ligated. The resulting vector is named YEp/PGK-alpha$_{ss}$-NKE and its sequence integrity was confirmed by sequencing.

```
                                          (SEQ ID NO: 54)
AT046:    5' CTA GCT GAT CAC TGA GGT ACC G (SEQ ID NO: 55)
AT047:    5' AAT TCG GTA CCT CAG TGA TCA G
```

Generation of PcCel6A and PcCel6A-W36G vectors: The Pccel6a gene was amplified by PCR from YEpFLAGΔ-Kpn10-PcCel6A vector (U.S. Publication No. 2008/0076152A1) using primers 5'VH098 and 3'VHO99. Pccel6a was cloned NheI/KpnI in YEp/PGK-alpha$_{ss}$-NKE. PcCel6A-W361G was generated by two step PCR by mutating PcCel6A in YEp/PGK-alpha$_{ss}$-NKE using primers 5'VH067 and 3'PGK-term for fragment one and YalphaN21-2 and 3'VH066 to generate fragment two. Fragments 1 and 2 were combined using primers YalphaN21-2 and 3'PGK-term.

```
                                          (SEQ ID NO: 56)
5'VH098:   5' GGT ATC TTT GGA TAA AAG GGC TAG CTC
           GGA GTG GGG ACA G
```

-continued

```
                                          (SEQ ID NO: 57)
3'VH099:    5' GGA GAT CGA ATT CGG TAC CTA CAG CGG
            CGG GTT GG (SEQ ID NO: 58)
5'VH067:    5' CAG TGG GGA GAC GGG TGC AAC ATC AAG (SEQ ID NO: 59)
3'VH066:    5' GTC TCC CCA CTG TTG GCG GAT G (SEQ ID NO: 60)
YalphaN21-2 5' GCC AGC ATT GCT GCT AAA G
```

The resulting vectors, YEpFLAGΔKpn10-PcCel6A and YEpFLAGΔKpn10-PcCel6A -W361G were used to transform *Saccharomyces cerevisiae* strain BY4742 using the procedure described by Gietz, R. D. and Woods, R. A. (2002).

Generation of HiAvi2 and HiAvi2-W374G vectors: The Hiavi2 gene was amplified by PCR from YEpFLAGΔKpn10-HiAvi2 vector (U.S. Patent Provisional No. 60/841,507) using primers 5'NM083 and 3'NM084. HiAvi2 was cloned NheIIKpnI in YEp/PGK-alpha$_{ss}$-NKE. HiAvi2-W374G was generated by two step PCR by mutating HiAvi2 in YEp/PGK-alpha$_{ss}$-NKE using primers 5'VH065 and 3'PGK-term for fragment one and YalphaN21-2 and 3'VH064 to generate fragment two. Fragments 1 and 2 were combined using primers YalphaN21-2 and 3'PGK-term.

```
                                          (SEQ ID NO: 61)
5'NM083: 5' AAG GAT GAC GAT GAC AAG GAA TTC CTC GAG
            GCT AGC TGT GCC CCG ACT TGG GGC (SEQ ID NO: 62)
3'NM084: 5' AGC GGC CGC TTA CCG CGG GTC GAC GGG CCC
            GGT ACC TCA GAA CGG CGG ATT GGC (SEQ ID NO: 63)
5'VH065: 5' GAA TGG GGC CAC GGG TGC AAT GCC ATT GG (SEQ ID NO: 64)
3'VH064: 5' GTG GCC CCA TTC CTT CTG GCC G
```

The resulting vectors, YEpFLAGΔKpn10-HiAvi2 and YEpFLAGΔKpn10-HiAvi2-W374G were used to transform *Saccharomyces cerevisiae* strain BY4742 using the procedure described by Gietz, R. D. and Woods, R. A. (2002).

Example 3

Making Error Prone-PCR Libraries

Random mutagenesis libraries were generated using two methods: a Mutazyme® II DNA polymerase method and a $Mn^{2+}$/biased dNTP mix method. For the Mutazyme® II DNA polymerase method, a series of four independent PCR were performed using 10, 20, 30, 40 ng of YEp352/PGK91-1ΔNheI-α$_{ss}$-TrCel6A-S413P vector and the Mutazyme® II DNA polymerase with primers YalphaN21 and 3'PGK-term. The amplification was done for 25 cycles. The four PCR products were pooled and diluted to 10 ng/μL. A second PCR mutagenesis step was performed using 30 ng of pooled PCR product with Mutazyme® II DNA polymerase using the same primers for 30 amplification cycles. The YEp352/PGK91-1ΔNheI-α$_{ss}$-TrCel6A-S413P vector was digested with NheI and KpnI and the empty vector fragment was isolated. This linear fragment and the final amplicon were transformed simultaneously and cloned by in vivo recombination into yeast strain BY4742 (Butler et al., 2003).

For the $Mn^{2+}$/biased dNTP mix method, a PCR was performed using 25 ng YEp352/PGK91-1ΔNheI-α$_{ss}$-TrCel6A-S413P vector, 0.2 mM dATP, 0.2 mM dCTP, 0.24 mM dGTP, 0.2 mM dTTP, and 0.64 mM $Mn^{2+}$ with Taq DNA polymerase (Sigma) with primers YalphaN21 and 3'PGK-term for 30 amplification cycles. The final amplicon was cloned into YEp352/PGK91-1ΔNheI-α$_{ss}$-TrCel6A-S413P vector as described above.

```
                                          (SEQ ID NO: 49)
YalphaN21:   5'AGC ACA AAT AAC GGG TTA TTG (SEQ ID NO: 50)
3'PGK-term:  5'GCA ACA CCT GGC AAT TCC TTA CC
```

Example 4

Screening of Error-Prone PCR Library of TrCel6A a. Primary Screening of TrCel6A EP-PCR Library—Plate Assay

*Saccharomyces cerevisiae* transformants were grown on plates containing synthetic complete medium (SC: 2% agar w/v, 0.17% yeast nitrogen base w/v, 0.078% -Ura drop-out supplement w/v, 2% glucose w/v, 2% casamino acids w/v, 0.5% ammonium sulfate w/v, pH 5.5) and 0.12% Azo-barley-β-glucan (Megazyme) for 2 days at 30° C. Colonies showing bigger clearing halos, after an overnight incubation at 45° C., compared to the parent enzyme TrCel6A-S413P were selected and sequenced as described below in section c.

b. Primary Screening of TrCel6A EP-PCR Library—Liquid Assay

Clones from the EP-PCR (Example 3) or SSM (Example 5) libraries expressing variants of TrCel6A-S413P were selected for liquid media pre-cultures by toothpick inoculation of 150 μL synthetic complete media (SC: 0.17% yeast nitrogen base w/v, 0.078% -Ura drop-out supplement w/v, 2% glucose w/v, 2% casamino acids w/v, 0.5% ammonium sulfate w/v, pH 5.5) in 96-well microplates. Pre-cultures were grown overnight (16-18 h) at 30° C. and 300 rpm to stationary phase. For expression culture inoculation, 25 μL of pre-culture was used to inoculate 1 mL of SC media in deep-well microplates containing one glass bead. The remaining pre-cultures were used to prepare culture stocks by the addition of glycerol to a final concentration of 15% and stored at −80° C.

Expression cultures were grown for 3 days at 30° C. with orbital shaking and humidity control. Plates were centrifuged at 710×g for 5 minutes to pellet cells and supernatant was aspirated for screening assays. An aliquot (0.05 mL) of yeast supernatant was incubated with 0.5% beta-glucan in a 0.1 mL citrate buffered (50 mM; pH 5) reaction. Activity assays were performed for 3 hours in a PCR plate at 50° C. Contained in each 96-well PCR plate were 6 parental TrCel6A-S413P controls used for comparison. A glucose standard curve was placed in the first column of the PCR plate ranging from 3 to 0.05 mg/mL. Following incubation, 0.08 mL of DNS reagent was added to all wells and the plates were boiled for 10 min. An aliquot (0.15 mL) was transferred to a microplate and the absorbance was measured at 560 nm.

| DNS reagent contains: | |
|---|---|
| Component | g/L |
| 3,5-Dinitosalicylic acid (Acros) | 20 |
| Sodium hydroxide (Fisher) | 20 |
| Phenol (Sigma) | 4 |
| Sodium metabisulfate (Fisher) | 1 |

The concentration of parental or modified TrCel6A glycosidases in yeast filtrates was determined by ELISA. Filtrate and purified component standard were diluted 0.01-10 μg/mL (based on total protein) in phosphate-buffered saline, pH 7.2 (PBS) and incubated overnight at 4° C. in microtitre plates (Costar EIA #9018). These plates were washed with PBS containing 0.1% Tween-20 (PBS/Tween) and then incubated in PBS containing 1% bovine serum albumin (PBS/BSA) for 1 h at room temperature. Blocked microtitre wells were washed with PBS/Tween. Rabbit polyclonal antisera specific for TrCel6A was diluted (1:16,000) in PBS/BSA, added to separate microtitre plates and incubated for 2 h at room temperature. Plates were washed and incubated with a goat anti-rabbit antibody coupled to horseradish peroxidase (Sigma #A6154), diluted 1/2000 in PBS/BSA, for 1 hr at room temperature. After washing, tetramethylbenzidine was added to each plate and incubated for 30 min at room temperature. The absorbance at 360 nm was measured in each well and converted into protein concentration using the TrCel6A standard curve.

Enzyme activity was determined by converting $A_{560}$ values to reducing equivalents using the glucose standard curve. A specific activity was calculated for all modified and parental TrCel6A glycosidases by dividing the enzyme activity by the enzyme concentration determined by ELISA. The specific activity for each modified TrCel6A glycosidase was compared to the average of 6 parental TrCel6A glycosidase controls on a particular microplate and positives were selected at the 95% confidence level using a t-test. All positive variants were produced again in microculture and re-screened to reduce the number of false positives.

c. Sequencing of Genes Encoding Modified Glycosidases

Plasmid DNA comprising genes encoding modified TrCel6A 6 glycosidases with altered substrate specificity was isolated from yeast cultures grown from the glycerol stocks prepared in Example 4b. The modified TrCel6A glycosidase genes were subjected to DNA sequencing to identify mutations that confer altered substrate specificity.

Example 5

Making Site-Saturation Mutagenesis (SSM) Libraries

Site-saturation mutagenesis of residue W367 was performed by megaprimer PCR (two-step PCR reaction) using the mutagenic primer 3'W367X (SEQ ID NO: 51), the YEp352/PGK91-1ΔheI-alpha$_{ss}$-TrCel6A-S413P vector as template, and the Platinum® Taq DNA Polymerase High Fidelity (Invitrogen). The first-step PCR was done using the mutagenic primer 3'W367X and the complementary external primer (YalphaN21 or 3'PGK-term, SEQ ID NOS: 52 and 53, respectively). The purified amplicon served as a megaprimer for the second-step PCR and the other complementary external primers were used to amplify the complete mutated gene. The YEp352/PGK91-1ΔheI-alpha$_{ss}$-TrCel6A-S413P vector was digested with NheI and KpnI and the empty vector fragment was isolated. This linear fragment and the final amplicon were transformed simultaneously and cloned by in vivo recombination into yeast strain BY4742 (Butler et al. 2003).

```
                                        (SEQ ID NO: 51)
3'W367X:     5'CAG CAA CAG TGG GGA GAC NNS TGC AAT
             GTG ATC GGC ACC (SEQ ID NO: 52)
YalphaN21:   5'AGC ACA AAT AAC GGG TTA TTG (SEQ ID NO: 53)
3'PGK-term:  5'GCA ACA CCT GGC AAT TCC TTA CC
```

The amino acids N182, E399, C400 and A427 of TrCel6A were substituted separately for all amino acids (via SSM) by two-step PCR (Table 3) using the following primers:

```
                                        (SEQ ID NO: 60)
YalphaN21-2  5'GCC AGC ATT GCT GCT AAA G (SEQ ID NO: 53)
3'PGK-term   5'GCA ACA CCT GGC AAT TCC TTA CC (SEQ ID NO: 66)
N182X-F      5'CC CTT GCC TCG NNS GGC GAA TAC TC (SEQ ID NO: 65)
N182X-R      5'CGA GGC AAG GGC AGC GCA ATC G (SEQ ID NO: 68)
E399X-F      5'G CCA GGC GGC NNS TGT GAC GGC ACC (SEQ ID NO: 67)
E399X-R      5'GCC GCC TGG CTT GAC CCA GAC AAA CG (SEQ ID NO: 70)
C400X-F      5'CA GGC GGC GAG NNS GAC GGC ACC AG (SEQ ID NO: 69)
C400X-R      5'CTC GCC GCC TGG CTT GAC CCA GAC (SEQ ID NO: 72)
A427X-F      5'CCG GCG CCT CAA NNS GGT GCT TGG TTC C (SEQ ID NO: 71)
A427X-R      5'GAG GCG CCG GTT GCA AGG CAT CTG GG
```

TABLE 3

Two-step PCR performed to generate site-saturated mutagenesis for all four positions.

| Position | PCR 1 and 2, Step 1 | | | PCR Step 2 | | |
|---|---|---|---|---|---|---|
| | Primer 1 | Primer 2 | Size (bp) | Primer 1 | Primer 2 | Size (bp) |
| N182X-1 | YαN21 #2 | N182X-R | 588 | YαN21 #2 | 3'PGK-Term | 1473 |
| N182X-2 | N182X-F | 3'PGK-Term | 896 | | | |
| E399X-1 | YαN21 #2 | E399X-R | 1239 | YαN21 #2 | 3'PGK-Term | 1473 |
| E399X-2 | E399X-F | 3'PGK-Term | 244 | | | |
| C400X-1 | YαN21 #2 | C400X-R | 1242 | YαN21 #2 | 3'PGK-Term | 1473 |
| C400X-2 | C400X-F | 3'PGK-Term | 242 | | | |
| A427X-1 | YαN21 #2 | A427X-R | 1321 | YαN21 #2 | 3'PGK-Term | 1473 |
| A427X-2 | A427X-F | 3'PGK-Term | 162 | | | |

To perform a gap repair the vector Yep/PGK-alpha$_{ss}$-6H-NKE was digested with NheI and KpnI and purified on gel.

*Saccharomyces cerevisiae* strain kre2Δ (MATα his3 Δ1 leu2 Δ0 lys2Δ0 ura3Δ0 Δkre2) was used as the host. The digested YEp/PGK-alpha$_{ss}$-6H-NKE vector and the PCR Step 2 amplicons were transformed in the yeast strain kre2 Δ using the procedure described by Gietz, R. D. and Woods, R. A. (2002).

Example 6

Liquid Assays of Modified Glycosidases to Detect Altered Substrate Preference

TrCel6A-S413P variants from yeast supernatant were tested in liquid assays using three different substrates: barley-β-glucan (Medium Viscosity; Megazyme), lichenan and acid swollen cellulose (ASC, produced from Sigmacell50 using the methods described by Tansey, M. R. 1971).

The activity of each enzyme was determined by measuring the release of reducing sugars from the soluble barley-β-glucan or lichenan substrates. Specifically, in a 300 μL PCR plate, 50 μL of yeast supernatant (dilution series) was mixed with 50 μL of pre-heated 1% (w/v) barley-β-glucan or lichenan in 100 mM sodium citrate pH 5.0. Mixtures were incubated for up to 2 h at 50° C. Following the incubation, 80 μL of DNS reagent was added to each well and the plate was boiled for 10 minutes.

| DNS reagent contains: | |
| --- | --- |
| Component | g/L |
| 3,5-Dinitosalicylic acid (Acros) | 10 |
| Sodium hydroxide (Fisher) | 10 |
| Phenol (Sigma) | 2 |
| Sodium metabisulfate (Fisher) | 0.5 |

Once the temperature decreased below 40° C., 150 μL of each reaction mixture was transferred to individual wells of a 96-well microplate and OD$_{560}$ was measured using a Fluostar Galaxy microplate reader. Blank value was measured by treating the supernatant from the strain carrying the empty vector the same way and was subtracted from each value. The data were fit with Equation A by the method of least squares using the Excel solver and by varying the a and b parameters for each enzyme.

$$y=(a \cdot E)/(b+E) \text{ where } E \text{ represents enzyme concentration} \quad \text{Equation A:}$$

To determine the initial rate of each enzyme, the slope of Equation A was determined as the enzyme concentration approached zero. This was done by substituting E=0 into the first derivative of Equation A. Initial rates for each variant were normalized to wild-type TrCel6A (FIG. 4).

The activity of each enzyme on ASC was tested in a 0.25 mL cellulose hydrolysis assay. TrCel6A variants from yeast supernatant as described in Example 4 were diluted in 50 mM citrate buffer (pH 5.0), complemented with *Trichoderma reesei* Cel7B and Cel5A (10 mg protein/g cellulose) and A. niger beta-glucosidase (125 IU/g cellulose) and incubated with 0.067% ASC. Incubation was at 50° C. for 19 hr. Microplates were centrifuged for 3 min at 2800×g and an aliquot of supernatant was sampled for glucose. Enzyme activity was measured via the detection of glucose using a standard glucose oxidase/peroxidase coupled reaction assay (Trinder, 1969). The data were fit with Equation A by the method of least squares using the Excel solver and by varying the a and b parameters for each enzyme.

$$y=(a \cdot E)/(b+E) \text{ where } E \text{ represents enzyme concentration} \quad \text{Equation A:}$$

To determine the initial rate of each enzyme, the slope of Equation A was determined as the enzyme concentration approached zero. This was done by substituting E=0 into the first derivative of Equation A. Initial rates for each variant were normalized to wild-type TrCel6A (FIG. 4).

FIGS. 4 and 5 show the relative activity of parental modified Family 6 glycosidases on cellulose and two beta-glucan substrates: barley beta-glucan, with a ratio of 3:1 (beta 1-3: beta 1-4) and lichenan, with a ratio of 2:1 (beta 1-3 : beta 1-4). All variants show at least a 1.2-fold increase in activity against one or both of the beta-glucan substrates. Some variants also exhibit more than a 1.2-fold decrease in activity against acid swollen cellulose.

Example 7

Expression of PcCel6A, HiAvi2 and their Variant in Flasks Cultures

*Saccharomyces cerevisiae* transformants were grown on plates containing synthetic complete medium (SC: 2% agar w/v, 0.17% yeast nitrogen base w/v, 0.192% -Ura drop-out supplement w/v, 2% glucose w/v, 2% casamino acids w/v, 0.5% ammonium sulfate w/v, pH 5.5) for 3 days at 30° C.

A single colony of these streaks was used to inoculate 150 μL of synthetic complete medium in a 96-well microplate containing a small sterile glass bead. Pre-cultures were grown overnight (16-18 hr) at 30° C. and 300 rpm to stationary phase. For expression culture inoculation, 25 μL of pre-culture was used to inoculate 50 mL of SC media. Expression cultures were grown for 3 days at 30° C. and 250 rpm with humidity control. Cultures were centrifuged at 3000 rpm for 5 min and the buffer of the supernatant was changed to 50 mM citrate buffer pH 5.0 using a Sartorius filtration device with a 5000 kDa cut-off membrane. All centrifugations for the buffer exchange were done at 4000 rpm at room temperature. The enzymes were washed twice with 20 mL of 50 mM citrate buffer pH 5.0, concentrated in a final volume of 3 mL (approx. 15 fold concentration) of 50 mM citrate buffer pH 5.0, and stored at −20° C.

The activity of each parental and modified PcCel6A and HiAvi2 glycosidase was measured using barley beta-glucan, lichenan and acid-swollen cellulose as described in Example 6 except that HiAvi2 activity assays were performed at pH 6.5.

Example 8

Expression of Modified TrCel6A Glycosidase in *Trichoderma reesei* a. *Trichoderma reesei* Strains

A pyr4 auxotrophic *T. reesei* strain (strain BTR213) was used as a host strain for expression of TrCel6A-W367G-S413. BTR213 is a derivative of RutC30 (ATCC #56765; Montenecourt and Eveleigh, 1979) produced by random mutagenesis and first selected for ability to produce larger clearing zones on minimal media agar containing 1% acid swollen cellulose and 4 g L$^{-1}$ 2-deoxyglucose and then selected for the ability to grow on lactose media containing 0.2 μg/ml carbendazim. The pyr4 auxotroph of strain BTR213 was isolated by the ability to grow on 5-FOA (5-fluororotic acid) and inability to grow prototrophically in the absence of uridine.

b. Construction of Transformation Vectors

Two intermediate vectors, pCel6Apst-hph-TV and pCel6ApXt-hph-TV, containing either genomic cel6a or cDNA cel6a gene versions, respectively, were constructed.

For generation of pCel6Apst-hph-TV, the cel6a promoter, secretion signal, coding sequence, and terminator were isolated from pZUK636 (U.S. Pat. No. 6,015,703) as a 5.1 kb SphI/BglII fragment and inserted into the same sites of pUC-NSNB, a derivative of the standard cloning vector pUC119 containing an adaptor comprising Nhe1-Sph1-Not1-Bg1II restriction sites, make pCel6A-Not. In order to increase the size of the 3' flanking fragment, a 1.7 kb fragment containing part of the cel6a terminator (downstream of the BglII site) and 3' flanking sequence, was amplified from BTR213 using primers KW008 and KW052 (Table 5) and cloned into pGEM T-easy (Promega). KW008 anneals to the internal BglII site located 1 kb downstream of the stop codon while KW052 introduces a SmaI site 2.7 kb downstream of the stop codon. The Cel6A 3' flanking fragment was amplified as a 1.7 kb fragment using BTR213 genomic DNA as a template, digested with BglII and SmaI restriction enzymes and cloned into the same sites of pCel6A-Not to make pCel6Apst-Not. pCel6Apst-Not was linearized with SacII and blunt-ended with T4 polymerase. The hph selection marker cassette was isolated as a 3.1 kb XhoI/EcoRV fragment from pHPT136, blunt-ended, and cloned into the blunted SacII site to make pCel6Apst-hph-TV.

For generation of pCel6ApXt-hph-TV vector the Cel6A promoter was amplified from pZUK636 using primers KW053 and KW054 (Table 4) and cloned into pGEM T-easy (Promega). KW053 spans the SphI site 2.5 kb upstream from the start codon while KW054 introduces a NcoI site at the start codon. The xyn2 secretion signal was amplified from BTR213 genomic DNA using primers KW055 and KW056 with introduced NcoI and NheI sites, respectively, and cloned into pGEM T-easy. A cel6a gene fragment encoding the mature TrCel6A-S413P parental glycosidase and the cel6a terminator were isolated from previously constructed pc/xC2-S413P-TV (U.S. Publication No. 2008/0076152A1) as an NheI/SphI fragment. A three factor ligation with the Cel6A promoter (SphI/NcoI), the xyn2 secretion signal coding sequence (NcoI/NheI) and the pc/xC2-S413P-TV vector fragment (SphI/NheI) was used to make pCel6ApX-S413P. The 5 kb SphI/BglII fragment containing gene encoding TrCel6A-S413P was isolated from pCel6ApX-S413P and cloned into the same sites of pUC-NSNB to make pCel6ApX-S413P-Not. The size of the 3' flanking fragment was increased as described above (pCel6Apst-hph-TV vector construction) generating pCel6AptX-S413P vector. The pCel6AptX-S413P vector was linearized with SacII (located in the Cel6A terminator) and blunt-ended with T4 polymerase. The hph selection marker cassette was isolated as a 3.1 kb XhoI/EcoRV fragment from pHPT136, blunt-ended, and cloned into the blunt-ended SacII site to make pCel6ApXt-hph-TV. The 2.2. kb pyr4 selection marker was isolated as a KpnI fragment from pNcBgl (U.S. Pat. No. 6,939,704), blunted and cloned into the blunted SacII site to make pCel6ApXt-S413P-pyr4-TV (FIG. 6A).

TABLE 4

Primers used for PCR amplification during construction of *Trichoderma* transformation vectors

| Primer | Hybridization site/direction | Sequence | SEQ ID NO: |
|---|---|---|---|
| KW008 | cel6a terminator/Forward | CGAGATCTTCGAGGGCGTAAC | 73 |
| KW052 | cel6a 3' flank/Reverse | GCTCACCCGGGAAGACCACATGGC | 74 |
| KW053 | cel6a 5' flank/Forward | CCGTATAGTATCGCATGCAATTGC | 75 |
| KW054 | cel6a secretion signal/Reverse | GCCGACAACCATGGTGCAATACACAGAGGGTGA | 76 |
| KW055 | xyn2 secretion signal/Forward | CATCACCATGGTCTCCTTCACCTCCCTCCTCGC | 77 |
| KW056 | xyn2 secretion signal/Reverse | CTTGAGCAGCTAGCCTGGCGCTTCTCCACAGCC | 78 |

The final vector for *T. reesei* transformation was generated from two previously constructed Cel6A targeting vectors—pCel6Apst-hph-TV and pCel6ApXt-hph-TV. Both vectors were digested with BglII and SalI restriction enzymes. The fragment from pCel6AXt-hph-TV vector containing Cel6A coding sequence, terminator and hph cassette and the fragment from pCel6Apst-hph-TV vector containing cel6a flanks and AmPR gene were purified from agarose gel and ligated into pCel6A413pst-hph-BB vector (FIG. 6B).

The W367G mutation into cel6a gene was introduced by 3 step PCR ligation as described below. Two pairs of primers (Table 5) were used to amplify partial Cel6A coding sequence and C-terminal Cel6A coding sequence with partial cel6a terminator. Both PCR products have short overlapping ends and were used in the $2^{nd}$ step, ten-cycle PCR reaction as templates and primers to anneal to each over and fill the missing strands at each end. Subsequently, two outside primers, Cel6A-BEII-F1 and Cel6A-Apa-R2, were added and entire fragment was amplified in standard 35 cycle PCR reaction. Amplified PCR product was digested with BstEII and ApaI enzymes and ligated into corresponding sites of pCel6A413pst-hph-BB vector generating pCel6A413/367pst-hph-BB vector.

TABLE 5

Primers used for introduction of W367G mutation into Trichoderma transformation vector.

| Primer | Hybridization site/direction | Sequence | SEQ ID NO: |
|---|---|---|---|
| Cel6a-BEII-F1 | cel6a 5' end at BstEII site/forward | CCTGGTGACCAACCTCGGTAC | 79 |
| Cel6a-367-R3 | cel6a 3' end at 367 amino acid position/reverse | GTGGGGAGACGGGTGCAATGTG | 80 |
| Cel6a-367-F3 | cel6a 3' end at 367 amino acid position/forward | CACATTGCACCCGTCTCCCCAC | 81 |
| Cel6a-Apa-R2 | cel6a terminator at ApaI site/reverse | CCTCTGGGCCCCAGATAAG | 82 | c. Generation of *Trichoderma reesei* Strains Expressing Modified TrCel6A Glycosidases by Direct Replacement of Wild Type cel6a Gene To facilitate screening of *T. reesei* transformants which are targeted to cel6a locus resulting in replacement of wild type cel6a gene with modified Cel6A protein encoding gene we generated host strain with tagged cel6a locus.

The vector pCel6ApXt-S413P-pyr4-TV was transformed into BTR213aux28 *T. reesei* strain using PEG-mediated protoplast transformation method. About $5 \times 10^6$ spores of BTR213aux28 were plated onto sterile cellophane placed on potato dextrose agar (PDA) (Difco) supplemented with 5 mM uridine and incubated for 20 h at 30° C. Cellophane discs with mycelia were transferred to 10 mL of a protoplast preparation solution containing 7.5 g/L Driselase and 4 g/L beta-glucanase (InterSpex Products Inc., Cat. #0465-1 and 0439-2, respectively) in 50 mM potassium phosphate buffer, pH 6.5 containing 0.6 M ammonium sulfate (Buffer P). The mycelia were digested for 5 h at 28° C. with gentle agitation at 60 rpm. Protoplasts were collected by centrifugation at 1000-1500×g for 10 min at room temperature and washed with 5 mL of Buffer P. The pellet was resuspended in 1 mL of STC buffer (1.2 M sorbitol, 10 mM $CaCl_2$, 10 mM Tris-HCL, pH 7.5), separated from undigested mycelia by filtration through sterile No. 60 MIRACLOTH™ and collected into a sterile microcentrifuge tube. For transformation, 0.1 mL of protoplast suspension (approximately $5 \times 10^6$ protoplasts) was combined with 10 µg of vector DNA, linearized with restriction enzyme BglII, and 25 µl of PEG solution (25% PEG 4000, 50 mM $CaCl_2$, 10 mM Tris-HCl, pH 7.5). Protoplasts with DNA were incubated on ice for 30 min then 1 mL of PEG solution was added and the mixture incubated for 5 min at room temperature. Transformation mix was diluted with 2 mL of 1.2 M sorbitol in PEG solution and 4 aliquots of 0.75 mL of the mix were added into 25 mL of molten MMSS agar media (see below) cooled to about 47-50° C. and the protoplast suspensions were poured over MM agar (see below). Plates were incubated at 30° C. until colony growth is visible. Transformants were transferred to individual plates containing MM agar and allowed to sporulate. Spores are collected and plated at high dilution on MM agar to isolate homokaryon transformants, which are then plated onto PDA and incubated at 30° C. for sporulation and subsequent genetic analysis.

| Minimal medium (MM*) agar contains: | |
|---|---|
| Component | Amount for 1 L of medium |
| $KH_2PO_4$ | 10 g |
| $(NH_4)_2SO_4$ | 6 g |
| $Na_3Citrate-2H_2O$ | 3 g |
| $FeSO_4$—$7H_2O$ | 5 mg |
| $MnSO_4$—$H_2O$ | 1.6 mg |
| $ZnSO_4$—$7H_2O$ | 1.4 mg |
| $CaCl_2$—$2H_2O$ | 2 mg |
| Agar | 20 g |
| 20% Glucose f.s. | 50 mL |
| 1 M MgSO4—$7H_2O$ f.s. | 4 mL |
| | pH to 5.5 |

*MMSS agar contains the same components as MM agar plus 1.2 M sorbitol, 4 mM $MgSO_4$, 1 g/L YNB (Yeast Nitrogen Base w/o Amino Acids from DIFCO Cat. No. 291940) and 0.12 g/L amino acids (-Ura DO Supplement from CLONTECH Cat. No. 8601-1).

Three stable *T. reesei* transformants were isolated and integration site of Cel6A targeting cassette was characterized by Southern hybridization analysis. For genomic DNA extraction mitotically stable transformants, P577A, P577B and P577C, and the parental strains, BTR213 and BTR213aux28, were sporulated on PDA. Spores were inoculated in 100 mL of minimal media (MM) media and incubated at 30° C. and 150 rpm for 5 days. Biomass was filtered using GF/A filter, transferred to aluminum foil and frozen immediately at −80° C. for 24 hrs. Frozen biomass was grinded to a fine powder using liquid nitrogen and resuspended in 3 mL of extraction buffer (100 mM Tris pH 8.0, 50 mM EDTA pH 7.5, 1% SDS). Homogenate was transferred to a sterile 15 mL falcon tube and pelleted by cetrifugation at 4000 rpm for 5 min. Supernatant was transferred to a sterile 15 mL falcon tube, equal volume of saturated phenol (pH 6.6) was added and vortexed for 1 min. Aqueous phase containing DNA was separated by centrifugation for 5 min at 4000 rpm and transferred to fresh 15 mL falcon tube. Genomic DNA was further purified by adding an equal volume of phenol:chloroform:isoamyl alcohol (25:24: 1), mixing and separating aqueous phase by centrifugation for 5 min at 4000 rpm. This purification step was repeated until no interphase was visible. Phenol was removed by extracting with an equal volume of chloroform, mixing and separating aqueous phase by centrifugation. Genomic DNA was precipitated overnight at −20° C. using 0.1× volume of 3M NaOAc pH 5.2 and 2.5× volume of 100% EtOH, then pelleted by centrifugation at 4000 rpm for 10-15 min. The pellet was washed once with 1 volume of 70% EtOH and once with 95% EtOH. After the pellet was air dried, the DNA was resuspended in 1 mL of TE buffer (Tris-HCl 10 mM;

EDTA 1 mM; pH 8). To remove RNA, 5 μL of RNase A (10 mg/mL) was added and incubated at 37° C. for 1 hour. RNase then was extracted with 1 volume of saturated phenol (pH 6.6) followed by 1 volume of phenol:chloroform:isoamyl alcohol (25:24:1) and 1 volume of chloroform. DNA was precipitated from separated aqueous phase with 0.1 volume of 3M NaOAc pH 5.2 and 2.5 volume of 100% EtOH, incubated at -20° C. for 30 min, pelleted by centrifugation at 12000 rpm for 15 min and washed once with 1 volume of 70% EtOH and once with 95% EtOH. Finally, the DNA was resuspended in 0.2 mL of TE buffer and used for Southern hybridization as described below.

Figure 7:
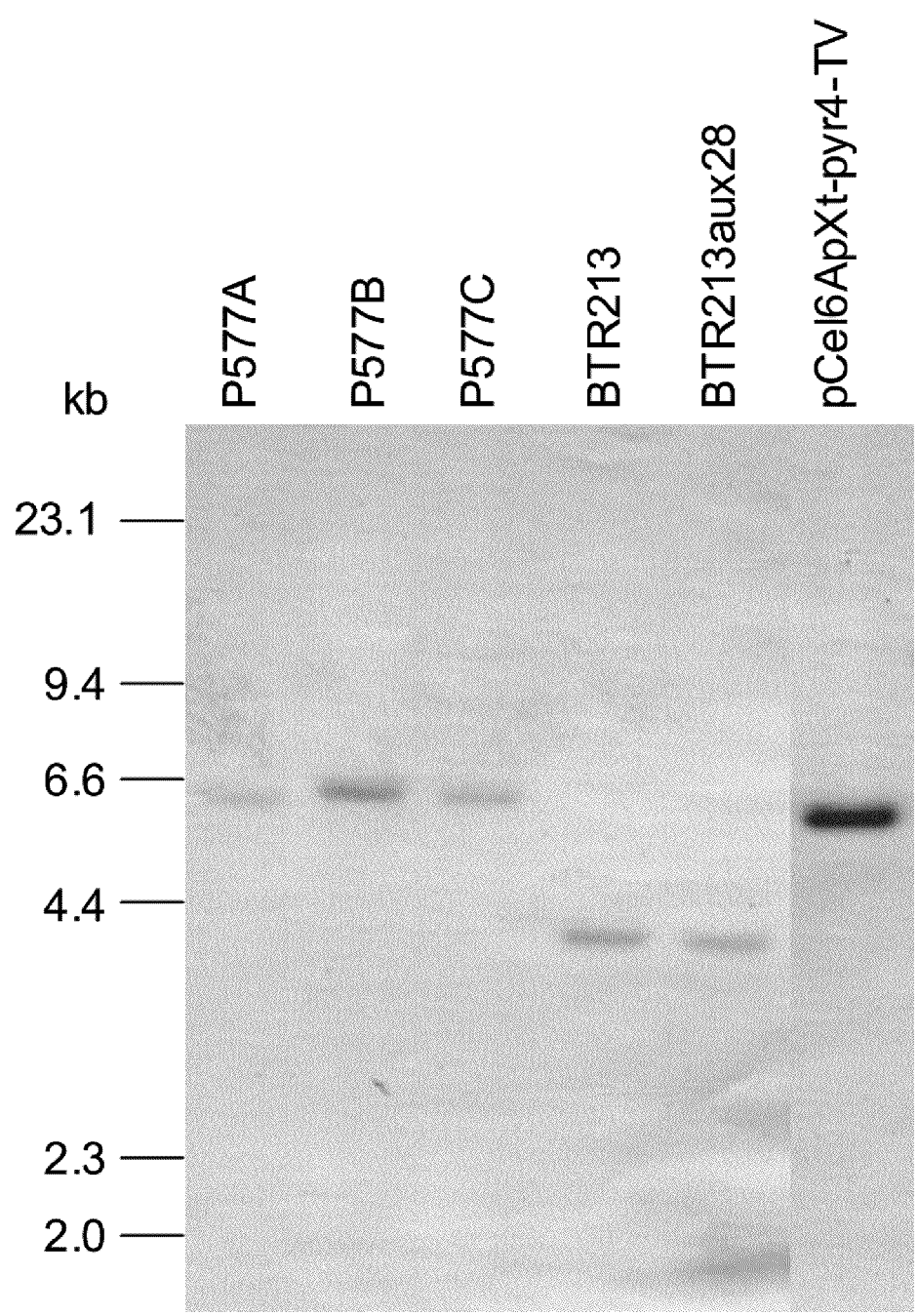
FIG. 7 shows the verification of targeting of the TrCel6A genetic locus to native cel6A locus by Southern hybridization. Genomic DNA was isolated from transformants P577A, B, C and parental strains BTR213, BTR213aux28 digested with EcoRI restriction enzyme, separated on a 1% agarose gel, transferred to a nitrocellulose membrane and hybridized using the TrCel6A coding nucleic acid sequence as a probe. pCel6ApXT-S413P-pyr4-TV transformation plasmid digested with EcoRI was used as a control (lane pCel6ApXt-pyr4-TV).

Southern blot using DIG labeling and detection system was performed as described in the Roche Applied Science manual. The restriction pattern at the wild type cel6a locus expected after digestion of genomic DNA from BTR213 and BTR213aux28 was predicted using cel6a sequence from JGI database URL: genomejgi-psf.org/Trire2/Trire2/home.html) and expected to be detectable as 4.2 kb band specifically hybridizing with cel6a probe (FIG. 7). In the event of ectopic vector integration resulting in presence of two copies of cel6a gene in the genome, two specific bands would be observed. The targeting of Cel6A vectors into cel6a locus in transformants P577A, P577B, and P577C would result in a 6.4 kb fragment, as seen after EcoRI digestion of transformation vector (FIG. 7) due to the presence of tye pyr4 selection cassette. As demonstrated in FIG. 7, the Southern blot confirmed the integration of Cel6A-marker cassettes into the native cel6a locus and replacement of native Cel6A coding sequence with coding sequence from the transformation vector.

d. Generation of *Trichoderma reesei* Transformants Expressing Tr Cel6A-W367G-S413P The vector pCel6A413/367pst-hph-BB was transformed into generated new *T. reesei* host strain, P577C, using PEG-mediated protoplast transformation as described above (Example 8c). The selection of transformants was performed using hygromycin resistance as a selectable marker. Aliquots (0.75 mL) of transformed protoplasts were added into 25 mL of PDA media cooled to about 47-50° C. and the protoplast suspensions were poured into 200 mm Petri dishes. After the PDA media containing transformed protoplasts solidified, another 25 mL of PDA media supplemented with 80U/mL of hygromycin B was added as a top agar. Plates were incubated at 30° C., until colony growth was visible. Transformants were transferred twice to individual plates containing PDA media supplemented with 40 U/mL of hygromycin B (PDAH) and allowed to sporulate. Spores were collected and plated at high dilution on PDAH to isolate homokaryon transformants, which were then plated onto PDA and incubated at 30° C. for sporulation and subsequent analysis.

Transformants possessing targeted vector integration into cel6a locus were identified by their ability to grow in the presence of hygromycin and inability to grow on minimal media lacking uridine supplement. This indicated that the pyr4 selectable marker cassette present in P577C host strain was replaced with modified Cel6A expression and hph selectable marker cassettes.

Example 9

Production of Modified Glycosidase from *Trichoderma reesei* a. Production of TrCel6A-W367G-S413P in *T. reesei* Microcultures

To confirm expression of TrCel6A-W367G-S413P protein, all strains possessing targeted replacement of wild type cel6a gene with TrCel6A-W367G-S413P coding gene were grown in microcultures for Cel6A protein analysis.

*T. reesei* transformants and the parental strain BTR213aux28 were cultured on PDA plates supplemented with 5mM of uridine for 6-7 days at 30° C. The spore suspensions were prepared by washing spores from the agar plate with sterile water. The composition of microculture media containing glucose with cellulase inducing carbohydrates as a carbon source is indicated below.

| *Trichoderma* microculture media | |
|---|---|
| Component | Concentration g/L |
| Glucose with cellulase inducing carbohydrates[a] | 35 |
| Ammonium sulphate | 12.7 |
| KH$_2$PO$_4$ | 8.0 |
| MgSO$_4$—7H2O | 4.0 |
| CaCl$_2$—2H$_2$O | 1.0 |
| FeSO$_4$—7H$_2$O | 0.1 |
| MnSO$_4$—7H2O | 0.032 |
| ZnSO$_4$7H$_2$O | 0.028 |
| CaCO$_3$ | 20 |
| Corn Steep Liquor (powder) | 5 |
| | pH4.24 |

[a]A cellulase-inducing cocktail comprising, as a function of total carbohydrate, 56% gentiobiose, 14% sophorose, 6% cellobiose, 10% trehalose, 6% maltotriose, 4% glucose and 14% other carbohydrates About 5000 *T. reesei* spores were inoculated in each well of 24-well culture dish (COSTAR) containing 1 mL of media. Plates were incubated for 5-7 days at 30° C. with shaking at 250 rpm.

Figure 8:
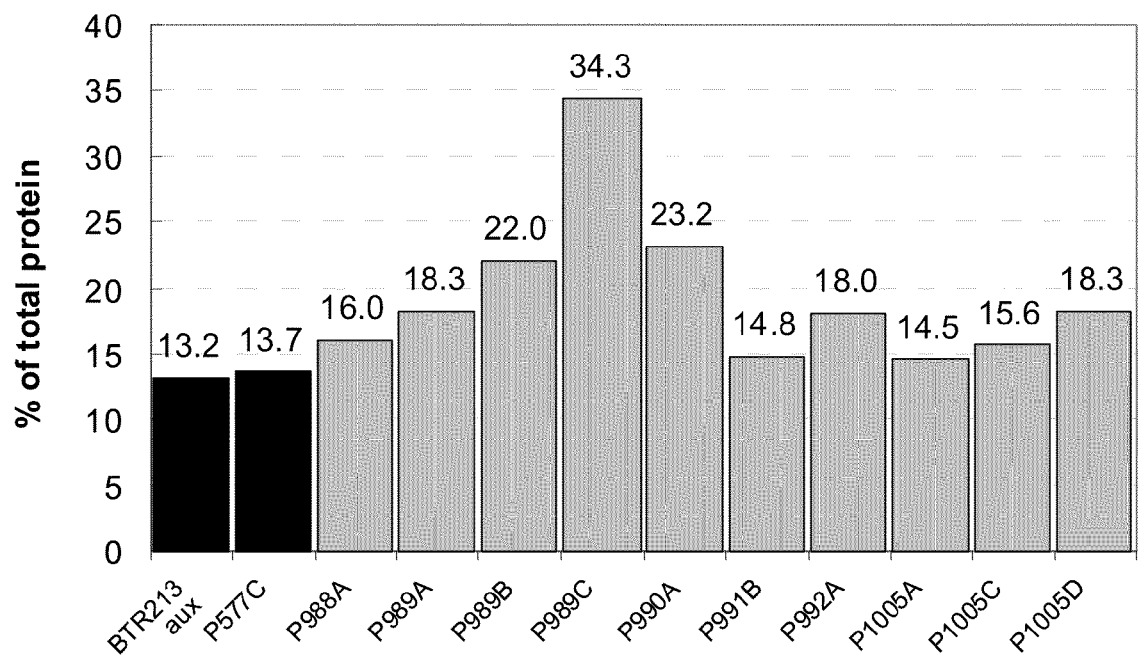
FIG. 8 shows the expression of the modified TrCel6A-W367G-S413P glycosidase by Trichoderma reesi transformants (P988A, P989A, B, C, P990A, P991B, P992A, P1005A, C, D) and the expression of wild-type TrCel6A by the host strain (P577C) and parental strain BTR213aux in microcultures. The abundance of TrCel6A-W367G-S413P or TrCel6A protein is indicated on each bar as a percent of total protein.

The relative concentration of the TrCel6A-W367G-S413P produced by transformants was determined by ELISA (Example 4). The relative concentration of TrCel6A-W367G-S413P protein was calculated by dividing TrCel6A-W367G-S413P concentration by the total amount of protein produced, as determined using a Bradford protein assay. The expression levels of Cel6A are presented in FIG. 8.

b. Analysis of *T. reesei* Transformants in 14L Pilot Fermentations

Two *T. reesei* transformants with the highest Cel6A expression levels, strains P989B and P989B, were selected for 14L fed-batch pilot fermentation and enzyme analysis. *Trichoderma* spores were inoculated onto standard 85 mm Petri plates containing potato dextrose agar (PDA). These plates were incubated at 28° C. for 3-5 days to achieve a confluent growth of fresh green spores. To prepare the inoculum for fermentation, spores from a single PDA plate were transferred to 2 L, baffled Erlenmeyer flasks containing 750 mL of liquid Berkley media (pH 5.5) supplemented with 10 mM of uridine. Flasks were incubated at 28° C. for 3 days using an orbital agitator (Model G-52 New Brunswick Scientific Co.) running at 100 rpm.

| Berkley Media for Flasks | |
|---|---|
| Component | Concentration, g/L |
| (NH$_4$)$_2$SO$_4$ | 1.4 |
| KH$_2$PO$_4$ | 2.0 |
| MgSO$_4$•7H$_2$O | 0.31 |
| CaCl$_2$•2H$_2$O | 0.53 |
| Dry Corn Steep Liquor | 5.1 |

-continued

Berkley Media for Flasks

| Component | Concentration, g/L |
|---|---|
| Glucose | 10 |
| Trace elements* | 1 mL/L |

*Trace elements solution contains 5 g/L FeSO$_4$•7H$_2$0; 1.6 g/L MnSO$_4$•H$_2$0; 1.4 g/L ZnSO$_4$•7H$_2$0.

The contents of an inoculum flask were transferred to a 14L pilot scale fermentation vessel (Model MF114 New Brunswick Scientific Co.) set up with 10 L of Initial Media for Feb-Batch fermentation (pH 5.5) supplemented with 10 mM of uridine. The vessel was run in batch mode until glucose in the media was depleted. At this point, the carbon source containing cellulase inducing carbohydrates (56% gentiobiose, 14% sophorose, 6% cellobiose, 10% trehalose, 6% maltotriose, 4% glucose and 14% other carbohydrates) was added, on a continuous basis, from a stock that was 35.5% w/v of solids dissolved in water. Peristaltic pumps were used to deliver the carbon source at a feed rate of 0.4 grams of carbon per liter culture per hour. Operational parameters during both the batch and fed-batch portions of the run were: mixing by impeller agitation at 500 rpm, air sparging at 8 standard liters per minute, and a temperature of 28° C. Culture pH was maintained at 4.0-4.5 during batch growth and pH 3.5 during cellulase production using an automated controller connected to an online pH probe and a pump enabling the addition of a 10% ammonium hydroxide solution. Periodically, 100 mL samples of broth were drawn for biomass and protein analysis. After 96 hours of fermentation time 1L of fermentation media was collected and filtered for further protein analysis.

Initial Media for Fed-Batch Fermentations

| Component | Concentration, g/L |
|---|---|
| (NH$_4$)$_2$SO$_4$ | 2.20 |
| KH$_2$PO$_4$ | 1.39 |
| MgSO$_4$•7H$_2$O | 0.70 |
| CaCl$_2$•2H$_2$O | 0.185 |
| Dry Corn Steep Liquor | 6.00 |
| Glucose | 13.00 |
| Trace elements* | 0.38 mL/L |

*Trace elements solution contains 5 g/L FeSO$_4$•7H$_2$0; 1.6 g/L MnSO$_4$•H$_2$0; 1.4 g/L ZnSO$_4$•7H$_2$0.

Example 10

Hydrolysis of Beta-Glucan by *T. reesei* Enzyme Mixtures Comprising Parental and Modified TrCel6A Glycosidases.

Testing was performed on a Legacy Barley varietal from northern Saskatchewan. Solids 89.6%, ~60% starch, 10-14% NSP (non-starch polysaccharides).

Grain samples were ground to pass a 20 mesh screen using a Wiley Mill. Total carbohydrates were determined through acid hydrolysis and ion chromatography on a DX-500 system with PA1 column and amperometric detection. Total carbohydrates minus total starch was used to determine quantity of non-starch polysaccharides in the substrate in order to determine starting enzyme dose. Solids determination was used to correct for sample dry weights in all experiments.

Viscosity reduction by parental and modified Family 6 glycosidases was deteremined using a Perten SuperRVA4 can and paddle assembly, fixed retention time of 15 min, a 30 mL sample size at 35% solids, 50 mM citrate buffer, pH 4.5, and a temperature of 52° C. An initial sec mix at 900 rpm was followed by data collection at 4 sec intervals at 160 rpm. Data were collected in centepoise units (cP)

Samples were treated with dilute enzyme solutions of 1 mL based on a weight of protein per metric tonne of substrate. Viscosity reduction was calculated as a change from control over the last 1 minute of data collection. The results are presented in Tables 6 and 7.

A much greater reduction in viscosity of the barley beta-glucan substrate is achieved by the modified Family 6 glycosidase TrCel6A-W367G-S413P effects than by the wild type Family 6 glycosidase TrCel6A both when the Family 6 glycosidase is acting alone (Table 6) or in combination with other cellulases and hemicellulases (Table 7).

TABLE 6

Reduction of Barley beta-glucan viscosity by wild-type and modified Family 6 glycosidases

| Sample | Glycosidase Dose (mg protein/30 mL assay) | Viscosity relative to Untreated Sample[a] |
|---|---|---|
| Untreated | 0 | 1.0 |
| TrCel6A-W367G-S413 | 0.076 | 0.45 |
| TrCel6A (wild-type) | 0.076 | 0.70 |

TABLE 7

Reduction of Barley beta-glucan viscosity by cellulase-hemicellulase mixtures comprising wild-type and modified Family 6 glycosidases

| Sample | Ultimase XTP Dosage (mg protein/sample) | Glycosidase Dose (mg protein/30 mL assay) | Viscosity relative to Untreated Sample |
|---|---|---|---|
| Untreated | 0 | 0 | 1.0 |
| Ultimase XTP | 0.069 | 0 | 0.175 |
| Ultimase XTP[a] + TrCel6A-W367G-S413P | 0.069 | 0.036 | 0.14 |
| | 0.069 | 0.078 | 0.147 |
| Ultimase XTP[a] + TrCel6A (wild-type) | 0.069 | 0.036 | 0.17 |
| | 0.069 | 0.078 | 0.17 |

[a]Ultimase XTP is a commercial *Trichoderma reesei* whole cellulase with an enriched thermostable xylanase II component.

REFERENCES

Altschul et al. (1990) Basic local alignment search tool. *J. Mol. Biol.* 215:403-10

Butler, T. and Alcalde, M. (2003) In Methods in Molecular Biology, vol. 231: (F. H. Arnold and G. Georgiou, editors), Humana Press Inc. Totowa (N.J.), pages 17-22.

Coutinho, P. M. & Henrissat, B. (1999) "Carbohydrate-active enzymes: an integrated database approach." *In Recent Advances in Carbohydrate Bioengineering.* H. J. Gilbert, G. Davies, B. Henrissat and B. Svensson eds., The Royal Society of Chemistry, Cambridge, pp. 3-12.

Davies, et al. (2000) "Structure and function of *Humicola insolens* family 6 cellulases: structure of the endoglucanase, Cel6B, at 1.6 A resolution". Biochem. J. 348:201-207

Eijsink. V. G., et al. (2005) "Directed evolution of enzyme stability." Biomol. Eng. 22:21-30

Enari, T.-M., Knowles, J. K. C., Lehtinen, U., Nikkola, M., Penttila, M., Suihko, M.-L., Home, S., and A. Vilpola. (1987) "Glucanolytic brewer's yeast." *Proc. 2$^{st}$ Congr. Eur. Brew. Conv.* Madrid IRL Press, Oxford, pp. 529-536.

Gietz, R. D. and Woods, R. A. (2002) Transformation of yeast by the Liac/ss carrier DNA/PEG method. *In Methods in Enzymology,* 350:87-96.

Henriksson, K., Teleman, A., Suortti, T., Reinikainen, T., Jaskari, J., Teleman, O., and K. Poutanen. (1995) "Hydrolysis of barley (1→3), (1→4)-β-D-glucan by a cellobiohydrolase II preparation from *Trichoderma reesei.*" *Carbohydrate Polymers* 26, 109-119.

Koivula, A., Ruohonen, L., Wohlfahrt, G., Reinikainen, T., Teeri, T. T., Piens, K., Claeyssens, M., Weber, M., Vasella, A., Becker, D., Sinnott, M. L., Zou, J. Y., Kleywegt, G. J., Szardenings, M., Stahlberg, J., and T. A. Jones. (2002) "The active site of cellobiohydrolase Cel6A from *Trichoderma reesei*: the roles of aspartic acids D221 and D175." *J Am Chem Soc.* 124, 10015-24.

Koivula, A., Kinnari, T., Harjunpaa, V., Ruohonen, L., Teleman, A., Drakenberg, T., Rouvinen, J., Jones, T. A., and T. T. Teeri. (1999) "Tryptophan 272: an essential determinant of crystalline cellulose degradation by *Trichoderma reesei* cellobiohydrolase Cel6A." *FEBS Lett.* 429, 341-6.

Koivula, A., Reinikainen, T., Ruohonen, L., Valkeajarvi, A., Claeyssens, M., Teleman, O., Kleywegt, G. J., Szardenings, M., Rouvinen, J., Jones, T. A., and T. T. Teeri. (1996) "The active site of *Trichoderma reesei* cellobiohydrolase II: the role of tyrosine 169." Protein Eng. 9, 691-9.

Meinke, A., Damude, H. G., Tomme, P., Kwan, E., Kilburn, D. G., Miller, R.C. Jr., Warren, R. A., and N. R. Gilkes. (1995) "Enhancement of the endo-beta-1,4-glucanase activity of an exocellobiohydrolase by deletion of a surface loop." *J Biol Chem.* 270, 4383-6.

Rouvinen, J. et al. (1990) "Three-dimensional structure of cellobiohydrolase II from I." Science 249:380-386. Erratum in: Science 1990 249:1359

Spezio, M. et al. (1993) "Crystal structure of the catalytic domain of a thermophilic endocellulase". Biochemistry 32:9906-9916

Tao, H. and Cornish, V. W (2002) "Milestones in Directed Enzyme Evolution." *Curr Opin Chem Biol* 6: 858-864.

Tansey, M. R. (1971) Agar-Diffusion Assay of Cellulolytic Ability of Thermophilic Fungi. *Arch. Mikrobiol,* 77:1-11.

Trinder, P. (1969) Determination of glucose in blood using glucose oxidase with an alternative oxygen accepter. *Annals of Clinical Biochemistry,* 6:24-27.

Varrot, A., et al. (1999) "Crystal structure of the catalytic core domain of the family 6 cellobiohydrolase II, Cel6A, from *Humicola insolens*, at 1.92 A resolution". Biochem J. Varrot, A., Frandsen, T.P., Driguez, H., and G. J. Davies. (2002) "Structure of the *Humicola insolens* cellobiohydrolase Cel6A D416A mutant in complex with a non-hydrolysable substrate analogue, methyl cellobiosyl-4-thio-beta-cellobioside, at 1.9 A." *Acta C ystallogr D Biol C ystallogr.* 58, 2201-4.

Varrot, A. et al. (2005) "*Mycobacterium tuberculosis* strains possess functional cellulases". J. Biol. Chem. 280:20181-20184

Wohlfahrt, G., Pellikka, T., Boer, H., Teeri, T. T., and A. Koivula. (2003) "Probing pH-dependent functional elements in proteins: modification of carboxylic acid pairs in *Trichoderma reesei* cellobiohydrolase Cel6A." *Biochemistry.* 42, 10095-103.

Zhang, S., Irwin, D. C., and D. B. Wilson. (2000a) "Site-directed mutation of noncatalytic residues of *Thermobifidia fusca* exocellulase Cel6B." *Eur J Biochem.* 267, 3101-15.

Zhang, S., Barr, B. K., and D. B. Wilson. (2000b) "Effects of noncatalytic residue mutations on substrate specificity and ligand binding of *Thermobifida fusca* endocellulase cel6A." Eur J Biochem. 267, 244-52.

Zou, J., Kleywegt, G. J., Stahlberg, J., Driguez, H., Nerinckx, W., Claeyssens, M., Koivula, A., Teeri, T. T., and T. A. Jones. (1999) "Crystallographic evidence for substrate ring distortion and protein conformational changes during catalysis in cellobiohydrolase Cel6A from *Trichoderma reesei.*" Structure

The embodiments of the invention in which an exclusive property or privilege is claimed are defined as follows:

1. A modified Family 6 glycosidase comprising an amino acid substitution at position 367 selected from the group consisting of W367G, W367A, W367C, W367N, W367R, W367S, W367T, and W367V, said position determined from alignment of a parental Family 6 glycosidase amino acid sequence with a *Trichoderma reesei* Cel6A amino acid sequence as defined in SEQ ID NO: 1, wherein amino acids 83-447 (TrCel6A numbering) of said modified Family 6 glycosidase are from about 90% to about 99.9% identical to amino acids 83-447 of SEQ ID NO: 1 and wherein said modified Family 6 glycosidase exhibits at least a 1.2-fold increase in hydrolysis activity of beta 1-3, 1-4 -linked polysaccharides and at least a three-fold decrease in hydrolysis activity of beta 1-4 linked polysaccharides, compared with said parental Family 6 glycosidase from which said modified Family 6 glycosidase is derived.

2. A modified Family 6 glycosidase comprising amino acid substitution selected W367G, said position determined from alignment of a parental Family 6 glycosidase amino acid sequence with a *Trichoderma reesei* Cel6A amino acid sequence as defined in SEQ ID NO: 1, wherein amino acids 83-447 (TrCel6A numbering) of said modified Family 6 glycosidase are from about 90% to about 99.9% identical to amino acids 83-447 (TrCel6A numbering) of SEQ ID NO: 1, and wherein said isolated Family 6 glycosidase exhibits at least a 1.2-fold increase in hydrolysis activity of beta 1-3, 1-4 -linked polysaccharides and at least a three-fold decrease in hydrolysis activity of beta 1-4 linked polysaccharides, compared with said parental Family 6 glycosidase from which said modified Family 6 glycosidase is derived.

3. The isolated Family 6 glycosidase of claim 1, wherein said modified Family 6 glycosidase exhibits at least a 1.2-fold decrease in hydrolysis activity of beta 1-4-linked polysaccharides compared with the hydrolysis activity of a parental Family 6 glycosidase from which said modified Family 6 glycosidase is derived.

4. The isolated Family 6 glycosidase of claim 2, wherein said modified Family 6 glycosidase exhibits at least a 1.2-fold decrease in hydrolysis activity of beta 1-4-linked polysaccharides compared with the hydrolysis activity of a parental Family 6 glycosidase from which said modified Family 6 glycosidase is derived.

5. The isolated Family 6 glycosidase of claim 2, wherein amino acids 83-447 (TrCel6A numbering) of said isolated Family 6 glycosidase are from about 95% to about 99.9% identical to amino acids 83-447 (TrCle6A numbering) of SEQ ID NO: 1.

6. The isolated Family 6 glycosidase of claim 1, further comprising at least one amino acid substitution selected from the group consisting of N182S, N182R, N182G, N182A, E399H, E399S, E399T, C400V, C400M, C400T, C400S, A427V, A427L, and A427S.

7. The isolated Family 6 glycosidase of claim 2, further comprising at least one amino acid substitutions selected from the group consisting of N182S, N182R, N182G, N182A, E399H, E399S, E399T, C400V, C400M, C400T, C400S, A427V, A427L, and A427S.

8. A process for producing a Family 6 glycosidase comprising the steps of growing an isolated genetically modified microbe harboring a genetic construct comprising a nucleic acid sequence encoding the Family 6 glycosidase according to claim 1, in a culture medium under conditions that induce the expression and secretion of the Family 6 glycosidase and recovering the Family 6 glycosidase from the culture medium.

9. A process for producing a Family 6 glycosidase, comprising the steps of growing an isolated genetically modified microbe harboring a genetic construct comprising a nucleic acid sequence encoding the Family 6 glycosidase according to claim 2, in a culture medium under conditions that induce the expression and secretion of the modified Family 6 glycosidase and recovering the Family 6 glycosidase from the culture medium.

10. A process for hydrolyzing a beta-1,3-1,4-linked polysaccharide substrate comprising contacting said substrate with the isolated Family 6 glycosidase of claim 1.

11. A process for hydrolyzing a beta-1,3-1,4-linked polysaccharide substrate comprising contacting said substrate with the isolated Family 6 glycosidase of claim 2.

12. The process of claim 10, wherein said beta-1,3-1,4-linked polysaccharide substrate is a constituent of a cereal grain.

13. The process of claim 11, wherein said beta-1,3-1,4-linked polysaccharide substrate is a constituent of a cereal grain.

14. The process of claim 12, wherein said process is part of an industrial process to produce alcohol, animal feed or food products.

15. The process of claim 13, wherein said process is part of an industrial process to produce alcohol, animal feed or food products.

16. A process for producing a Family 6 glycosidase comprising the steps of; (i) transforming fungal host cells with a genetic construct encoding the isolated Family 6 glycosidase of claim 1 to produce recombinant fungal strains; (ii) selecting the recombinant fungal strains expressing the Family 6 glycosidase; and (iii) culturing selected recombinant strains by submerged liquid fermentations under conditions that induce expression of the Family 6 glycosidase.

17. A process for producing a Family 6 glycosidase, comprising the steps of; (i) transforming fungal host cells with a genetic construct encoding the isolated Family 6 glycosidase of claim 6 to produce recombinant fungal strains; (ii) selecting the recombinant fungal strains expressing the Family 6 glycosidase; and (iii) culturing selected recombinant strains by submerged liquid fermentations under conditions that induce expression of the modified Family 6 glycosidase.

18. A isolated Family 6 glycosidase comprising amino acid sequence TrCel6A-W367G-S413P (SEQ ID NO: 39).

* * * * *

UNITED STATES PATENT AND TRADEMARK OFFICE
CERTIFICATE OF CORRECTION

| | | |
|---|---|---|
| PATENT NO. | : 8,263,379 B2 | |
| APPLICATION NO. | : 12/504070 | |
| DATED | : September 11, 2012 | |
| INVENTOR(S) | : John Tomashek et al. | |

It is certified that error appears in the above-identified patent and that said Letters Patent is hereby corrected as shown below:

ON THE TITLE PAGE [56] REFERENCES CITED:

Other Publications, under Davies et al., "Humicola insolens" should read
--*Humicola insolens*--.

ON THE TITLE PAGE [57] ABSTRACT:

Line 4, "form" should read --from--.

COLUMN 3:

Line 36, "substitution" should read --substitutions--.

COLUMN 5:

Line 49, "cellulose" should read --cellulose.--.

COLUMN 6:

Line 21, "YEp/PGK-αss" should read --YEp/PGK- $α_{ss}$--; and
Line 25, "PGK-αss-NKE-HiAvi2" should read --PGK-$α_{ss}$-NKE-HiAvi2--.

COLUMN 7:

Line 13, "if" should read --if it--; and
Line 25, "alphabeta-barrel" should read --alpha/beta barrel--.

Signed and Sealed this
Twenty-fifth Day of December, 2012

David J. Kappos
*Director of the United States Patent and Trademark Office*

CERTIFICATE OF CORRECTION (continued)

COLUMN 9:

Line 13, ";URL:blast.ncbi.nlm.nih.gove/" should be deleted;
Line 14, ""Blast.chi" should be deleted; and
Line 16, "(URL:ebi.cak.ak/Tools/clustalw2/index.html)" should be deleted.

COLUMN 11:

Line 10, "wild type" should read --wild-type--; and
Line 15, "wild type" (both occurrences) should read --wild-type--; and
Line 16, "wild type" should read --wild-type--.

COLUMN 12:

Line 9, "Table 2" should read --Table 2.--.

COLUMN 13:

Line 37, "*Hansen ula,*" should read --*Hansenula*,--;
Line 41, "*Typi-*" should be Roman Type;
Line 42, all text should be Roman Type; and
Line 43, "*any or all Family*" should be Roman Type.

COLUMN 14:

Line 4, "substitution" should read --substitutions--.

COLUMN 15:

Line 52, "YEpFLΔGAKpn" should read --YEpFLAGΔKpn--.

COLUMN 16:

Line 30, "YEp352/PGK91-1>NheI-" should read --YEp352/PGK91-1ΔNheI- --;
Line 36, "transfor ation" should read --transformation--;
Line 37, "YEep/PGK-alphass-NKE:" should read --YEp/PGK-alpha$_{ss}$-NKE:--;
Line 52, "PcCel6A-W36G" should read --PcCel6A-W36lG--;
Line 53, "Pccel6a" should read --PcCel6A--;
Line 55, "3'VHO99.Pccel6a" should read --3'VH099.PcCel6A--; and
Line 56, "NheIlKpnI" should read --NheI/KpnI--.

COLUMN 17:

Line 21, "NheIlKpnI" should read --NheI/KpnI--;
Line 50, "a" (2nd occurrence) should read --an--; and Line 52, "were" should read --was--.

COLUMN 19:

Line 46, "YEp352/PGK91-1ΔheI" should read --YEp352/PGK91-1ΔNheI--.

COLUMN 20:

Line 3, "YEp352/PGK91-1ΔheI" should read --YEp352/PGK91-1ΔNheI--.

COLUMN 21:

Line 32, "3,5-Dinitosalicylic" should read --3,5-Dinitrosalicylic--;
Line 58, "A." should read --*A.*--; and
Line 59, "niger" should read --*niger*--.

COLUMN 23:

Line 10, "Nhe1-Sph1-Not1" should read --NheI-SphI-NotI--;
Line 43, "a Sma1" should read --an SmaI--; and
Line 46, "Sma1" should read --SmaI--.

COLUMN 24:

Line 50, "AmPR" should read --Amp$^R$--;
Line 59, "over" should read --other--; and
Line 65, "Apa1" should read --ApaI--.

COLUMN 25:

Line 22, "Wild Type" should read --Wild-Type--; and
Line 24, "wild type" should read --wild-type--.

COLUMN 26:

Line 44, "media" (second occurrence) should be deleted; and
Line 47, "grinded" should read --ground--.

COLUMN 27:

Line 15, "wild type" should read --wild-type--; and
Line 67, "wild type" should read --wild-type--.

COLUMN 28:

Line 19, "MgSO₄-7H2O" should read --MgSO$_4$-7H$_2$O--;
Line 21, "FeSO₄-7H2O" should read --FeSO$_4$-7H$_2$O--; and
Line 19, "MnSO₄-7H2O" should read --MnSO$_4$-7H$_2$O--.

COLUMN 30:

Line 32, "wild" should read --wild- --; and
Line 42, "Samplea" should read --Sample--.

COLUMN 32:

Line 7, "1990 249:1359" should read --1990 249:1359.--;
Line 20, "Biochem J. Var-" should read --Biochem J. 337:297-304.--;
Line 21, "rot, A.," should read --Varrot, A.,--;
Line 25, "C ystallogr D Biol C" should read --*Crystallography*--; and
Line 26, "*ystallogr.*" should be deleted.

COLUMN 169:

Line 42, "A modified" should read --An isolated--;
Line 53, "modified" should read --isolated--;
Line 57, "said modified" should read --the isolated--; and
Line 59, "A modified" should read --An isolated--.

COLUMN 170:

Line 44, "said modified" should read --the isolated--;
Line 46, "modified" should read --isolated--;
Line 49, "modified" should read --isolated--;
Line 53, "modified" should read --isolated--;
Line 55, "a" should read --said--; and
Line 56, "modified" should read --isolated--.

COLUMN 171:

Line 2, "substitutions" should read --substitution--.

COLUMN 172:

Line 4, "is part of" should read --comprises--;
Line 5, "to produce" should read --producing--;
Line 7, "is part of" should read --comprises--;
Line 8, "to produce" should read --producing--;

Line 15, "culturing" should read --culturing said--; and
Line 16, "fermentations" should read --fermentation--.

```
SEQUENCE LISTING

<160> NUMBER OF SEQ ID NOS: 96

<210> SEQ ID NO 1
<211> LENGTH: 447
<212> TYPE: PRT
<213> ORGANISM: Trichoderma reesei

<400> SEQUENCE: 1

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45
```

```
Arg Ala Ala Ser Thr Thr Ser Arg Val Ser Pro Thr Thr Ser Arg Ser
 50                  55                  60

Ser Ser Ala Thr Pro Pro Gly Ser Thr Thr Thr Arg Val Pro Pro
65                   70                  75                  80

Val Gly Ser Gly Thr Ala Thr Tyr Ser Gly Asn Pro Phe Val Gly Val
                 85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 2
<211> LENGTH: 362
<212> TYPE: PRT
```

-continued

<213> ORGANISM: Hypocrea koningii

<400> SEQUENCE: 2

| | | | | | | | | | | | | | | |
|---|---|---|---|---|---|---|---|---|---|---|---|---|---|---|
| Ala | Thr | Tyr | Ser | Gly | Asn | Pro | Phe | Val | Gly | Thr | Pro | Trp | Ala | Asn |
| 1 | | | | 5 | | | | | 10 | | | | | 15 |
| Ala | Tyr | Tyr | Ala | Ser | Glu | Val | Ser | Ser | Leu | Ala | Ile | Pro | Ser | Leu | Thr |
| | | | 20 | | | | | 25 | | | | | 30 | | |
| Gly | Ala | Met | Ala | Thr | Ala | Ala | Ala | Val | Ala | Lys | Val | Pro | Ser | Phe |
| | | 35 | | | | 40 | | | | | 45 | | | |
| Met | Trp | Leu | Asp | Thr | Leu | Asp | Lys | Thr | Pro | Leu | Met | Glu | Gln | Thr | Leu |
| | 50 | | | | | 55 | | | | | 60 | | | | |
| Ala | Asp | Ile | Arg | Thr | Ala | Asn | Lys | Asn | Gly | Gly | Asn | Tyr | Ala | Gly | Gln |
| 65 | | | | | 70 | | | | | 75 | | | | | 80 |
| Phe | Val | Val | Tyr | Asp | Leu | Pro | Asp | Arg | Asp | Cys | Ala | Ala | Leu | Ala | Ser |
| | | | | 85 | | | | | 90 | | | | | 95 | |
| Asn | Gly | Glu | Tyr | Ser | Ile | Ala | Asp | Gly | Gly | Val | Ala | Lys | Tyr | Lys | Asn |
| | | | 100 | | | | | 105 | | | | | 110 | | |
| Tyr | Ile | Asp | Thr | Ile | Arg | Gln | Ile | Val | Val | Glu | Tyr | Ser | Asp | Ile | Arg |
| | | | 115 | | | | | 120 | | | | | 125 | | |
| Thr | Leu | Leu | Val | Ile | Glu | Pro | Asp | Ser | Leu | Ala | Asn | Leu | Val | Thr | Asn |
| | 130 | | | | | 135 | | | | | 140 | | | | |
| Leu | Gly | Thr | Pro | Lys | Cys | Ala | Asn | Ala | Gln | Ser | Ala | Tyr | Leu | Glu | Cys |
| 145 | | | | | 150 | | | | | 155 | | | | | 160 |
| Ile | Asn | Tyr | Ala | Val | Thr | Gln | Leu | Asn | Leu | Pro | Asn | Val | Ala | Met | Tyr |
| | | | | 165 | | | | | 170 | | | | | 175 | |
| Leu | Asp | Ala | Gly | His | Ala | Gly | Trp | Leu | Gly | Trp | Pro | Ala | Asn | Gln | Asp |
| | | | 180 | | | | | 185 | | | | | 190 | | |
| Pro | Ala | Ala | Gln | Leu | Phe | Ala | Asn | Val | Tyr | Lys | Asn | Ala | Ser | Ser | Pro |
| | | 195 | | | | | 200 | | | | | 205 | | | |
| Arg | Ala | Leu | Arg | Gly | Leu | Ala | Thr | Asn | Val | Ala | Asn | Tyr | Asn | Gly | Trp |
| | 210 | | | | | 215 | | | | | 220 | | | | |
| Asn | Ile | Thr | Ser | Pro | Pro | Ser | Tyr | Thr | Gln | Gly | Asn | Ala | Val | Tyr | Asn |
| 225 | | | | | 230 | | | | | 235 | | | | | 240 |
| Glu | Lys | Leu | Tyr | Ile | His | Ala | Ile | Gly | Arg | Leu | Leu | Ala | Asn | His | Gly |
| | | | | 245 | | | | | 250 | | | | | 255 | |
| Trp | Ser | Asn | Ala | Phe | Phe | Ile | Thr | Asp | Gln | Gly | Arg | Ser | Gly | Lys | Gln |
| | | | | 260 | | | | | 265 | | | | | 270 | |
| Pro | Thr | Gly | Gln | Gln | Gln | Trp | Gly | Asp | Trp | Cys | Asn | Val | Ile | Gly | Thr |
| | | 275 | | | | | 280 | | | | | 285 | | | |
| Gly | Phe | Gly | Ile | Arg | Pro | Ser | Ala | Asn | Thr | Gly | Asp | Ser | Leu | Leu | Asp |
| | | 290 | | | | | 295 | | | | | 300 | | | |
| Ser | Phe | Val | Trp | Val | Lys | Pro | Gly | Gly | Glu | Cys | Asp | Gly | Thr | Ser | Asp |
| 305 | | | | | 310 | | | | | 315 | | | | | 320 |
| Ser | Ser | Ala | Pro | Arg | Phe | Asp | Ser | His | Cys | Ala | Leu | Pro | Asp | Ala | Leu |
| | | | | 325 | | | | | 330 | | | | | 335 | |
| Gln | Pro | Ala | Pro | Gln | Ala | Gly | Ala | Trp | Phe | Gln | Ala | Tyr | Phe | Val | Gln |
| | | | 340 | | | | | 345 | | | | | 350 | | |
| Leu | Leu | Thr | Asn | Ala | Asn | Pro | Ser | Phe | Leu |
| | | | 355 | | | | | 360 | |

<210> SEQ ID NO 3
<211> LENGTH: 362
<212> TYPE: PRT
<213> ORGANISM: Trichoderma viride CICC 13038

<400> SEQUENCE: 3

Ala Thr Tyr Ser Gly Asn Pro Phe Val Gly Val Thr Pro Trp Ala Asn
1               5                   10                  15

Ala Tyr Tyr Ala Ser Glu Val Ser Ser Leu Ala Ile Pro Ser Leu Thr
            20                  25                  30

Gly Ala Met Ala Thr Ala Ala Ala Val Ala Lys Val Pro Ser Phe
        35                  40                  45

Met Trp Leu Asp Thr Leu Asp Lys Thr Pro Leu Met Glu Gln Thr Leu
50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Ala Lys Tyr Lys Asn
            100                 105                 110

Tyr Ile Asp Thr Ile Arg Gln Ile Val Val Glu Tyr Ser Asp Ile Arg
        115                 120                 125

Thr Leu Leu Val Ile Glu Pro Asp Ser Leu Ala Asn Leu Val Thr Asn
130                 135                 140

Leu Gly Thr Pro Lys Cys Ala Asn Ala Pro Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Gly Trp
210                 215                 220

Asn Ile Thr Ser Pro Pro Ser Tyr Thr Gln Gly Asn Ala Val Tyr Asn
225                 230                 235                 240

Glu Lys Leu Tyr Ile His Ala Ile Gly Pro Leu Leu Ala Asn His Gly
                245                 250                 255

Trp Ser Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
        275                 280                 285

Gly Phe Gly Ile Arg Pro Ser Ala Asn Thr Gly Asp Ser Leu Leu Asp
290                 295                 300

Ser Phe Val Trp Val Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
            340                 345                 350

Leu Leu Thr Asn Ala Asn Pro Ser Phe Leu
        355                 360

<210> SEQ ID NO 4
<211> LENGTH: 362
<212> TYPE: PRT
<213> ORGANISM: Hypocrea koningii 3.2774

<400> SEQUENCE: 4

Ala Thr Tyr Ser Gly Asn Pro Phe Val Gly Val Thr Pro Trp Ala Asn
1               5                   10                  15

Ala Tyr Tyr Ala Ser Glu Val Ser Ser Leu Ala Ile Pro Ser Leu Thr
            20                  25                  30

Gly Ala Met Ala Thr Ala Ala Ala Val Lys Val Pro Ser Phe
        35                  40                  45

Met Trp Leu Asp Thr Phe Asp Lys Thr Pro Leu Met Glu Gln Thr Leu
 50                  55                  60

Ala Asp Ile Arg Thr Ala Asn Lys Asn Gly Gly Asn Tyr Ala Gly Gln
 65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Asp Lys Tyr Lys Asn
            100                 105                 110

Tyr Ile Asp Thr Ile Arg Gln Ile Val Val Glu Tyr Ser Asp Ile Arg
            115                 120                 125

Thr Leu Leu Val Ile Glu Pro Asp Ser Leu Ala Asn Leu Val Thr Asn
130                 135                 140

Leu Gly Thr Pro Lys Cys Ala Asn Ala Gln Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Gly Trp
210                 215                 220

Asn Ile Thr Ser Pro Pro Ser Tyr Thr Gln Gly Asn Ala Val Tyr Asn
225                 230                 235                 240

Glu Gln Leu Tyr Ile His Ala Ile Gly Pro Leu Leu Ala Asn His Gly
                245                 250                 255

Trp Ser Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
        275                 280                 285

Gly Phe Gly Ile Arg Pro Ser Ala Asn Thr Gly Asp Ser Leu Leu Asp
290                 295                 300

Ser Phe Val Trp Ile Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
            340                 345                 350

Leu Leu Thr Asn Ala Asn Pro Ser Phe Leu
        355                 360

<210> SEQ ID NO 5
<211> LENGTH: 362
<212> TYPE: PRT
<213> ORGANISM: Hypocrea koningii AS3.2774

<400> SEQUENCE: 5

Ala Thr Tyr Ser Gly Asn Pro Phe Val Gly Val Thr Pro Trp Ala Asn
1               5                   10                  15

Ala Tyr Tyr Ala Ser Glu Val Ser Ser Leu Ala Ile Pro Ser Leu Thr
            20                  25                  30

```
Gly Ala Met Ala Thr Ala Ala Ala Val Ala Lys Val Pro Ser Ser
            35                  40                  45

Met Trp Leu Asp Thr Phe Asp Lys Thr Pro Leu Met Glu Gln Thr Leu
 50                  55                  60

Ala Asp Ile Arg Thr Ala Asn Lys Asn Gly Asn Tyr Ala Gly Gln
 65                  70                  75                  80

Phe Val Val Tyr Asp Leu Pro Asp Arg Asp Cys Ala Ala Leu Ala Ser
                    85                  90                  95

Asn Gly Glu Tyr Ser Ile Ala Asp Gly Gly Val Asp Lys Tyr Lys Asn
                100                 105                 110

Tyr Ile Asp Thr Ile Arg Gln Ile Val Val Glu Tyr Ser Asp Ile Arg
                115                 120                 125

Thr Leu Leu Val Ile Glu Pro Asp Ser Leu Ala Asn Leu Val Thr Asn
                130                 135                 140

Leu Gly Thr Pro Lys Cys Ala Asn Ala Gln Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
                180                 185                 190

Pro Ala Ala Gln Leu Phe Ala Asn Val Tyr Lys Asn Ala Ser Ser Pro
                195                 200                 205

Arg Ala Leu Arg Gly Leu Ala Thr Asn Val Ala Asn Tyr Asn Gly Trp
210                 215                 220

Asn Ile Thr Ser Pro Pro Ser Tyr Thr Gln Gly Asn Ala Val Tyr Asn
225                 230                 235                 240

Glu Gln Leu Tyr Ile His Ala Ile Gly Pro Leu Leu Ala Asn His Gly
                245                 250                 255

Trp Ser Asn Ala Phe Phe Ile Thr Asp Gln Gly Arg Ser Gly Lys Gln
                260                 265                 270

Pro Thr Gly Gln Gln Gln Trp Gly Asp Trp Cys Asn Val Ile Gly Thr
                275                 280                 285

Gly Phe Gly Ile Arg Pro Ser Ala Asn Thr Gly Asp Ser Leu Leu Asp
                290                 295                 300

Ser Phe Val Trp Ile Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
                340                 345                 350

Leu Leu Thr Asn Ala Asn Pro Ser Phe Leu
                355                 360

<210> SEQ ID NO 6
<211> LENGTH: 362
<212> TYPE: PRT
<213> ORGANISM: Trichoderma parceramosum

<400> SEQUENCE: 6

Ala Thr Tyr Ser Gly Asn Pro Phe Val Gly Val Thr Pro Trp Ala Asn
 1               5                  10                  15

Ala Tyr Tyr Ala Ser Glu Val Ser Ser Leu Ala Ile Pro Ser Leu Thr
                20                  25                  30

Gly Ala Met Ala Thr Ala Ala Ala Val Ala Lys Val Pro Ser Phe
            35                  40                  45
```

Met Trp Leu Asp Thr Leu Asp Lys Thr Pro Leu Met Glu Gln Thr Leu
    50                  55                  60

Ala Asp Ile Arg Thr Ala Asn Lys Asn Gly Gly Asn Tyr Ala Gly Gln
65                  70                  75                  80

Phe Val Val Tyr Asp Leu Pro Asp Arg Asp Cys Ala Ala Leu Ala Ser
                85                  90                  95

Asn Gly Glu Tyr Ser Ile Ala Asp Gly Gly Val Ala Lys Tyr Lys Asn
                100                 105                 110

Tyr Ile Asp Thr Ile Arg Gln Ile Val Val Glu Tyr Ser Asp Ile Arg
            115                 120                 125

Thr Ile Leu Val Ile Glu Pro Asp Ser Leu Ala Asn Leu Val Thr Asn
    130                 135                 140

Leu Gly Thr Pro Lys Cys Ala Asn Ala Gln Ser Ala Tyr Leu Glu Cys
145                 150                 155                 160

Ile Asn Tyr Ala Ile Thr Gln Leu Asn Leu Pro Asn Ile Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
    195                 200                 205

Ser Ala Leu Arg Gly Leu Ala Thr Asn Val Ala Asn Tyr Asn Gly Trp
210                 215                 220

Asn Ile Thr Ser Pro Pro Ser Tyr Thr Gln Gly Asn Ala Val Tyr Asn
225                 230                 235                 240

Glu Lys Leu Tyr Ile His Ala Ile Gly Pro Leu Leu Ala Asn His Gly
                245                 250                 255

Trp Ser Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
    275                 280                 285

Gly Phe Gly Ile Arg Pro Ser Ser Asn Thr Gly Asp Ser Leu Leu Asp
290                 295                 300

Ser Phe Val Trp Val Lys Pro Gly Gly Glu Cys Asp Gly Thr Ser Asp
305                 310                 315                 320

Ser Ser Ala Pro Arg Phe Asp Ser His Cys Ala Leu Pro Asp Ala Leu
                325                 330                 335

Gln Pro Ala Pro Gln Ala Gly Ala Trp Phe Gln Ala Tyr Phe Val Gln
            340                 345                 350

Leu Leu Thr Asn Ala Asn Pro Ser Phe Leu
        355                 360

<210> SEQ ID NO 7
<211> LENGTH: 365
<212> TYPE: PRT
<213> ORGANISM: Aspergillus nidulans FGSC A4

<400> SEQUENCE: 7

Ala Thr Ala Ser Gly Asn Pro Phe Ser Gly Tyr Gln Leu Tyr Val Asn
1               5                   10                  15

Pro Tyr Tyr Ser Ser Glu Val Gln Ser Ile Ala Ile Pro Ser Leu Thr
                20                  25                  30

Gly Thr Leu Ser Ser Leu Ala Pro Ala Thr Ala Ala Ala Lys Val
            35                  40                  45

Pro Ser Phe Val Trp Leu Asp Val Ala Ala Lys Val Pro Thr Met Ala
    50                  55                  60

```
Thr Tyr Leu Ala Asp Ile Arg Ser Gln Asn Ala Ala Gly Ala Asn Pro
 65                  70                  75                  80

Pro Ile Ala Gly Gln Phe Val Val Tyr Asp Leu Pro Asp Arg Asp Cys
                 85                  90                  95

Ala Ala Leu Ala Ser Asn Gly Glu Phe Ala Ile Ser Asp Gly Gly Val
            100                 105                 110

Gln His Tyr Lys Asp Tyr Ile Asp Ser Ile Arg Glu Ile Leu Val Glu
        115                 120                 125

Tyr Ser Asp Val His Val Ile Leu Val Ile Glu Pro Asp Ser Leu Ala
130                 135                 140

Asn Leu Val Thr Asn Leu Asn Val Ala Lys Cys Ala Asn Ala Gln Ser
145                 150                 155                 160

Ala Tyr Leu Glu Cys Thr Asn Tyr Ala Val Thr Gln Leu Asn Leu Pro
                165                 170                 175

Asn Val Ala Met Tyr Leu Asp Ala Gly His Ala Gly Trp Leu Gly Trp
            180                 185                 190

Pro Ala Asn Leu Gln Pro Ala Ala Asn Leu Tyr Ala Gly Val Tyr Ser
        195                 200                 205

Asp Ala Gly Ser Pro Ala Ala Leu Arg Gly Leu Ala Thr Asn Val Ala
    210                 215                 220

Asn Tyr Asn Ala Trp Ala Ile Asp Thr Cys Pro Ser Tyr Thr Gln Gly
225                 230                 235                 240

Asn Ser Val Cys Asp Glu Lys Asp Tyr Ile Asn Ala Leu Ala Pro Leu
                245                 250                 255

Leu Arg Ala Gln Gly Phe Asp Ala His Phe Ile Thr Asp Thr Gly Arg
            260                 265                 270

Asn Gly Lys Gln Pro Thr Gly Gln Gln Ala Trp Gly Asp Trp Cys Asn
        275                 280                 285

Val Ile Gly Thr Gly Phe Gly Ala Arg Pro Ser Thr Asn Thr Gly Asp
    290                 295                 300

Ser Leu Leu Asp Ala Phe Val Trp Val Lys Pro Gly Gly Glu Ser Asp
305                 310                 315                 320

Gly Thr Ser Asp Thr Ser Ala Ala Arg Tyr Asp Ala His Cys Gly Tyr
                325                 330                 335

Ser Asp Ala Leu Gln Pro Ala Pro Glu Ala Gly Thr Trp Phe Gln Ala
            340                 345                 350

Tyr Phe Val Gln Leu Leu Gln Asn Ala Asn Pro Ser Phe
        355                 360                 365

<210> SEQ ID NO 8
<211> LENGTH: 365
<212> TYPE: PRT
<213> ORGANISM: Aspergillus niger CBS 513.88

<400> SEQUENCE: 8

Ala Ser Ala Ser Gly Asn Pro Phe Ser Gly Tyr Gln Leu Tyr Val Asn
 1               5                  10                  15

Pro Tyr Tyr Ser Ser Glu Val Ala Ser Leu Ala Ile Pro Ser Leu Thr
                 20                  25                  30

Gly Ser Leu Ser Ser Leu Gln Ala Ala Thr Ala Ala Ala Lys Val
             35                  40                  45

Pro Ser Phe Val Trp Leu Asp Thr Ala Ala Lys Val Pro Thr Met Gly
         50                  55                  60

Asp Tyr Leu Ala Asp Ile Gln Ser Gln Asn Ala Ala Gly Ala Asn Pro
 65                  70                  75                  80
```

```
Pro Ile Ala Gly Gln Phe Val Val Tyr Asp Leu Pro Arg Asp Cys
                85                  90                  95

Ala Ala Leu Ala Ser Asn Gly Glu Tyr Ser Ile Ala Asp Asn Gly Val
            100                 105                 110

Glu His Tyr Lys Ser Tyr Ile Asp Ser Ile Arg Glu Ile Leu Val Gln
            115                 120                 125

Tyr Ser Asp Val His Thr Leu Leu Val Ile Glu Pro Asp Ser Leu Ala
130                 135                 140

Asn Leu Val Thr Asn Leu Asn Val Ala Lys Cys Ala Asn Ala Glu Ser
145                 150                 155                 160

Ala Tyr Leu Glu Cys Thr Asn Tyr Ala Leu Thr Gln Leu Asn Leu Pro
                165                 170                 175

Asn Val Ala Met Tyr Leu Asp Ala Gly His Ala Gly Trp Leu Gly Trp
            180                 185                 190

Pro Ala Asn Gln Gln Pro Ala Ala Asp Leu Phe Ala Ser Val Tyr Lys
            195                 200                 205

Asn Ala Ser Ser Pro Ala Ala Val Arg Gly Leu Ala Thr Asn Val Ala
210                 215                 220

Asn Tyr Asn Ala Trp Thr Ile Ser Ser Cys Pro Ser Tyr Thr Gln Gly
225                 230                 235                 240

Asn Ser Val Cys Asp Glu Gln Gln Tyr Ile Asn Ala Ile Ala Pro Leu
                245                 250                 255

Leu Gln Ala Gln Gly Phe Asp Ala His Phe Ile Val Asp Thr Gly Arg
            260                 265                 270

Asn Gly Lys Gln Pro Thr Gly Gln Gln Ala Trp Gly Asp Trp Cys Asn
            275                 280                 285

Val Ile Asn Thr Gly Phe Gly Arg Pro Thr Thr Thr Gly Asp
290                 295                 300

Ala Leu Val Asp Ala Phe Val Trp Val Lys Pro Gly Gly Glu Ser Asp
305                 310                 315                 320

Gly Thr Ser Asp Ser Ser Ala Thr Arg Tyr Asp Ala His Cys Gly Tyr
                325                 330                 335

Ser Asp Ala Leu Gln Pro Ala Pro Glu Ala Gly Thr Trp Phe Gln Ala
            340                 345                 350

Tyr Phe Val Gln Leu Leu Thr Asn Ala Asn Pro Ala Phe
            355                 360                 365

<210> SEQ ID NO 9
<211> LENGTH: 362
<212> TYPE: PRT
<213> ORGANISM: Aspergillus oryzae RIB 40

<400> SEQUENCE: 9

Ala Thr Ala Gly Gly Asn Pro Phe Glu Gly Tyr Asp Leu Tyr Val Asn
1               5                   10                  15

Pro Tyr Tyr Lys Ser Glu Val Glu Ser Leu Ala Ile Pro Ser Met Thr
                20                  25                  30

Gly Ser Leu Ala Glu Lys Ala Ser Ala Ala Asn Val Pro Ser Phe
            35                  40                  45

His Trp Leu Asp Thr Thr Asp Lys Val Pro Gln Met Gly Glu Phe Leu
50                  55                  60

Glu Asp Ile Lys Thr Lys Asn Ala Ala Gly Ala Asn Pro Thr Ala
65                  70                  75                  80

Gly Ile Phe Val Val Tyr Asp Leu Pro Asp Arg Asp Cys Ala Ala Leu
                85                  90                  95
```

Ala Ser Asn Gly Glu Phe Leu Ile Ser Asp Gly Gly Val Glu Lys Tyr
                100                 105                 110

Lys Ala Tyr Ile Asp Ser Ile Arg Glu Gln Val Glu Lys Tyr Ser Asp
            115                 120                 125

Thr Gln Ile Ile Leu Val Ile Glu Pro Asp Ser Leu Ala Asn Leu Val
        130                 135                 140

Thr Asn Leu Asn Val Gln Lys Cys Ala Asn Ala Gln Asp Ala Tyr Leu
145                 150                 155                 160

Glu Cys Thr Asn Tyr Ala Leu Thr Gln Leu Asn Leu Pro Asn Val Ala
                165                 170                 175

Met Tyr Leu Asp Ala Gly His Ala Gly Trp Leu Gly Trp Pro Ala Asn
            180                 185                 190

Ile Gly Pro Ala Ala Glu Leu Tyr Ala Ser Val Tyr Lys Asn Ala Ser
        195                 200                 205

Ser Pro Ala Ala Val Arg Gly Leu Ala Thr Asn Val Ala Asn Tyr Asn
210                 215                 220

Ala Phe Ser Ile Asp Ser Cys Pro Ser Tyr Thr Gln Gly Ser Thr Val
225                 230                 235                 240

Cys Asp Glu Lys Thr Tyr Ile Asn Asn Phe Ala Pro Gln Leu Lys Ser
                245                 250                 255

Ala Gly Phe Asp Ala His Phe Ile Val Asp Thr Gly Arg Asn Gly Asn
            260                 265                 270

Gln Pro Thr Gly Gln Ser Gln Trp Gly Asp Trp Cys Asn Val Lys Asn
        275                 280                 285

Thr Gly Phe Gly Val Arg Pro Thr Thr Asp Thr Gly Asp Glu Leu Val
290                 295                 300

Asp Ala Phe Val Trp Val Lys Pro Gly Gly Glu Ser Asp Gly Thr Ser
305                 310                 315                 320

Asp Thr Ser Ala Glu Arg Tyr Asp Ala His Cys Gly Tyr Ala Asp Ala
                325                 330                 335

Leu Thr Pro Ala Pro Glu Ala Gly Thr Trp Phe Gln Ala Tyr Phe Glu
            340                 345                 350

Gln Leu Val Glu Asn Ala Asn Pro Ser Leu
        355                 360

<210> SEQ ID NO 10
<211> LENGTH: 363
<212> TYPE: PRT
<213> ORGANISM: Aspergillus niger CBS 513.88

<400> SEQUENCE: 10

Ala Ser Ala Thr Gly Asn Pro Phe Glu Gly Tyr Gln Leu Tyr Ala Asn
1               5                   10                  15

Pro Tyr Tyr Lys Ser Gln Val Glu Ser Ser Ala Ile Pro Ser Leu Ser
            20                  25                  30

Ala Ser Ser Leu Val Ala Gln Ala Ser Ala Ala Asp Val Pro Ser
        35                  40                  45

Phe Tyr Trp Leu Asp Thr Ala Asp Lys Val Pro Thr Met Gly Glu Tyr
    50                  55                  60

Leu Glu Asp Ile Gln Thr Gln Asn Ala Ala Gly Ala Ser Pro Pro Ile
65                  70                  75                  80

Ala Gly Ile Phe Val Val Tyr Asp Leu Pro Asp Arg Asp Cys Ser Ala
                85                  90                  95

Leu Ala Ser Asn Gly Glu Tyr Ser Ile Ser Asp Gly Gly Val Glu Lys
            100                 105                 110

Tyr Lys Ala Tyr Ile Asp Ser Ile Arg Glu Gln Val Glu Thr Tyr Ser
            115                 120                 125

Asp Val Gln Thr Ile Leu Ile Ile Glu Pro Asp Ser Leu Ala Asn Leu
        130                 135                 140

Val Thr Asn Leu Asp Val Ala Lys Cys Ala Asn Ala Glu Ser Ala Tyr
145                 150                 155                 160

Leu Glu Cys Thr Asn Tyr Ala Leu Glu Gln Leu Asn Leu Pro Asn Val
                165                 170                 175

Ala Met Tyr Leu Asp Ala Gly His Ala Gly Trp Leu Gly Trp Pro Ala
            180                 185                 190

Asn Ile Gly Pro Ala Ala Gln Leu Tyr Ala Ser Val Tyr Lys Asn Ala
            195                 200                 205

Ser Ser Pro Ala Ala Val Arg Gly Leu Ala Thr Asn Val Ala Asn Phe
        210                 215                 220

Asn Ala Trp Ser Ile Asp Ser Cys Pro Ser Tyr Thr Ser Gly Asn Asp
225                 230                 235                 240

Val Cys Asp Glu Lys Ser Tyr Ile Asn Ala Ile Ala Pro Glu Leu Ser
                245                 250                 255

Ser Ala Gly Phe Asp Ala His Phe Ile Thr Asp Thr Gly Arg Asn Gly
            260                 265                 270

Lys Gln Pro Thr Gly Gln Ser Ala Trp Gly Asp Trp Cys Asn Val Lys
            275                 280                 285

Asp Thr Gly Phe Gly Ala Gln Pro Thr Thr Asp Thr Gly Asp Glu Leu
        290                 295                 300

Ala Asp Ala Phe Val Trp Val Lys Pro Gly Gly Glu Ser Asp Gly Thr
305                 310                 315                 320

Ser Asp Thr Ser Ser Arg Tyr Asp Ala His Cys Gly Tyr Ser Asp
                325                 330                 335

Ala Leu Gln Pro Ala Pro Glu Ala Gly Thr Trp Phe Gln Ala Tyr Phe
            340                 345                 350

Glu Gln Leu Leu Thr Asn Ala Asn Pro Ser Leu
        355                 360

<210> SEQ ID NO 11
<211> LENGTH: 364
<212> TYPE: PRT
<213> ORGANISM: Acremonium cellulolyticus Y-94

<400> SEQUENCE: 11

Ala Ala Ala Ser Gly Asn Pro Phe Ser Gly Tyr Gln Leu Tyr Ala Asn
1               5                   10                  15

Pro Tyr Tyr Ser Ser Glu Val His Thr Leu Ala Ile Pro Ser Leu Thr
            20                  25                  30

Gly Ser Leu Ala Ala Ala Ala Thr Lys Ala Ala Glu Ile Pro Ser Phe
        35                  40                  45

Val Trp Leu Asp Thr Ala Ala Lys Val Pro Thr Met Gly Thr Tyr Leu
    50                  55                  60

Ala Asn Ile Glu Ala Ala Asn Lys Ala Gly Ala Ser Pro Pro Ile Ala
65                  70                  75                  80

Gly Ile Phe Val Val Tyr Asp Leu Pro Asp Arg Asp Cys Ala Ala Ala
                85                  90                  95

Ala Ser Asn Gly Glu Tyr Thr Val Ala Asn Asn Gly Val Ala Asn Tyr
            100                 105                 110

Lys Ala Tyr Ile Asp Ser Ile Val Ala Gln Leu Lys Ala Tyr Pro Asp
            115                 120                 125

```
Val His Thr Ile Leu Ile Ile Glu Pro Asp Ser Leu Ala Asn Met Val
    130                 135                 140

Thr Asn Leu Ser Thr Ala Lys Cys Ala Glu Ala Gln Ser Ala Tyr Tyr
145                 150                 155                 160

Glu Cys Val Asn Tyr Ala Leu Ile Asn Leu Asn Leu Ala Asn Val Ala
                165                 170                 175

Met Tyr Ile Asp Ala Gly His Ala Gly Trp Leu Gly Trp Ser Ala Asn
            180                 185                 190

Leu Ser Pro Ala Ala Gln Leu Phe Ala Thr Val Tyr Lys Asn Ala Ser
        195                 200                 205

Ala Pro Ala Ser Leu Arg Gly Leu Ala Thr Asn Val Ala Asn Tyr Asn
    210                 215                 220

Ala Trp Ser Ile Ser Ser Pro Ser Tyr Thr Ser Gly Asp Ser Asn
225                 230                 235                 240

Tyr Asp Glu Lys Leu Tyr Ile Asn Ala Leu Ser Pro Leu Leu Thr Ser
                245                 250                 255

Asn Gly Trp Pro Asn Ala His Phe Ile Met Asp Thr Ser Arg Asn Gly
            260                 265                 270

Val Gln Pro Thr Lys Gln Ala Trp Gly Asp Trp Cys Asn Val Ile
        275                 280                 285

Gly Thr Gly Phe Gly Val Gln Pro Thr Thr Asn Thr Gly Asp Pro Leu
    290                 295                 300

Glu Asp Ala Phe Val Trp Val Lys Pro Gly Gly Glu Ser Asp Gly Thr
305                 310                 315                 320

Ser Asn Ser Ser Ala Thr Arg Tyr Asp Phe His Cys Gly Tyr Ser Asp
                325                 330                 335

Ala Leu Gln Pro Ala Pro Glu Ala Gly Thr Trp Phe Gln Ala Tyr Phe
            340                 345                 350

Val Gln Leu Leu Thr Asn Ala Asn Pro Ala Leu Val
        355                 360

<210> SEQ ID NO 12
<211> LENGTH: 362
<212> TYPE: PRT
<213> ORGANISM: Talaromyces emersonii

<400> SEQUENCE: 12

Ala Ser Ala Ser Gly Asn Pro Phe Glu Gly Tyr Gln Leu Tyr Ala Asn
1               5                   10                  15

Pro Tyr Tyr Ala Ser Glu Val Ile Ser Leu Ala Ile Pro Ser Leu Ser
            20                  25                  30

Ser Glu Leu Val Pro Lys Ala Ser Glu Val Ala Lys Val Pro Ser Phe
        35                  40                  45

Val Trp Leu Asp Gln Ala Ala Lys Val Pro Ser Met Gly Asp Tyr Leu
    50                  55                  60

Lys Asp Ile Gln Ser Gln Asn Ala Ala Gly Ala Asp Pro Pro Ile Ala
65                  70                  75                  80

Gly Ile Phe Val Val Tyr Asp Leu Pro Asp Arg Asp Cys Ala Ala Ala
                85                  90                  95

Ala Ser Asn Gly Glu Phe Ser Ile Ala Asn Asn Gly Val Ala Leu Tyr
            100                 105                 110

Lys Gln Tyr Ile Asp Ser Ile Arg Glu Gln Leu Thr Thr Tyr Ser Asp
        115                 120                 125

Val His Thr Ile Leu Val Ile Glu Pro Asp Ser Leu Ala Asn Val Val
    130                 135                 140
```

```
Thr Asn Leu Asn Val Pro Lys Cys Ala Asn Ala Gln Asp Ala Tyr Leu
145                 150                 155                 160

Glu Cys Ile Asn Tyr Ala Ile Thr Gln Leu Asp Leu Pro Asn Val Ala
            165                 170                 175

Met Tyr Leu Asp Ala Gly His Ala Gly Trp Leu Gly Trp Gln Ala Asn
        180                 185                 190

Leu Ala Pro Ala Ala Gln Leu Phe Ala Ser Val Tyr Lys Asn Ala Ser
    195                 200                 205

Ser Pro Ala Ser Val Arg Gly Leu Ala Thr Asn Val Ala Asn Tyr Asn
210                 215                 220

Ala Trp Ser Ile Ser Arg Cys Pro Ser Tyr Thr Gln Gly Asp Ala Asn
225                 230                 235                 240

Cys Asp Glu Glu Asp Tyr Val Asn Ala Leu Gly Pro Leu Phe Gln Glu
                245                 250                 255

Gln Gly Phe Pro Ala Tyr Phe Ile Ile Asp Thr Ser Arg Asn Gly Val
            260                 265                 270

Arg Pro Thr Lys Gln Ser Gln Trp Gly Asp Trp Cys Asn Val Ile Gly
        275                 280                 285

Thr Gly Phe Gly Val Arg Pro Thr Thr Asp Thr Gly Asn Pro Leu Glu
    290                 295                 300

Asp Ala Phe Val Trp Val Lys Pro Gly Gly Glu Ser Asp Gly Thr Ser
305                 310                 315                 320

Asn Thr Thr Ser Pro Arg Tyr Asp Tyr His Cys Gly Leu Ser Asp Ala
                325                 330                 335

Leu Gln Pro Ala Pro Glu Ala Gly Thr Trp Phe Gln Ala Tyr Phe Glu
            340                 345                 350

Gln Leu Leu Thr Asn Ala Asn Pro Leu Phe
            355                 360

<210> SEQ ID NO 13
<211> LENGTH: 361
<212> TYPE: PRT
<213> ORGANISM: Gibberella zeae K59

<400> SEQUENCE: 13

Pro Val Ala Thr Asn Asn Pro Phe Ser Gly Val Asp Leu Trp Ala Asn
1               5                   10                  15

Asn Tyr Tyr Arg Ser Glu Val Ser Thr Leu Ala Ile Pro Lys Leu Ser
            20                  25                  30

Gly Ala Met Ala Thr Ala Ala Lys Val Ala Asp Val Pro Ser Phe
        35                  40                  45

Gln Trp Met Asp Thr Tyr Asp His Ile Ser Phe Met Glu Asp Ser Leu
    50                  55                  60

Ala Asp Ile Arg Lys Ala Asn Lys Ala Gly Gly Asn Tyr Ala Gly Gln
65                  70                  75                  80

Phe Val Val Tyr Asp Leu Pro Asp Arg Asp Cys Ala Ala Ala Ala Ser
                85                  90                  95

Asn Gly Glu Tyr Ser Leu Asp Lys Asp Gly Lys Asn Lys Tyr Lys Ala
            100                 105                 110

Tyr Ile Ala Asp Gln Gly Ile Leu Gln Asp Tyr Ser Asp Thr Arg Ile
        115                 120                 125

Ile Leu Val Ile Glu Pro Asp Ser Leu Ala Asn Met Val Thr Asn Met
    130                 135                 140

Asn Val Pro Lys Cys Ala Asn Ala Ala Ser Ala Tyr Lys Glu Leu Thr
145                 150                 155                 160
```

```
Ile His Ala Leu Lys Glu Leu Asn Leu Pro Asn Val Ser Met Tyr Ile
                165                 170                 175

Asp Ala Gly His Gly Gly Trp Leu Gly Trp Pro Ala Asn Leu Pro Pro
            180                 185                 190

Ala Ala Gln Leu Tyr Gly Gln Leu Tyr Lys Asp Ala Gly Lys Pro Ser
            195                 200                 205

Arg Leu Arg Gly Leu Val Thr Asn Val Ser Asn Tyr Asn Ala Trp Lys
            210                 215                 220

Leu Ser Ser Lys Pro Asp Tyr Thr Glu Ser Asn Pro Asn Tyr Asp Glu
225                 230                 235                 240

Gln Lys Tyr Ile His Ala Leu Ser Pro Leu Glu Gln Glu Gly Trp
                245                 250                 255

Pro Gly Ala Lys Phe Ile Val Asp Gln Gly Arg Ser Gly Lys Gln Pro
            260                 265                 270

Thr Gly Gln Lys Ala Trp Gly Asp Trp Cys Asn Ala Pro Gly Thr Gly
            275                 280                 285

Phe Gly Leu Arg Pro Ser Ala Asn Thr Gly Asp Ala Leu Val Asp Ala
            290                 295                 300

Phe Val Trp Val Lys Pro Gly Gly Glu Ser Asp Gly Thr Ser Asp Thr
305                 310                 315                 320

Ser Ala Ala Arg Tyr Asp Tyr His Cys Gly Ile Asp Gly Ala Val Lys
                325                 330                 335

Pro Ala Pro Glu Ala Gly Thr Trp Phe Gln Ala Tyr Phe Glu Gln Leu
            340                 345                 350

Leu Lys Asn Ala Asn Pro Ser Phe Leu
            355                 360

<210> SEQ ID NO 14
<211> LENGTH: 362
<212> TYPE: PRT
<213> ORGANISM: Fusarium oxysporum

<400> SEQUENCE: 14

Pro Ala Ala Ser Asp Asn Pro Tyr Ala Gly Val Asp Leu Trp Ala Asn
1               5                   10                  15

Asn Tyr Tyr Arg Ser Glu Val Met Asn Leu Ala Val Pro Lys Leu Ser
                20                  25                  30

Gly Ala Lys Ala Thr Ala Ala Lys Val Ala Asp Val Pro Ser Phe
            35                  40                  45

Gln Trp Met Asp Thr Tyr Asp His Ile Ser Leu Met Glu Asp Thr Leu
50                  55                  60

Ala Asp Ile Arg Lys Ala Asn Lys Ala Gly Gly Lys Tyr Ala Gly Gln
65                  70                  75                  80

Phe Val Val Tyr Asp Leu Pro Asn Arg Asp Cys Ala Ala Ala Ser
                85                  90                  95

Asn Gly Glu Tyr Ser Leu Asp Lys Asp Gly Ala Asn Lys Tyr Lys Ala
                100                 105                 110

Tyr Ile Ala Lys Ile Lys Gly Ile Leu Gln Asn Tyr Ser Asp Thr Lys
            115                 120                 125

Val Ile Leu Val Ile Glu Pro Asp Ser Leu Ala Asn Leu Val Thr Asn
            130                 135                 140

Leu Asn Val Asp Lys Cys Ala Lys Ala Glu Ser Ala Tyr Lys Glu Leu
145                 150                 155                 160

Thr Val Tyr Ala Ile Lys Glu Leu Asn Leu Pro Asn Val Ser Met Tyr
                165                 170                 175
```

-continued

```
Leu Asp Ala Gly His Gly Gly Trp Leu Gly Trp Pro Ala Asn Ile Gly
            180                 185                 190
Pro Ala Ala Lys Leu Tyr Ala Gln Ile Tyr Lys Asp Ala Gly Lys Pro
        195                 200                 205
Ser Arg Val Arg Gly Leu Val Thr Asn Val Ser Asn Tyr Asn Gly Trp
    210                 215                 220
Lys Leu Ser Thr Lys Pro Asp Tyr Thr Glu Ser Asn Pro Asn Tyr Asp
225                 230                 235                 240
Glu Gln Arg Tyr Ile Asn Ala Phe Ala Pro Leu Leu Ala Gln Glu Gly
                245                 250                 255
Trp Ser Asn Val Lys Phe Ile Val Asp Gln Gly Arg Ser Gly Lys Gln
            260                 265                 270
Pro Thr Gly Gln Lys Ala Gln Gly Asp Trp Cys Asn Ala Lys Gly Thr
        275                 280                 285
Gly Phe Gly Leu Arg Pro Ser Thr Asn Thr Gly Asp Ala Leu Ala Asp
    290                 295                 300
Ala Phe Val Trp Val Lys Pro Gly Gly Glu Ser Asp Gly Thr Ser Asp
305                 310                 315                 320
Thr Ser Ala Ala Arg Tyr Asp Tyr His Cys Gly Leu Asp Asp Ala Leu
                325                 330                 335
Lys Pro Ala Pro Glu Ala Gly Thr Trp Phe Gln Ala Tyr Phe Glu Gln
            340                 345                 350
Leu Leu Asp Asn Ala Asn Pro Ser Phe Leu
        355                 360

<210> SEQ ID NO 15
<211> LENGTH: 363
<212> TYPE: PRT
<213> ORGANISM: Neurospora crassa OR74A

<400> SEQUENCE: 15

Ala Ser Phe Thr Gly Asn Pro Phe Leu Gly Val Gln Gly Trp Ala Asn
1               5                   10                  15
Ser Tyr Tyr Ser Ser Glu Ile Tyr Asn His Ala Ile Pro Ser Met Thr
            20                  25                  30
Gly Ser Leu Ala Ala Gln Ala Ser Ala Val Ala Lys Val Pro Thr Phe
        35                  40                  45
Gln Trp Leu Asp Arg Asn Val Thr Val Asp Thr Leu Met Lys Ser Thr
    50                  55                  60
Leu Glu Glu Ile Arg Ala Asn Lys Ala Gly Ala Asn Pro Pro Tyr
65                  70                  75                  80
Ala Ala His Phe Val Val Tyr Asp Leu Pro Asp Arg Asp Cys Ala Ala
                85                  90                  95
Ala Ala Ser Asn Gly Glu Phe Ser Ile Ala Asn Gly Gly Val Ala Asn
            100                 105                 110
Tyr Lys Thr Tyr Ile Asn Ala Ile Arg Lys Leu Leu Ile Glu Tyr Ser
        115                 120                 125
Asp Ile Arg Thr Ile Leu Val Ile Glu Pro Asp Ser Leu Ala Asn Leu
    130                 135                 140
Val Thr Asn Thr Asn Val Ala Lys Cys Ala Asn Ala Ala Ser Ala Tyr
145                 150                 155                 160
Arg Glu Cys Thr Asn Tyr Ala Ile Thr Gln Leu Asp Leu Pro His Val
                165                 170                 175
Ala Gln Tyr Leu Asp Ala Gly His Gly Gly Trp Leu Gly Trp Pro Ala
            180                 185                 190
```

```
Asn Ile Gln Pro Ala Ala Thr Leu Phe Ala Asp Ile Tyr Lys Ala Ala
            195                 200                 205

Gly Lys Pro Lys Ser Val Arg Gly Leu Val Thr Asn Val Ser Asn Tyr
        210                 215                 220

Asn Gly Trp Ser Leu Ser Ser Ala Pro Ser Tyr Thr Thr Pro Asn Pro
225                 230                 235                 240

Asn Tyr Asp Glu Lys Lys Tyr Ile Glu Ala Phe Ser Pro Leu Leu Asn
                245                 250                 255

Ala Ala Gly Phe Pro Ala Gln Phe Ile Val Asp Thr Gly Arg Ser Gly
                260                 265                 270

Lys Gln Pro Thr Gly Gln Ile Glu Gln Gly Asp Trp Cys Asn Ala Ile
        275                 280                 285

Gly Thr Gly Phe Gly Val Arg Pro Thr Thr Asn Thr Gly Ser Ser Leu
        290                 295                 300

Ala Asp Ala Phe Val Trp Val Lys Pro Gly Gly Glu Ser Asp Gly Thr
305                 310                 315                 320

Ser Asp Thr Ser Ala Thr Arg Tyr Asp Tyr His Cys Gly Leu Ser Asp
                325                 330                 335

Ala Leu Lys Pro Ala Pro Glu Ala Gly Gln Trp Phe Gln Ala Tyr Phe
                340                 345                 350

Glu Gln Leu Leu Lys Asn Ala Asn Pro Ala Phe
        355                 360

<210> SEQ ID NO 16
<211> LENGTH: 364
<212> TYPE: PRT
<213> ORGANISM: Aspergillus nidulans FGSC A4

<400> SEQUENCE: 16

Val Gln Ala Thr Gly Asn Pro Phe Glu Gly Tyr Gln Leu Tyr Ala Asn
1               5                   10                  15

Pro Tyr Tyr Ser Ser Glu Val Met Thr Leu Ala Val Pro Ser Met Thr
                20                  25                  30

Gly Ser Leu Ala Glu Gln Ala Thr His Ala Ala Glu Ile Pro Ser Phe
        35                  40                  45

His Trp Leu Asp Thr Thr Ala Lys Val Pro Thr Met Gly Glu Tyr Leu
50                  55                  60

Ala Asp Ile Lys Glu Gln Asn Asp Ala Gly Ala Asn Pro Pro Ile Ala
65                  70                  75                  80

Gly Ile Phe Val Val Tyr Asn Leu Pro Asp Arg Asp Cys Ala Ala Leu
                85                  90                  95

Ala Ser Asn Gly Glu Leu Ser Ile Ala Asp Gly Gly Val Glu Lys Tyr
                100                 105                 110

Lys Glu Tyr Ile Asp Ala Ile Arg Ala His Ala Val Glu Tyr Ser Asp
        115                 120                 125

Thr Asn Ile Ile Leu Ile Ile Glu Pro Asp Ser Leu Ala Asn Leu Val
        130                 135                 140

Thr Asn Leu Asn Val Glu Lys Cys Ala Asn Ala Gln Asp Ala Tyr Leu
145                 150                 155                 160

Glu Cys Thr Asn Tyr Ala Ile Thr Gln Leu Asp Leu Pro Asn Val Ser
                165                 170                 175

Met Tyr Leu Asp Ala Gly His Ala Gly Trp Leu Gly Trp Pro Ala Asn
                180                 185                 190

Ile Gly Pro Ala Ala Gln Leu Phe Ala Gly Val Tyr Gln Asp Ala Gly
        195                 200                 205
```

```
Ala Pro Ala Ala Leu Arg Gly Leu Ala Thr Asn Val Ala Asn Tyr Asn
        210                 215                 220

Ala Phe Ser Ile Asp Thr Cys Pro Ser Tyr Thr Ser Gln Asn Ala Val
225                 230                 235                 240

Cys Asp Glu Lys Gly Tyr Ile Asn Ser Phe Ala Pro Glu Leu Ser Ala
                245                 250                 255

Ala Gly Trp Asp Ala His Phe Ile Val Asp Thr Gly Arg Asn Gly Lys
                260                 265                 270

Gln Pro Thr Gly Gln Ile Glu Trp Gly Asp Trp Cys Asn Val Lys Gly
                275                 280                 285

Thr Gly Phe Gly Val Arg Pro Thr Thr Asp Thr Gly Asp Glu Leu Val
        290                 295                 300

Asp Ala Phe Val Trp Val Lys Pro Gly Gly Glu Ser Asp Gly Thr Ser
305                 310                 315                 320

Asp Gln Ser Ala Glu Arg Tyr Asp Ala His Cys Gly Ala Ala Ala Ala
                325                 330                 335

Leu Gln Pro Ala Pro Glu Ala Gly Thr Trp Phe Gln Ala Tyr Phe Glu
                340                 345                 350

Gln Leu Val Ala Asn Ala Asn Pro Pro Leu Ser Ser
                355                 360

<210> SEQ ID NO 17
<211> LENGTH: 363
<212> TYPE: PRT
<213> ORGANISM: Aspergillus tubingensis
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid

<400> SEQUENCE: 17

Ala Ser Ala Thr Gly Asn Pro Phe Glu Gly Tyr Gln Leu Tyr Val Asn
1               5                   10                  15

Pro Tyr Tyr Lys Ser Gln Val Glu Ser Ser Ala Ile Pro Ser Leu Ser
                20                  25                  30

Ala Ser Ser Leu Val Ala Gln Ser Ala Ala Ala Asp Val Pro Ser
        35                  40                  45

Phe Tyr Trp Leu Asp Thr Ala Asp Lys Val Pro Thr Met Gly Glu Tyr
50                  55                  60

Leu Asp Asp Ile Gln Thr Gln Asn Ala Ala Gly Ala Asn Pro Pro Ile
65                  70                  75                  80

Ala Gly Ile Phe Val Val Tyr Asp Leu Pro Asp Arg Asp Cys Ala Ala
                85                  90                  95

Leu Ala Ser Asn Gly Glu Tyr Ala Ile Ser Asp Gly Gly Val Glu Lys
                100                 105                 110

Tyr Lys Ala Tyr Ile Asp Ser Ile Arg Glu Gln Val Glu Thr Tyr Ser
                115                 120                 125

Asp Val Gln Thr Ile Leu Ile Ile Glu Pro Asp Ser Leu Ala Asn Leu
        130                 135                 140

Val Thr Asn Leu Asp Val Ala Lys Cys Ala Asn Ala Gln Ser Ala Tyr
145                 150                 155                 160
```

```
Leu Glu Cys Thr Asn Tyr Ala Leu Glu Gln Leu Asn Leu Pro Asn Val
                165                 170                 175

Ala Met Tyr Leu Asp Ala Gly His Ala Gly Trp Leu Gly Trp Pro Ala
            180                 185                 190

Asn Ile Gly Pro Ala Ala Glu Leu Tyr Ala Ser Val Tyr Lys Asn Ala
        195                 200                 205

Ser Ser Pro Ala Ala Val Arg Gly Leu Ala Thr Asx Val Ala Asn Phe
    210                 215                 220

Asn Ala Trp Ser Ile Asp Thr Cys Pro Ser Tyr Thr Ser Gly Asn Asp
225                 230                 235                 240

Val Cys Asp Glu Lys Ser Tyr Ile Asn Ala Phe Ala Pro Glu Leu Ser
                245                 250                 255

Xaa Ala Gly Phe Asp Ala His Phe Ile Thr Asp Thr Gly Arg Asn Gly
            260                 265                 270

Lys Gln Pro Thr Gly Gln Ser Ala Trp Gly Asp Trp Gly Asn Val Lys
        275                 280                 285

Asp Thr Gly Phe Gly Ala Xaa Pro Thr Thr Asp Thr Gly Asn Glu Leu
    290                 295                 300

Ala Asp Ala Phe Val Trp Xaa Asn Pro Gly Gly Lys Ser Asp Gly Thr
305                 310                 315                 320

Ser Asp Thr Ser Ser Arg Tyr Asp Ala His Cys Gly Tyr Ser Asp
                325                 330                 335

Ala Leu Gln Pro Ala Pro Glu Ala Gly Thr Trp Phe Gln Ala Tyr Phe
            340                 345                 350

Glu Gln Leu Leu Thr Asn Ala Asn Pro Ser Leu
        355                 360

<210> SEQ ID NO 18
<211> LENGTH: 362
<212> TYPE: PRT
<213> ORGANISM: Magnaporthe grisea 70-15

<400> SEQUENCE: 18

Ala Ser Phe Thr Gly Asn Pro Phe Ala Gly Val Asn Leu Phe Pro Asn
1               5                   10                  15

Lys Phe Tyr Ser Ser Glu Val His Thr Leu Ala Ile Pro Ser Leu Thr
            20                  25                  30

Gly Ser Leu Val Ala Lys Ala Ser Ala Val Ala Gln Val Pro Ser Phe
        35                  40                  45

Gln Trp Leu Asp Ile Ala Ala Lys Val Glu Thr Leu Met Pro Gly Ala
    50                  55                  60

Leu Ala Asp Val Arg Ala Ala Asn Ala Ala Gly Gly Asn Tyr Ala Ala
65                  70                  75                  80

Gln Leu Val Val Tyr Asp Leu Pro Asp Arg Asp Cys Ala Ala Ala Ala
                85                  90                  95

Ser Asn Gly Glu Phe Ser Ile Ala Asp Gly Gly Val Val Lys Tyr Lys
            100                 105                 110

Ala Tyr Ile Asp Ala Ile Arg Lys Gln Leu Leu Ala Tyr Ser Asp Val
        115                 120                 125

Arg Thr Ile Leu Val Ile Glu Pro Asp Ser Leu Ala Asn Met Val Thr
    130                 135                 140

Asn Met Gly Val Pro Lys Cys Ala Gly Ala Lys Asp Ala Tyr Leu Glu
145                 150                 155                 160

Cys Thr Ile Tyr Ala Val Lys Gln Leu Asn Leu Pro His Val Ala Met
                165                 170                 175
```

Tyr Leu Asp Gly Gly His Ala Gly Trp Leu Gly Trp Pro Ala Asn Leu
                180                 185                 190

Gln Pro Ala Ala Asp Leu Phe Gly Lys Leu Tyr Ala Asp Ala Gly Lys
            195                 200                 205

Pro Ser Gln Leu Arg Gly Met Ala Thr Asn Val Ala Asn Tyr Asn Ala
        210                 215                 220

Trp Asp Leu Thr Thr Ala Pro Ser Tyr Thr Thr Pro Asn Pro Asn Phe
225                 230                 235                 240

Asp Glu Lys Lys Tyr Ile Ser Ala Phe Ala Pro Leu Leu Ala Ala Lys
                245                 250                 255

Gly Trp Ser Ala His Phe Ile Ile Asp Gln Gly Arg Ser Gly Lys Gln
            260                 265                 270

Pro Thr Gly Gln Lys Glu Trp Gly His Trp Cys Asn Gln Gln Gly Val
        275                 280                 285

Gly Phe Gly Arg Arg Pro Ser Ala Asn Thr Gly Ser Glu Leu Ala Asp
    290                 295                 300

Ala Phe Val Trp Ile Lys Pro Gly Gly Glu Cys Asp Gly Val Ser Asp
305                 310                 315                 320

Pro Thr Ala Pro Arg Phe Asp His Phe Cys Gly Thr Asp Tyr Gly Ala
                325                 330                 335

Met Ser Asp Ala Pro Gln Ala Gly Gln Trp Phe Gln Lys Tyr Phe Glu
            340                 345                 350

Met Leu Leu Thr Asn Ala Asn Pro Pro Leu
        355                 360

<210> SEQ ID NO 19
<211> LENGTH: 364
<212> TYPE: PRT
<213> ORGANISM: Chaetomium thermophilum

<400> SEQUENCE: 19

Ala Ser Tyr Asn Gly Asn Pro Phe Ser Gly Val Gln Leu Trp Ala Asn
1               5                   10                  15

Thr Tyr Tyr Ser Ser Glu Val His Thr Leu Ala Ile Pro Ser Leu Ser
            20                  25                  30

Pro Glu Leu Ala Ala Lys Ala Ala Lys Val Ala Glu Val Pro Ser Phe
        35                  40                  45

Gln Trp Leu Asp Arg Asn Val Thr Val Asp Thr Leu Phe Ser Gly Thr
    50                  55                  60

Leu Ala Glu Ile Arg Ala Ala Asn Gln Arg Gly Ala Asn Pro Pro Tyr
65                  70                  75                  80

Ala Gly Ile Phe Val Val Tyr Asp Leu Pro Asp Arg Asp Cys Ala Ala
                85                  90                  95

Ala Ala Ser Asn Gly Glu Trp Ser Ile Ala Asn Asn Gly Ala Asn Asn
            100                 105                 110

Tyr Lys Arg Tyr Ile Asp Arg Ile Arg Glu Leu Leu Ile Gln Tyr Ser
        115                 120                 125

Asp Ile Arg Thr Ile Leu Val Ile Glu Pro Asp Ser Leu Ala Asn Met
    130                 135                 140

Val Thr Asn Met Asn Val Gln Lys Cys Ser Asn Ala Ala Ser Thr Tyr
145                 150                 155                 160

Lys Glu Leu Thr Val Tyr Ala Leu Lys Gln Leu Asn Leu Pro His Val
                165                 170                 175

Ala Met Tyr Met Asp Ala Gly His Ala Gly Trp Leu Gly Trp Pro Ala
            180                 185                 190

Asn Ile Gln Pro Ala Ala Glu Leu Phe Ala Gln Ile Tyr Arg Asp Ala
            195                 200                 205

Gly Arg Pro Ala Ala Val Arg Gly Leu Ala Thr Asn Val Ala Asn Tyr
    210                 215                 220

Asn Ala Trp Ser Ile Ala Ser Pro Ser Tyr Thr Ser Pro Asn Pro
225                 230                 235                 240

Asn Tyr Asp Glu Lys His Tyr Ile Glu Ala Phe Ala Pro Leu Leu Arg
            245                 250                 255

Asn Gln Gly Phe Asp Ala Lys Phe Ile Val Asp Thr Gly Arg Asn Gly
            260                 265                 270

Lys Gln Pro Thr Gly Gln Leu Glu Trp Gly His Trp Cys Asn Val Lys
            275                 280                 285

Gly Thr Gly Phe Gly Val Arg Pro Thr Ala Asn Thr Gly His Glu Leu
            290                 295                 300

Val Asp Ala Phe Val Trp Val Lys Pro Gly Gly Glu Ser Asp Gly Thr
305                 310                 315                 320

Ser Ala Asp Thr Ser Ala Ala Arg Tyr Asp Tyr His Cys Gly Leu Ser
            325                 330                 335

Asp Ala Leu Thr Pro Ala Pro Glu Ala Gly Gln Trp Phe Gln Ala Tyr
            340                 345                 350

Phe Glu Gln Leu Leu Ile Asn Ala Asn Pro Pro Leu
            355                 360

<210> SEQ ID NO 20
<211> LENGTH: 363
<212> TYPE: PRT
<213> ORGANISM: Chaetomium thermophilum CT2

<400> SEQUENCE: 20

Ala Ser Tyr Asn Gly Asn Pro Phe Ser Gly Val Gln Leu Trp Ala Asn
1               5                   10                  15

Thr Tyr Tyr Ser Ser Glu Val His Thr Leu Ala Ile Pro Ser Leu Ser
            20                  25                  30

Pro Glu Leu Ala Ala Lys Ala Ala Lys Val Ala Glu Val Pro Ser Phe
        35                  40                  45

Gln Trp Leu Asp Arg Asn Val Thr Val Asp Thr Leu Phe Ser Gly Thr
    50                  55                  60

Leu Ala Glu Ile Arg Ala Ala Asn Gln Arg Gly Ala Asn Pro Pro Tyr
65                  70                  75                  80

Ala Gly Ile Phe Val Val Tyr Asp Leu Pro Asp Arg Asp Cys Ala Ala
            85                  90                  95

Ala Ala Ser Asn Gly Glu Trp Ser Ile Ala Asn Asn Gly Ala Asn Asn
            100                 105                 110

Leu Gln Arg Tyr Ile Asp Arg Ile Arg Glu Leu Leu Ile Gln Tyr Ser
            115                 120                 125

Asp Ile Arg Thr Ile Leu Val Ile Glu Pro Asp Ser Leu Ala Asn Met
    130                 135                 140

Val Thr Asn Met Asn Val Gln Lys Cys Ser Asn Ala Ala Ser Thr Tyr
145                 150                 155                 160

Lys Glu Leu Thr Val Tyr Ala Leu Lys Gln Leu Asn Leu Pro His Val
            165                 170                 175

Ala Met Tyr Met Asp Ala Gly His Ala Gly Trp Leu Gly Trp Pro Ala
            180                 185                 190

Asn Ile Gln Pro Ala Ala Glu Leu Phe Ala Gln Ile Tyr Arg Asp Ala
            195                 200                 205

```
Gly Arg Pro Ala Ala Val Arg Gly Leu Ala Thr Asn Val Ala Asn Tyr
    210                 215                 220

Asn Ala Trp Ser Ile Ala Ser Pro Pro Ser Tyr Thr Ser Pro Asn Pro
225                 230                 235                 240

Asn Tyr Asp Glu Lys His Tyr Ile Glu Ala Phe Ala Pro Leu Leu Arg
                245                 250                 255

Asn Gln Gly Phe Asp Ala Lys Phe Ile Val Asp Thr Gly Arg Asn Gly
            260                 265                 270

Lys Gln Pro Thr Gly Gln Leu Glu Trp Gly His Trp Cys Asn Val Lys
        275                 280                 285

Gly Thr Gly Phe Gly Val Arg Pro Thr Ala Asn Thr Gly His Glu Leu
    290                 295                 300

Val Asp Ala Phe Val Trp Val Lys Pro Gly Gly Glu Ser Asp Gly Thr
305                 310                 315                 320

Ser Asp Thr Ser Ala Ala Arg Tyr Asp Tyr His Cys Gly Leu Ser Asp
                325                 330                 335

Ala Leu Thr Pro Ala Pro Glu Ala Gly Gln Trp Phe Gln Ala Tyr Phe
            340                 345                 350

Glu Gln Leu Leu Ile Asn Ala Asn Pro Pro Phe
        355                 360

<210> SEQ ID NO 21
<211> LENGTH: 360
<212> TYPE: PRT
<213> ORGANISM: Stilbella annulata

<400> SEQUENCE: 21

Ala Thr Tyr Thr Gly Asn Pro Phe Leu Gly Val Asn Gln Trp Ala Asn
1               5                   10                  15

Asn Phe Tyr Arg Ser Glu Ile Met Asn Ile Ala Val Pro Ser Leu Ser
            20                  25                  30

Gly Ala Met Ala Thr Ala Ala Lys Val Ala Asp Val Pro Thr Phe
        35                  40                  45

Gln Trp Ile Asp Lys Met Asp Lys Leu Pro Leu Ile Asp Glu Ala Leu
    50                  55                  60

Ala Asp Val Arg Ala Ala Asn Ala Arg Gly Gly Asn Tyr Ala Ser Ile
65                  70                  75                  80

Leu Val Val Tyr Asn Leu Pro Asp Arg Asp Cys Ala Ala Ala Ser
                85                  90                  95

Asn Gly Glu Phe Ala Ile Ala Asp Gly Gly Val Ala Lys Tyr Lys Asn
            100                 105                 110

Tyr Ile Asp Glu Ile Arg Lys Leu Val Ile Lys Tyr Asn Asp Leu Arg
        115                 120                 125

Ile Ile Leu Val Ile Glu Pro Asp Ser Leu Ala Asn Met Val Thr Asn
    130                 135                 140

Met Asn Val Ala Lys Cys Gln Asn Ala Ala Ser Ala Tyr Arg Glu Cys
145                 150                 155                 160

Thr Asn Tyr Ala Leu Thr Asn Leu Asp Leu Pro Asn Val Ala Gln Tyr
                165                 170                 175

Met Asp Ala Gly His Ala Gly Trp Leu Gly Trp Pro Ala Asn Ile Thr
            180                 185                 190

Pro Ala Ala Gln Leu Phe Ala Glu Val Tyr Lys Gln Ala Gly Ser Pro
        195                 200                 205

Lys Ser Val Arg Gly Leu Ala Ile Asn Val Ser Asn Tyr Asn Ala Trp
    210                 215                 220
```

```
Ser Val Ser Ser Pro Pro Tyr Thr Ser Pro Asn Pro Asn Tyr Asp
225                 230                 235                 240

Glu Arg His Phe Val Glu Ala Phe Ala Pro Leu Leu Arg Gln Asn Gly
            245                 250                 255

Trp Asp Ala Lys Phe Ile Val Asp Gln Gly Arg Ser Gly Arg Gln Pro
                260                 265                 270

Thr Gly Gln Gln Glu Trp Gly His Trp Cys Asn Ala Ile Gly Thr Gly
            275                 280                 285

Phe Gly Gln Arg Pro Thr Ser Asn Thr Gly His Ala Asp Val Asp Ala
            290                 295                 300

Phe Val Trp Ile Lys Pro Gly Gly Glu Cys Asp Gly Thr Ser Asp Thr
305                 310                 315                 320

Ser Ala Ala Arg Tyr Asp His Phe Cys Gly Asn Pro Asp Ala Leu Lys
                325                 330                 335

Pro Ala Pro Glu Ala Gly Glu Trp Phe Gln Ala Tyr Phe Glu Gln Leu
            340                 345                 350

Leu Arg Asn Ala Asn Pro Ala Phe
            355                 360

<210> SEQ ID NO 22
<211> LENGTH: 453
<212> TYPE: PRT
<213> ORGANISM: Humicola insolens

<400> SEQUENCE: 22

Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Ser Thr Thr
        35                  40                  45

Thr Ser Thr Ser Ser Ser Ser Thr Thr Ser Arg Ala Thr Ser Thr Thr
50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Tyr Lys Gly Tyr Ile Asn
        195                 200                 205

Arg Ile Arg Glu Ile Leu Ile Ser Phe Ser Asp Val Arg Thr Ile Leu
210                 215                 220

Val Ile Glu Pro Asp Ser Leu Ala Asn Met Val Thr Asn Met Asn Val
225                 230                 235                 240
```

Ala Lys Cys Ser Gly Ala Ala Ser Thr Tyr Arg Glu Leu Thr Ile Tyr
            245                 250                 255

Ala Leu Lys Gln Leu Asp Leu Pro His Val Ala Met Tyr Met Asp Ala
        260                 265                 270

Gly His Ala Gly Trp Leu Gly Trp Pro Ala Asn Ile Gln Pro Ala Ala
    275                 280                 285

Glu Leu Phe Ala Lys Ile Tyr Glu Asp Ala Gly Lys Pro Arg Ala Val
290                 295                 300

Arg Gly Leu Ala Thr Asn Val Ala Asn Tyr Asn Ala Trp Ser Ile Ser
305                 310                 315                 320

Ser Pro Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
            340                 345                 350

Gln Phe Ile Val Asp Gln Gly Arg Ser Gly Lys Gln Pro Thr Gly Gln
        355                 360                 365

Lys Glu Trp Gly His Trp Cys Asn Ala Ile Gly Thr Gly Phe Gly Met
    370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
            420                 425                 430

Glu Ala Gly Gln Trp Phe Gln Ala Tyr Phe Glu Gln Leu Leu Arg Asn
        435                 440                 445

Ala Asn Pro Pro Phe
    450

<210> SEQ ID NO 23
<211> LENGTH: 360
<212> TYPE: PRT
<213> ORGANISM: Humicola insolens

<400> SEQUENCE: 23

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ala Ser Ala Val Ala Glu Val Pro Ser Phe Gln Trp Leu
        35                  40                  45

Asp Arg Asn Val Thr Val Asp Thr Leu Leu Val Gln Thr Leu Ser Glu
    50                  55                  60

Ile Arg Glu Ala Asn Gln Ala Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
    130                 135                 140

Met Asn Val Pro Lys Cys Ser Gly Ala Ala Ser Thr Tyr Arg Glu Leu
145                 150                 155                 160

```
Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
            195                 200                 205

Arg Ala Val Arg Gly Leu Ala Thr Asn Val Ala Asn Tyr Asn Ala Trp
210                 215                 220

Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
                245                 250                 255

Phe Pro Ala Gln Phe Ile Val Asp Gln Gly Arg Ser Gly Lys Gln Pro
            260                 265                 270

Thr Gly Gln Lys Glu Trp Gly His Trp Cys Asn Ala Ile Gly Thr Gly
            275                 280                 285

Phe Gly Met Arg Pro Thr Ala Asn Thr Gly His Gln Tyr Val Asp Ala
            290                 295                 300

Phe Val Trp Val Lys Pro Gly Gly Glu Cys Asp Gly Thr Ser Asp Thr
305                 310                 315                 320

Thr Ala Ala Arg Tyr Asp Tyr His Cys Gly Leu Glu Asp Ala Leu Lys
                325                 330                 335

Pro Ala Pro Glu Ala Gly Gln Trp Phe Asn Glu Tyr Phe Ile Gln Leu
            340                 345                 350

Leu Arg Asn Ala Asn Pro Pro Phe
            355                 360

<210> SEQ ID NO 24
<211> LENGTH: 362
<212> TYPE: PRT
<213> ORGANISM: Cochliobolus heterostrophus C4

<400> SEQUENCE: 24

Ala Ala Pro Ser Gly Asn Pro Phe Ala Gly Lys Asn Phe Tyr Ala Asn
1               5                   10                  15

Pro Tyr Tyr Ser Ser Glu Val His Thr Leu Ala Met Pro Ser Leu Pro
            20                  25                  30

Ala Ser Leu Lys Pro Ala Ala Thr Ala Val Ala Lys Val Gly Ser Phe
        35                  40                  45

Val Trp Met Asp Thr Met Ala Lys Val Pro Leu Met Asp Thr Tyr Leu
50                  55                  60

Ala Asp Ile Lys Ala Lys Asn Ala Ala Gly Ala Asn Leu Met Gly Thr
65                  70                  75                  80

Phe Val Val Tyr Asp Leu Pro Asp Arg Asp Cys Ala Ala Leu Ala Ser
                85                  90                  95

Asn Gly Glu Leu Lys Ile Asp Glu Gly Gly Val Glu Lys Tyr Lys Thr
            100                 105                 110

Gln Tyr Ile Asp Lys Ile Ala Ala Ile Ile Lys Lys Tyr Pro Asp Val
            115                 120                 125

Lys Ile Asn Leu Ala Ile Glu Pro Asp Ser Leu Ala Asn Met Val Thr
130                 135                 140

Asn Met Gly Val Gln Lys Cys Ser Arg Ala Ala Pro Tyr Tyr Lys Glu
145                 150                 155                 160

Leu Thr Ala Tyr Ala Leu Lys Thr Leu Asn Phe Asn Asn Val Asp Met
                165                 170                 175
```

```
Tyr Met Asp Gly Gly His Ala Gly Trp Leu Gly Trp Asp Ala Asn Ile
            180                 185                 190

Gly Pro Thr Ala Lys Leu Phe Ala Glu Val Tyr Lys Ala Ala Gly Ser
        195                 200                 205

Pro Arg Gly Val Arg Gly Ile Val Thr Asn Val Ser Asn Tyr Asn Ala
210                 215                 220

Leu Arg Val Ser Ser Cys Pro Ser Ile Thr Gln Gly Asn Lys Asn Cys
225                 230                 235                 240

Asp Glu Glu Arg Tyr Ile Asn Ala Leu Ala Pro Leu Leu Lys Asn Glu
                245                 250                 255

Gly Phe Pro Ala His Phe Ile Val Asp Gln Gly Arg Ser Gly Lys Val
            260                 265                 270

Pro Thr Asn Gln Gln Glu Trp Gly Asp Trp Cys Asn Val Ser Gly Ala
        275                 280                 285

Gly Phe Gly Thr Arg Pro Thr Thr Asn Thr Gly Asn Ala Leu Ile Asp
290                 295                 300

Ala Ile Val Trp Val Lys Pro Gly Gly Glu Ser Asp Gly Thr Ser Asp
305                 310                 315                 320

Thr Ser Ala Ala Arg Tyr Asp Ala His Cys Gly Arg Asn Ser Ala Phe
                325                 330                 335

Lys Pro Ala Pro Glu Ala Gly Thr Trp Phe Gln Ala Tyr Phe Glu Met
            340                 345                 350

Leu Leu Lys Asn Ala Asn Pro Ala Leu Ala
        355                 360

<210> SEQ ID NO 25
<211> LENGTH: 351
<212> TYPE: PRT
<213> ORGANISM: Agaricus bisporus D649

<400> SEQUENCE: 25

Ala Gly Asn Pro Tyr Thr Gly Lys Thr Val Trp Leu Ser Pro Phe Tyr
1               5                   10                  15

Ala Asp Glu Val Ala Gln Ala Ala Asp Ile Ser Asn Pro Ser Leu
            20                  25                  30

Ala Thr Lys Ala Ala Ser Val Ala Lys Ile Pro Thr Phe Val Trp Phe
        35                  40                  45

Asp Thr Val Ala Lys Val Pro Asp Leu Gly Gly Tyr Leu Ala Asp Ala
    50                  55                  60

Arg Ser Lys Asn Gln Leu Val Gln Ile Val Tyr Asp Leu Pro Asp
65                  70                  75                  80

Arg Asp Cys Ala Ala Leu Ala Ser Asn Gly Glu Phe Ser Leu Ala Asn
                85                  90                  95

Asp Gly Leu Asn Lys Tyr Lys Asn Tyr Val Asp Gln Ile Ala Ala Gln
            100                 105                 110

Ile Lys Gln Phe Pro Asp Val Ser Val Ala Val Ile Glu Pro Asp
        115                 120                 125

Ser Leu Ala Asn Leu Val Thr Asn Leu Asn Val Gln Lys Cys Ala Asn
    130                 135                 140

Ala Gln Ser Ala Tyr Lys Glu Gly Val Ile Tyr Ala Val Gln Lys Leu
145                 150                 155                 160

Asn Ala Val Gly Val Thr Met Tyr Ile Asp Ala Gly His Ala Gly Trp
                165                 170                 175

Leu Gly Trp Pro Ala Asn Leu Ser Pro Ala Ala Gln Leu Phe Ala Gln
            180                 185                 190
```

```
Ile Tyr Arg Asp Ala Gly Ser Pro Arg Asn Leu Arg Gly Ile Ala Thr
        195                 200                 205

Asn Val Ala Asn Phe Asn Ala Leu Arg Ala Ser Ser Pro Asp Pro Ile
    210                 215                 220

Thr Gln Gly Asn Ser Asn Tyr Asp Glu Ile His Tyr Ile Glu Ala Leu
225                 230                 235                 240

Ala Pro Met Leu Ser Asn Ala Gly Phe Pro Ala His Phe Ile Val Asp
                245                 250                 255

Gln Gly Arg Ser Gly Val Gln Asn Ile Arg Asp Gln Trp Gly Asp Trp
            260                 265                 270

Cys Asn Val Lys Gly Ala Gly Phe Gly Gln Arg Pro Thr Thr Asn Thr
        275                 280                 285

Gly Ser Ser Leu Ile Asp Ala Ile Val Trp Val Lys Pro Gly Gly Glu
    290                 295                 300

Cys Asp Gly Thr Ser Asp Asn Ser Ser Pro Arg Phe Asp Ser His Cys
305                 310                 315                 320

Ser Leu Ser Asp Ala His Gln Pro Ala Pro Glu Ala Gly Thr Trp Phe
                325                 330                 335

Gln Ala Tyr Phe Glu Thr Leu Val Ala Asn Ala Asn Pro Ala Leu
            340                 345                 350

<210> SEQ ID NO 26
<211> LENGTH: 360
<212> TYPE: PRT
<213> ORGANISM: Polyporus arcularius 69B-8

<400> SEQUENCE: 26

Thr Pro Ala Ala Gly Asn Pro Phe Val Gly Val Thr Pro Phe Leu Ser
1               5                   10                  15

Pro Tyr Tyr Ala Ala Glu Val Ala Ala Ala Asp Ala Ile Thr Asp
            20                  25                  30

Ser Thr Leu Lys Ala Lys Ala Ala Ser Val Ala Lys Ile Pro Thr Phe
        35                  40                  45

Thr Trp Leu Asp Ser Val Ala Lys Val Pro Asp Leu Gly Thr Tyr Leu
    50                  55                  60

Ala Asp Ala Ser Ala Leu Gln Lys Ser Ser Gly Gln Pro Gln Val Val
65                  70                  75                  80

Gln Ile Val Val Tyr Asp Leu Pro Asp Arg Asp Cys Ala Ala Lys Ala
                85                  90                  95

Ser Asn Gly Glu Phe Ser Ile Ala Asp Gly Gly Gln Ala Lys Tyr Tyr
            100                 105                 110

Asp Tyr Ile Asp Gln Ile Val Ala Gln Ile Lys Lys Phe Pro Asp Val
        115                 120                 125

Arg Val Ile Ala Val Ile Glu Pro Asp Ser Leu Ala Asn Leu Val Thr
    130                 135                 140

Asn Leu Asn Val Gln Lys Cys Ala Asn Ala Gln Thr Thr Tyr Lys Ala
145                 150                 155                 160

Cys Val Thr Tyr Ala Leu Asn Gln Leu Ala Ser Val Gly Val Tyr Gln
                165                 170                 175

Tyr Met Asp Ala Gly His Ala Gly Trp Leu Gly Trp Pro Ala Asn Ile
            180                 185                 190

Gln Pro Ala Ala Gln Leu Phe Ala Asp Met Phe Lys Ser Ala Asn Ser
        195                 200                 205

Ser Lys Phe Val Arg Gly Leu Ala Thr Asn Val Ala Asn Tyr Asn Ala
    210                 215                 220
```

```
Leu Ser Ala Ala Ser Pro Asp Pro Ile Thr Gln Gly Asp Pro Asn Tyr
225                 230                 235                 240

Asp Glu Leu His Tyr Ile Asn Ala Leu Gly Pro Met Leu Ala Gln Gln
            245                 250                 255

Gly Phe Pro Ala Gln Phe Val Val Asp Gln Gly Arg Ser Gly Gln Gln
        260                 265                 270

Asn Leu Arg Gln Gln Trp Gly Asp Trp Cys Asn Ile Lys Gly Ala Gly
    275                 280                 285

Phe Gly Thr Arg Pro Thr Thr Asn Thr Gly Ser Ser Leu Ile Asp Ala
290                 295                 300

Ile Val Trp Val Lys Pro Gly Gly Glu Ser Asp Gly Thr Ser Asn Ser
305                 310                 315                 320

Ser Ser Pro Arg Phe Asp Ser Thr Cys Ser Leu Ser Asp Ala Thr Gln
                325                 330                 335

Pro Ala Pro Glu Ala Gly Thr Trp Phe Gln Thr Tyr Phe Glu Thr Leu
            340                 345                 350

Val Ser Lys Ala Asn Pro Pro Leu
        355                 360

<210> SEQ ID NO 27
<211> LENGTH: 358
<212> TYPE: PRT
<213> ORGANISM: Lentinula edodes Stamets CS-2

<400> SEQUENCE: 27

Thr Pro Ala Ala Gly Asn Pro Phe Thr Gly Tyr Glu Ile Tyr Leu Ser
1               5                   10                  15

Pro Tyr Tyr Ala Asn Glu Ile Ala Ala Ala Val Thr Gln Ile Ser Asp
            20                  25                  30

Pro Thr Thr Ala Ala Ala Ala Lys Val Ala Asn Ile Pro Thr Phe
        35                  40                  45

Ile Trp Leu Asp Gln Val Ala Lys Val Pro Asp Leu Gly Thr Tyr Leu
50                  55                  60

Ala Asp Ala Ser Ala Lys Gln Lys Ser Glu Gly Lys Asn Tyr Leu Val
65                  70                  75                  80

Gln Ile Val Val Tyr Asp Leu Pro Asp Arg Asp Cys Ala Ala Leu Ala
                85                  90                  95

Ser Asn Gly Glu Phe Thr Ile Ala Asp Asn Gly Glu Ala Asn Tyr His
            100                 105                 110

Asp Tyr Ile Asp Gln Ile Val Ala Gln Ile Lys Gln Tyr Pro Asp Val
        115                 120                 125

His Val Val Ala Val Ile Glu Pro Asp Ser Leu Ala Asn Leu Val Thr
    130                 135                 140

Asn Leu Ser Val Ala Lys Cys Ala Asn Ala Gln Thr Thr Tyr Leu Glu
145                 150                 155                 160

Cys Val Thr Tyr Ala Met Gln Gln Leu Ser Ala Val Gly Val Thr Met
                165                 170                 175

Tyr Leu Asp Ala Gly His Ala Gly Trp Leu Gly Trp Pro Ala Asn Leu
            180                 185                 190

Ser Pro Ala Ala Gln Leu Phe Thr Ser Leu Tyr Ser Asn Ala Gly Ser
        195                 200                 205

Pro Ser Gly Val Arg Gly Leu Ala Thr Asn Val Ala Asn Tyr Asn Ala
    210                 215                 220

Leu Val Ala Thr Thr Pro Asp Pro Ile Thr Gln Gly Asp Pro Asn Tyr
225                 230                 235                 240
```

```
Asp Glu Met Leu Tyr Ile Glu Ala Leu Ala Pro Leu Leu Gly Ser Phe
            245                 250                 255

Pro Ala His Phe Ile Val Asp Gln Gly Arg Ser Gly Val Gln Asp Ile
        260                 265                 270

Arg Gln Gln Trp Gly Asp Trp Cys Asn Val Leu Gly Ala Gly Phe Gly
            275                 280                 285

Thr Gln Pro Thr Thr Asn Thr Gly Ser Ser Leu Ile Asp Ser Ile Val
        290                 295                 300

Trp Val Lys Pro Gly Gly Glu Cys Asp Gly Thr Ser Asn Thr Ser Ser
305                 310                 315                 320

Pro Arg Tyr Asp Ala His Cys Gly Leu Pro Asp Ala Thr Pro Asn Ala
                325                 330                 335

Pro Glu Ala Gly Thr Trp Phe Gln Ala Tyr Phe Glu Thr Leu Val Glu
            340                 345                 350

Lys Ala Asn Pro Pro Leu
            355

<210> SEQ ID NO 28
<211> LENGTH: 357
<212> TYPE: PRT
<213> ORGANISM: Lentinula edodes L54

<400> SEQUENCE: 28

Thr Pro Ala Ala Gly Asn Pro Phe Thr Glu Gln Ile Tyr Leu Ser Pro
1               5                   10                  15

Tyr Tyr Ala Asn Glu Ile Ala Ala Val Thr Gln Ile Ser Asp Pro
            20                  25                  30

Thr Thr Ala Ala Ala Ala Lys Val Ala Asn Ile Pro Thr Phe Ile
        35                  40                  45

Trp Leu Asp Gln Val Ala Lys Val Pro Asp Leu Gly Thr Tyr Leu Ala
    50                  55                  60

Asp Ala Ser Ala Lys Gln Lys Ser Glu Gly Lys Asn Tyr Leu Val Gln
65                  70                  75                  80

Ile Val Val Tyr Asp Leu Pro Asp Arg Asp Cys Ala Ala Leu Ala Ser
                85                  90                  95

Asn Gly Glu Phe Thr Ile Ala Asp Asn Gly Glu Ala Asn Tyr His Asp
            100                 105                 110

Tyr Ile Asp Gln Ile Val Ala Gln Ile Lys Gln Tyr Pro Asp Val His
        115                 120                 125

Val Val Ala Val Ile Glu Pro Asp Ser Leu Ala Asn Leu Val Thr Asn
    130                 135                 140

Leu Ser Val Ala Lys Cys Ala Asn Ala Gln Thr Thr Tyr Leu Glu Cys
145                 150                 155                 160

Val Thr Tyr Ala Met Gln Gln Leu Ser Ala Val Gly Val Thr Met Tyr
                165                 170                 175

Leu Asp Ala Gly His Ala Gly Trp Leu Gly Trp Pro Ala Asn Leu Ser
            180                 185                 190

Pro Ala Ala Gln Leu Phe Thr Ser Leu Tyr Ser Asn Ala Gly Ser Pro
        195                 200                 205

Ser Gly Val Arg Gly Leu Ala Thr Asn Val Ala Asn Tyr Asn Ala Leu
    210                 215                 220

Val Ala Thr Thr Pro Asp Pro Ile Thr Gln Gly Asp Pro Asn Tyr Asp
225                 230                 235                 240

Glu Met Leu Tyr Ile Glu Ala Leu Ala Pro Leu Leu Gly Ser Phe Pro
                245                 250                 255
```

```
Ala His Phe Ile Val Asp Gln Gly Arg Ser Gly Val Gln Asp Ile Arg
            260                 265                 270

Gln Gln Trp Gly Asp Trp Cys Asn Val Leu Gly Ala Gly Phe Gly Thr
        275                 280                 285

Gln Pro Thr Thr Asn Thr Gly Ser Ser Leu Ile Asp Ser Ile Val Trp
    290                 295                 300

Val Lys Pro Gly Gly Glu Cys Asp Gly Thr Ser Asn Thr Ser Ser Pro
305                 310                 315                 320

Arg Tyr Asp Ala His Cys Gly Leu Pro Asp Ala Thr Pro Asn Ala Pro
                325                 330                 335

Glu Ala Gly Thr Trp Phe Gln Ala Tyr Phe Glu Thr Leu Val Glu Lys
            340                 345                 350

Ala Asn Pro Pro Leu
            355

<210> SEQ ID NO 29
<211> LENGTH: 365
<212> TYPE: PRT
<213> ORGANISM: Malbranchea cinnamomea

<400> SEQUENCE: 29

Gln Ala Asn Ser Ser Asn Pro Phe Ala Gly His Thr Ile Tyr Pro Asn
1               5                   10                  15

Pro Tyr Tyr Ser Asn Glu Ile Asp Glu Phe Ala Ile Pro Ala Leu Gln
            20                  25                  30

Glu Thr Asp Pro Ala Leu Val Glu Lys Ala Ala Leu Val Lys Glu Val
        35                  40                  45

Gly Thr Phe Phe Trp Ile Asp Val Val Ala Lys Val Pro Asp Ile Gly
    50                  55                  60

Pro Tyr Leu Gln Gly Ile Gln Glu Ala Asn Ala Ala Gly Gln Asn Pro
65                  70                  75                  80

Pro Tyr Ile Gly Ala Ile Val Val Tyr Asp Leu Pro Asn Arg Asp Cys
                85                  90                  95

Ala Ala Ala Ala Ser Asn Gly Glu Phe Ser Leu Glu Asp Gly Gly Glu
            100                 105                 110

Glu Lys Tyr Arg Gly Tyr Ile Asp Gly Ile Arg Glu Gln Ile Glu Lys
        115                 120                 125

Tyr Pro Asp Val Arg Val Ala Leu Val Ile Glu Pro Asp Ser Leu Ala
    130                 135                 140

Asn Met Val Thr Asn Leu Asn Val Pro Lys Cys Ala Glu Ser Glu Gln
145                 150                 155                 160

Ala Tyr Arg Asp Gly Val Ala Tyr Ala Leu Lys Gln Leu Asp Leu Pro
                165                 170                 175

Asn Val Trp Thr Tyr Ile Asp Ala Gly His Ser Gly Trp Leu Gly Trp
            180                 185                 190

Pro Ala Asn Ile Glu Pro Ala Ala Glu Ile Phe Val Glu Val Trp Asn
        195                 200                 205

Ala Ala Gly Arg Pro Lys Ser Thr Arg Gly Phe Ala Thr Asn Val Ser
    210                 215                 220

Asn Tyr Asn Gly Tyr Ser Leu Ser Thr Ala Pro Pro Tyr Thr Glu Pro
225                 230                 235                 240

Asn Pro Asn Phe Asp Glu Val Arg Tyr Ile Asn Ala Phe Arg Pro Leu
                245                 250                 255

Leu Glu Ala Arg Gly Phe Pro Ala Tyr Phe Ile Val Asp Gln Gly Arg
            260                 265                 270
```

Ser Gly Val Gln Pro Thr Ala Gln Ile Glu Gln Gly His Trp Cys Asn
        275                 280                 285

Val Ile Asp Thr Gly Phe Gly Thr Arg Pro Thr Thr Asp Thr Gly Asn
        290                 295                 300

Glu Tyr Val Asp Ser Ile Val Trp Val Lys Pro Gly Gly Glu Ser Asp
305                 310                 315                 320

Gly Thr Ser Asp Thr Ser Ala Glu Arg Tyr Asp Tyr His Cys Gly Leu
                325                 330                 335

Glu Asp Ala Leu Lys Pro Ala Pro Glu Ala Gly Gln Trp Phe Gln Ala
                340                 345                 350

Tyr Phe Glu Gln Leu Leu Arg Asn Ala Asn Pro Pro Phe
                355                 360                 365

<210> SEQ ID NO 30
<211> LENGTH: 440
<212> TYPE: PRT
<213> ORGANISM: Phanerochaete chrysosporium

<400> SEQUENCE: 30

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
                20                  25                  30

Ser Gln Cys Leu Pro Gly Ser Ala Val Thr Thr Ser Val Ile Thr
            35                  40                  45

Ser His Ser Ser Ser Val Ser Val Ser Ser His Ser Gly Ser Ser
        50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
            100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
        130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
            180                 185                 190

Asn Tyr Ile Asp Gln Ile Val Ala Gln Ile Gln Gln Phe Pro Asp Val
        195                 200                 205

Arg Val Val Ala Val Ile Glu Pro Asp Ser Leu Ala Asn Leu Val Thr
210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
                340                 345                 350

Asn Ile Arg Gln Gln Trp Gly Asp Trp Cys Asn Ile Lys Gly Ala Gly
                355                 360                 365

Phe Gly Thr Arg Pro Thr Thr Asn Thr Gly Ser Gln Phe Ile Asp Ser
370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
                405                 410                 415

Pro Ala Pro Glu Ala Gly Thr Trp Phe Gln Ala Tyr Phe Gln Thr Leu
                420                 425                 430

Val Ser Ala Ala Asn Pro Pro Leu
435                 440

<210> SEQ ID NO 31
<211> LENGTH: 360
<212> TYPE: PRT
<213> ORGANISM: Volvariella volvacea

<400> SEQUENCE: 31

Val Pro Ala Ala Gly Asn Pro Tyr Thr Gly Tyr Glu Ile Tyr Leu Ser
1               5                   10                  15

Pro Tyr Tyr Ala Ala Glu Ala Gln Ala Ala Ala Gln Ile Ser Asp
                20                  25                  30

Ala Thr Gln Lys Ala Lys Ala Leu Lys Val Ala Gln Ile Pro Thr Phe
                35                  40                  45

Thr Trp Phe Asp Val Ile Ala Lys Thr Ser Thr Leu Gly Asp Tyr Leu
50                  55                  60

Ala Glu Ala Ser Ala Leu Gly Lys Ser Ser Gly Lys Lys Tyr Leu Val
65                  70                  75                  80

Gln Ile Val Val Tyr Asp Leu Pro Asp Arg Asp Cys Ala Ala Leu Ala
                85                  90                  95

Ser Asn Gly Glu Phe Ser Ile Ala Asn Asn Gly Leu Asn Asn Tyr Lys
                100                 105                 110

Gly Tyr Ile Asp Gln Leu Val Ala Gln Ile Lys Lys Tyr Pro Asp Val
                115                 120                 125

Arg Val Val Ala Val Ile Glu Pro Asp Ser Leu Ala Asn Leu Val Thr
130                 135                 140

Asn Leu Asn Val Ser Lys Cys Ala Asn Ala Gln Thr Ala Tyr Lys Ala
145                 150                 155                 160

Gly Val Thr Tyr Ala Leu Gln Gln Leu Asn Ser Val Gly Val Tyr Met
                165                 170                 175

Tyr Leu Asp Ala Gly His Ala Gly Trp Leu Gly Trp Pro Ala Asn Leu
                180                 185                 190

Asn Pro Ala Ala Gln Leu Phe Ser Gln Leu Tyr Arg Asp Ala Gly Ser
                195                 200                 205

Pro Gln Tyr Val Arg Gly Leu Ala Thr Asn Val Ala Asn Tyr Asn Ala
                210                 215                 220

```
Leu Ser Ala Ser Ser Pro Asp Pro Val Thr Gln Gly Asn Pro Asn Tyr
225                 230                 235                 240

Asp Glu Leu His Tyr Ile Asn Ala Leu Ala Pro Ala Leu Gln Ser Gly
            245                 250                 255

Gly Phe Pro Ala His Phe Ile Val Asp Gln Gly Arg Ser Gly Val Gln
        260                 265                 270

Asn Ile Arg Gln Gln Trp Gly Asp Trp Cys Asn Val Lys Gly Ala Gly
    275                 280                 285

Phe Gly Gln Arg Pro Thr Leu Ser Thr Gly Ser Ser Leu Ile Asp Ala
290                 295                 300

Ile Val Trp Ile Lys Pro Gly Gly Glu Cys Asp Gly Thr Thr Asn Thr
305                 310                 315                 320

Ser Ser Pro Arg Tyr Asp Ser His Cys Gly Leu Ser Asp Ala Thr Pro
            325                 330                 335

Asn Ala Pro Glu Ala Gly Gln Trp Phe Gln Ala Tyr Phe Glu Thr Leu
        340                 345                 350

Val Arg Asn Ala Ser Pro Pro Leu
    355                 360

<210> SEQ ID NO 32
<211> LENGTH: 356
<212> TYPE: PRT
<213> ORGANISM: Chrysosporium lucknowense

<400> SEQUENCE: 32

Leu Asp Ala Ser Thr Asn Val Phe Gln Gln Tyr Thr Leu His Pro Asn
1               5                   10                  15

Asn Phe Tyr Arg Ala Glu Val Glu Ala Ala Ala Glu Ala Ile Ser Asp
            20                  25                  30

Ser Ala Leu Ala Glu Lys Ala Arg Lys Val Ala Asp Val Gly Thr Phe
        35                  40                  45

Leu Trp Leu Asp Thr Ile Glu Asn Ile Gly Arg Leu Glu Pro Ala Leu
50                  55                  60

Glu Asp Val Pro Cys Glu Asn Ile Val Gly Leu Val Ile Tyr Asp Leu
65                  70                  75                  80

Pro Gly Arg Asp Cys Ala Ala Lys Ala Ser Asn Gly Glu Leu Lys Val
            85                  90                  95

Gly Glu Leu Asp Arg Tyr Lys Thr Glu Tyr Ile Asp Lys Ile Ala Glu
        100                 105                 110

Ile Leu Lys Ala His Ser Asn Thr Ala Phe Ala Leu Val Ile Glu Pro
    115                 120                 125

Asp Ser Leu Pro Asn Leu Val Thr Asn Ser Asp Leu Gln Thr Cys Gln
130                 135                 140

Gln Ser Ala Ser Gly Tyr Arg Glu Gly Val Ala Tyr Ala Leu Lys Gln
145                 150                 155                 160

Leu Asn Leu Pro Asn Val Val Met Tyr Ile Asp Ala Gly His Gly Gly
            165                 170                 175

Trp Leu Gly Trp Asp Ala Asn Leu Lys Pro Gly Ala Gln Glu Leu Ala
        180                 185                 190

Ser Val Tyr Lys Ser Ala Gly Ser Pro Ser Gln Val Arg Gly Ile Ser
    195                 200                 205

Thr Asn Val Ala Gly Trp Asn Ala Trp Asp Gln Glu Pro Gly Glu Phe
210                 215                 220

Ser Asp Ala Ser Asp Ala Gln Tyr Asn Lys Cys Gln Asn Glu Lys Ile
225                 230                 235                 240
```

```
Tyr Ile Asn Thr Phe Gly Ala Glu Leu Lys Ser Ala Gly Met Pro Asn
                245                 250                 255

His Ala Ile Ile Asp Thr Gly Arg Asn Gly Val Thr Gly Leu Arg Asp
            260                 265                 270

Glu Trp Gly Asp Trp Cys Asn Val Asn Gly Ala Gly Phe Gly Val Arg
        275                 280                 285

Pro Thr Ala Asn Thr Gly Asp Glu Leu Ala Asp Ala Phe Val Trp Val
    290                 295                 300

Lys Pro Gly Gly Glu Ser Asp Gly Thr Ser Asp Ser Ser Ala Ala Arg
305                 310                 315                 320

Tyr Asp Ser Phe Cys Gly Lys Pro Asp Ala Phe Lys Pro Ser Pro Glu
                325                 330                 335

Ala Gly Thr Trp Asn Gln Ala Tyr Phe Glu Met Leu Leu Lys Asn Ala
            340                 345                 350

Asn Pro Ser Phe
        355

<210> SEQ ID NO 33
<211> LENGTH: 409
<212> TYPE: PRT
<213> ORGANISM: Pleurotus sajor-caju

<400> SEQUENCE: 33

Thr Pro Asp Ala Gly Asn Pro Tyr Ile Gly Tyr Asp Val Ser His Val
1               5                   10                  15

Leu Trp Cys Gln Ile Tyr Leu Ser Pro Tyr Tyr Ala Asp Glu Val Ala
            20                  25                  30

Ala Ala Val Ser Ala Ile Ser Asn Pro Ala Leu Ala Ala Lys Ala Ala
        35                  40                  45

Ser Val Ala Asn Ile Pro Thr Phe Ile Trp Phe Asp Val Val Ala Lys
    50                  55                  60

Val Pro Thr Leu Gly Thr Tyr Leu Ala Asp Ala Leu Ser Ile Gln Gln
65                  70                  75                  80

Ser Thr Gly Arg Asn Gln Leu Val Gln Ile Val Val Tyr Asp Leu Pro
                85                  90                  95

Asp Arg Asp Cys Ala Ala Leu Ala Ser Asn Gly Glu Phe Ser Ile Ala
            100                 105                 110

Asn Asn Gly Leu Ala Asn Tyr Lys Asn Tyr Val Asp Gln Ile Val Ala
        115                 120                 125

Gln Ile Ala Arg Thr Cys Cys Pro Leu Val Thr Ser Ala Ile Thr Asp
    130                 135                 140

Leu Ala Cys Leu Ser Glu Tyr Pro Gln Ile Arg Val Val Ala Val Val
145                 150                 155                 160

Glu Pro Asp Ser Leu Ala Asn Met Val Thr Asn Leu Asn Val Pro Lys
                165                 170                 175

Cys Ala Gly Ala Gln Ala Ala Tyr Thr Glu Gly Val Thr Tyr Ala Leu
            180                 185                 190

Gln Lys Leu Asn Thr Val Gly Val Tyr Ser Tyr Val Asp Ala Gly His
        195                 200                 205

Ala Gly Trp Leu Gly Trp Pro Ala Asn Leu Gly Pro Ala Ala Gln Leu
    210                 215                 220

Phe Ala Asn Leu Tyr Thr Asn Ala Gly Ser Pro Ser Phe Phe Arg Gly
225                 230                 235                 240

Leu Ala Thr Asn Val Ala Asn Tyr Asn Leu Leu Asn Ala Pro Ser Pro
                245                 250                 255
```

```
Asp Pro Val Thr Ser Pro Asn Ala Asn Tyr Asp Glu Ile His Tyr Ile
            260                 265                 270

Asn Val Ser Asp Cys Phe Val Leu Ile Trp Thr Ser Leu Thr Ile Cys
            275                 280                 285

Ile Ile Ala Leu Ala Pro Glu Leu Ser Ser Arg Gly Phe Pro Ala His
290                 295                 300

Phe Ile Val Asp Gln Gly Arg Ser Ala Val Gln Gly Ile Arg Gly Ala
305                 310                 315                 320

Trp Gly Asp Trp Cys Asn Val Asp Asn Ala Gly Phe Gly Thr Arg Pro
                325                 330                 335

Thr Thr Ser Thr Gly Ser Ser Leu Ile Asp Ala Ile Val Trp Val Lys
            340                 345                 350

Pro Gly Gly Glu Ser Asp Gly Thr Ser Asp Thr Ser Ala Val Arg Tyr
            355                 360                 365

Asp Gly His Cys Gly Leu Ala Ser Ala Lys Lys Pro Ala Pro Glu Ala
            370                 375                 380

Met Ala Ser Val Tyr Ser His Ser Ser Phe Gln Ala Tyr Phe Glu Met
385                 390                 395                 400

Leu Val Ala Asn Ala Val Pro Ala Leu
                405

<210> SEQ ID NO 34
<211> LENGTH: 359
<212> TYPE: PRT
<213> ORGANISM: Trametes versicolor

<400> SEQUENCE: 34

Thr Pro Ala Ala Gly Asn Pro Phe Thr Gly Phe Gln Val Tyr Leu Ser
1               5                   10                  15

Pro Tyr Tyr Ser Ala Glu Ile Ala Ser Ala Ala Ala Val Thr Asp
            20                  25                  30

Ser Ser Leu Lys Ala Lys Ala Ala Ser Val Ala Asn Ile Pro Thr Phe
        35                  40                  45

Thr Trp Leu Asp Ser Val Ala Lys Val Pro Asp Leu Gly Thr Tyr Leu
    50                  55                  60

Ala Asp Ala Ser Ser Ile Gln Thr Lys Thr Gly Gln Lys Gln Leu Val
65                  70                  75                  80

Pro Ile Val Val Tyr Glu Leu Pro Asp Arg Asp Cys Ala Ala Lys Ala
                85                  90                  95

Ser Asn Gly Glu Phe Ser Ile Ala Asp Ala Gly Ala Glu Asn Tyr Lys
            100                 105                 110

Asp Tyr Ile Asp Gln Ile Val Pro Gln Ile Lys Gln Phe Pro Asp Val
        115                 120                 125

Arg Val Val Ala Val Ile Glu Pro Asp Ser Leu Ala Asn Leu Val Thr
    130                 135                 140

Asn Leu Asn Val Gln Lys Cys Ala Asn Gly Gly Thr Tyr Lys Ala Ser
145                 150                 155                 160

Val Thr Tyr Ala Leu Gln Gln Leu Ser Ser Val Gly Val Thr Met Tyr
                165                 170                 175

Met Asp Ala Gly His Ala Gly Trp Leu Gly Trp Pro Ala Asn Ile Gln
            180                 185                 190

Pro Gly Ser Glu Val Phe Ala Glu Met Phe Lys Ser Ala Asp Phe Val
        195                 200                 205

Ala Phe Val Arg Ala Phe Ala Thr Asn Val Arg Glu Tyr Asn Ala Leu
    210                 215                 220
```

```
Thr Ala Ala Phe Pro Arg Pro Ile Thr Gln Gly Asn Pro Asn Tyr Asp
225                 230                 235                 240

Glu Phe Pro Tyr Ile Gln Arg Val Arg Pro Met Leu Lys Ser Pro Gly
                245                 250                 255

Phe Pro Ala Gln Phe Val Val Asp Gln Gly Arg Ala Gly Gln Gln Asn
            260                 265                 270

Phe Arg Gln Gln Trp Gly Asp Trp Cys Asn Ile Lys Gly Ala Gly Phe
        275                 280                 285

Gly Thr Arg Pro Thr Thr Ser Thr Gly Asn Pro Leu Ile Asp Ala Ile
    290                 295                 300

Ile Trp Val Lys Pro Gly Gly Glu Ser Asp Gly Thr Ser Asn Ser Ser
305                 310                 315                 320

Ser Pro Arg Tyr Asp Ser Thr Leu Leu Ser Val Arg Arg Asp Asp Pro
                325                 330                 335

Ala Pro Glu Ala Gly Thr Trp Phe Gln Ala Tyr Phe Glu Thr Leu Val
            340                 345                 350

Ser Lys Pro Thr Arg Pro Leu
            355

<210> SEQ ID NO 35
<211> LENGTH: 356
<212> TYPE: PRT
<213> ORGANISM: Neurospora crassa OR74A

<400> SEQUENCE: 35

Leu Asp Ala Ser Thr Asn Val Trp Lys Lys Tyr Thr Leu His Ala Asn
1               5                   10                  15

Lys Phe Tyr Arg Thr Glu Val Glu Ala Ala Val Ala Ala Ile Ser Asp
                20                  25                  30

Ser Ser Leu Ala Ala Lys Ala Ala Lys Val Ala Asn Val Gly Ser Phe
            35                  40                  45

Leu Trp Leu Asp Ser Ile Glu Asn Ile Gly Lys Leu Glu Pro Ala Leu
    50                  55                  60

Glu Asp Val Pro Cys Asp His Ile Leu Gly Leu Val Ile Tyr Asp Leu
65                  70                  75                  80

Pro Gly Arg Asp Cys Ala Ala Lys Ala Ser Asn Gly Glu Leu Ala Val
                85                  90                  95

Gly Glu Leu Ser Arg Tyr Lys Thr Glu Tyr Ile Asp Ala Ile Val Lys
            100                 105                 110

Ile Leu Lys Ala His Pro Lys Thr Ala Phe Ala Leu Val Ile Glu Pro
        115                 120                 125

Asp Ser Leu Pro Asn Leu Val Thr Asn Ser Asp Leu Gln Thr Cys Lys
    130                 135                 140

Asp Ser Ala Ser Gly Tyr Arg Asp Gly Val Ala Tyr Ala Leu Arg Asn
145                 150                 155                 160

Leu Asn Leu Pro Asn Val Val Met Tyr Ile Asp Ala Gly His Gly Gly
                165                 170                 175

Trp Leu Gly Trp Asp Ala Asn Leu Lys Pro Gly Ala Gln Glu Leu Ala
            180                 185                 190

Lys Ala Tyr Lys Ala Ala Gly Ser Pro Lys Gln Val Arg Gly Ile Ala
        195                 200                 205

Thr Asn Val Ala Gly Trp Asn Gln Trp Asp Leu Thr Pro Gly Glu Phe
    210                 215                 220

Ser Lys Ala Ser Asp Ala Lys Tyr Asn Lys Cys Gln Asn Glu Lys Leu
225                 230                 235                 240
```

```
Tyr Leu Asp Asn Phe Gly Pro Ala Leu Lys Ser Ala Gly Met Pro Asn
            245                 250                 255

His Ala Ile Val Asp Thr Gly Arg Asn Gly Val Ser Gly Leu Arg Gln
            260                 265                 270

Glu Trp Gly Asn Trp Cys Asn Val Asn Gly Ala Gly Phe Gly Val Arg
            275                 280                 285

Pro Thr Ser Ser Thr Gly His Asp Leu Ala Asp Ala Phe Val Trp Val
            290                 295                 300

Lys Pro Gly Gly Glu Ser Asp Gly Thr Ser Asp Ser Ser Ala Thr Arg
305                 310                 315                 320

Tyr Asp Ser Phe Cys Gly Lys Ser Asp Ala Tyr Gln Pro Ser Pro Glu
            325                 330                 335

Ala Gly Ser Trp Asn Gln Asp Tyr Phe Glu Met Leu Val Lys Asn Ala
            340                 345                 350

Lys Pro Ser Phe
            355

<210> SEQ ID NO 36
<211> LENGTH: 356
<212> TYPE: PRT
<213> ORGANISM: Magnaporthe grisea 70-15

<400> SEQUENCE: 36

Leu Asp Ala Ser Thr Asn Val Phe Ser Lys Tyr Thr Leu His Pro Asn
1               5                   10                  15

Ser Phe Tyr Arg Ala Glu Val Glu Ala Ala Glu Ala Ile Ser Asp
            20                  25                  30

Ser Thr Leu Lys Ala Gln Ala Leu Lys Val Ala Asp Val Gly Ser Phe
            35                  40                  45

Leu Trp Ile Asp Thr Ile Ser Ala Ile Ser Arg Ile Glu Pro Gly Val
        50                  55                  60

Ser Asp Gln Pro Cys Asp His Ile Leu Gly Leu Val Ile Tyr Asp Leu
65                  70                  75                  80

Pro Gly Arg Asp Cys Ala Ala Lys Ala Ser Asn Gly Glu Leu Lys Val
            85                  90                  95

Gly Glu Leu Ala Lys Tyr Lys Ser Gln Tyr Ile Asp Pro Ile Ala Ala
            100                 105                 110

Leu Leu Lys Lys Tyr Asn Asn His Ala Phe Ala Leu Leu Ile Glu Pro
            115                 120                 125

Asp Ser Leu Pro Asn Leu Val Thr Asn Ser Asp Leu Ser Ala Cys Gln
130                 135                 140

Gln Ser Ala Ala Gly Tyr Arg Asp Gly Val Ala Tyr Ala Leu Lys Thr
145                 150                 155                 160

Leu Asn Leu Pro Asn Val Val Met Tyr Ile Asp Ala Gly His Gly Gly
            165                 170                 175

Trp Leu Gly Trp Asn Asp Asn Leu Lys Pro Gly Ala Glu Glu Leu Ala
            180                 185                 190

Lys Ala Tyr Lys Ala Ala Gly Ser Pro Lys Gln Phe Arg Gly Phe Ala
            195                 200                 205

Thr Asn Val Ala Gly Trp Asn Ala Trp Asp Leu Thr Pro Gly Glu Phe
            210                 215                 220

Ser Ser Ala Ser Asp Ala Gln Trp Asn Lys Cys Gln Asn Glu Lys Ile
225                 230                 235                 240

Tyr Val Glu Thr Phe Gly Pro Leu Leu Lys Asn Ala Gly Met Pro Asn
            245                 250                 255
```

-continued

His Ala Ile Val Asp Val Gly Arg Asn Ala Val Gln Gly Leu Arg Glu
            260                 265                 270

Glu Trp Gly His Trp Cys Asn Val Asn Gly Ala Gly Phe Gly Val Arg
        275                 280                 285

Pro Thr Thr Ser Thr Gly Ser Ser Leu Thr Asp Ala Leu Leu Trp Val
    290                 295                 300

Lys Pro Gly Gly Glu Ser Asp Gly Thr Ser Asp Thr Ser Ala Thr Arg
305                 310                 315                 320

Tyr Asp Ser Phe Cys Gly Met Ser Asp Ala Tyr Lys Pro Ser Pro Glu
                325                 330                 335

Ala Gly Gln Trp Asn Gln Asp Tyr Phe Glu Met Leu Leu Arg Asn Ala
            340                 345                 350

Lys Pro Gln Phe
        355

<210> SEQ ID NO 37
<211> LENGTH: 447
<212> TYPE: PRT
<213> ORGANISM: Trichoderma reesei

<400> SEQUENCE: 37

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

```
Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Ala Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 38
<211> LENGTH: 447
<212> TYPE: PRT
<213> ORGANISM: Trichoderma reesei

<400> SEQUENCE: 38

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Ala Val Ala
            115                 120                 125

Lys Val Pro Ser Phe Met Trp Leu Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205
```

```
Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Cys Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 39
<211> LENGTH: 447
<212> TYPE: PRT
<213> ORGANISM: Trichoderma reesei

<400> SEQUENCE: 39

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140
```

```
Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
            165                 170                 175

Ala Ala Leu Ala Ser Asn Gly Glu Tyr Ser Ile Ala Asp Gly Gly Val
        180                 185                 190

Ala Lys Tyr Lys Asn Tyr Ile Asp Thr Ile Arg Gln Ile Val Val Glu
    195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
        260                 265                 270

Pro Ala Asn Gln Asp Pro Ala Ala Gln Leu Phe Ala Asn Val Tyr Lys
    275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
        340                 345                 350

Arg Ser Gly Lys Gln Pro Thr Gly Gln Gln Trp Gly Asp Gly Cys
    355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
        420                 425                 430

Ala Tyr Phe Val Gln Leu Leu Thr Asn Ala Asn Pro Ser Phe Leu
    435                 440                 445

<210> SEQ ID NO 40
<211> LENGTH: 447
<212> TYPE: PRT
<213> ORGANISM: Trichoderma reesei

<400> SEQUENCE: 40

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80
```

```
Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Asn Cys
            355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 41
<211> LENGTH: 447
<212> TYPE: PRT
<213> ORGANISM: Trichoderma reesei

<400> SEQUENCE: 41

Gln Ala Cys Ser Ser Val Trp Gly Gln Cys Gly Gly Gln Asn Trp Ser
1               5                   10                  15
```

Gly Pro Thr Cys Cys Ala Ser Gly Ser Thr Cys Val Tyr Ser Asn Asp
             20              25              30

Tyr Tyr Ser Gln Cys Leu Pro Gly Ala Ala Ser Ser Ser Ser Ser Thr
         35              40              45

Arg Ala Ala Ser Thr Thr Ser Arg Val Ser Pro Thr Thr Ser Arg Ser
     50              55              60

Ser Ser Ala Thr Pro Pro Pro Gly Ser Thr Thr Thr Arg Val Pro Pro
65              70              75              80

Val Gly Ser Gly Thr Ala Thr Tyr Ser Gly Asn Pro Phe Val Gly Val
             85              90              95

Thr Pro Trp Ala Asn Ala Tyr Tyr Ala Ser Glu Val Ser Ser Leu Ala
             100             105             110

Ile Pro Ser Leu Thr Gly Ala Met Ala Thr Ala Ala Ala Val Ala
             115             120             125

Lys Val Pro Ser Phe Met Trp Leu Asp Thr Leu Asp Lys Thr Pro Leu
     130             135             140

Met Glu Gln Thr Leu Ala Asp Ile Arg Thr Ala Asn Lys Asn Gly Gly
145             150             155             160

Asn Tyr Ala Gly Gln Phe Val Val Tyr Asp Leu Pro Asp Arg Asp Cys
             165             170             175

Ala Ala Leu Ala Ser Asn Gly Glu Tyr Ser Ile Ala Asp Gly Gly Val
             180             185             190

Ala Lys Tyr Lys Asn Tyr Ile Asp Thr Ile Arg Gln Ile Val Val Glu
         195             200             205

Tyr Ser Asp Ile Arg Thr Leu Leu Val Ile Glu Pro Asp Ser Leu Ala
     210             215             220

Asn Leu Val Thr Asn Leu Gly Thr Pro Lys Cys Ala Asn Ala Gln Ser
225             230             235             240

Ala Tyr Leu Glu Cys Ile Asn Tyr Ala Val Thr Gln Leu Asn Leu Pro
             245             250             255

Asn Val Ala Met Tyr Leu Asp Ala Gly His Ala Gly Trp Leu Gly Trp
             260             265             270

Pro Ala Asn Gln Asp Pro Ala Ala Gln Leu Phe Ala Asn Val Tyr Lys
             275             280             285

Asn Ala Ser Ser Pro Arg Ala Leu Arg Gly Leu Ala Thr Asn Val Ala
290             295             300

Asn Tyr Asn Gly Trp Asn Ile Thr Ser Pro Pro Ser Tyr Thr Gln Gly
305             310             315             320

Asn Ala Val Tyr Asn Glu Lys Leu Tyr Ile His Ala Ile Gly Pro Leu
             325             330             335

Leu Ala Asn His Gly Trp Ser Asn Ala Phe Phe Ile Thr Asp Gln Gly
             340             345             350

Arg Ser Gly Lys Gln Pro Thr Gly Gln Gln Gln Trp Gly Asp Arg Cys
             355             360             365

Asn Val Ile Gly Thr Gly Phe Gly Ile Arg Pro Ser Ala Asn Thr Gly
     370             375             380

Asp Ser Leu Leu Asp Ser Phe Val Trp Val Lys Pro Gly Gly Glu Cys
385             390             395             400

Asp Gly Thr Ser Asp Ser Ser Ala Pro Arg Phe Asp Pro His Cys Ala
             405             410             415

Leu Pro Asp Ala Leu Gln Pro Ala Pro Gln Ala Gly Ala Trp Phe Gln
             420             425             430

Ala Tyr Phe Val Gln Leu Leu Thr Asn Ala Asn Pro Ser Phe Leu 435        440        445

<210> SEQ ID NO 42
<211> LENGTH: 447
<212> TYPE: PRT
<213> ORGANISM: Trichoderma reesei

<400> SEQUENCE: 42

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Ser Cys
        355                 360                 365

Asn Val Ile Gly Thr Gly Phe Gly Ile Arg Pro Ser Ala Asn Thr Gly

```
            370                 375                 380
Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 43
<211> LENGTH: 447
<212> TYPE: PRT
<213> ORGANISM: Trichoderma reesei

<400> SEQUENCE: 43

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
```

```
              305                 310                 315                 320

Asn Ala Val Tyr Asn Glu Lys Leu Tyr Ile His Ala Ile Gly Pro Leu
                    325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Thr Cys
                355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 44
<211> LENGTH: 447
<212> TYPE: PRT
<213> ORGANISM: Trichoderma reesei

<400> SEQUENCE: 44

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
                180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
```

```
                        245                 250                 255
Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Val Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 45
<211> LENGTH: 453
<212> TYPE: PRT
<213> ORGANISM: Humicola insolens

<400> SEQUENCE: 45

Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
        35                  40                  45

Thr Ser Thr Ser Ser Ser Thr Thr Ser Arg Ala Thr Ser Thr Thr
    50                  55                  60

Arg Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ala Ser Asn Gly Glu
```

```
                    180             185                 190
Trp Ala Ile Ala Asn Asn Gly Ala Asn Asn Tyr Lys Gly Tyr Ile Asn
            195                 200             205
Arg Ile Arg Glu Ile Leu Ile Ser Phe Ser Asp Val Arg Thr Ile Leu
        210                 215             220
Val Ile Glu Pro Asp Ser Leu Ala Asn Met Val Thr Asn Met Asn Val
225                 230             235                 240
Ala Lys Cys Ser Gly Ala Ala Ser Thr Tyr Arg Glu Leu Thr Ile Tyr
            245                 250             255
Ala Leu Lys Gln Leu Asp Leu Pro His Val Ala Met Tyr Met Asp Ala
        260                 265             270
Gly His Ala Gly Trp Leu Gly Trp Pro Ala Asn Ile Gln Pro Ala Ala
        275                 280             285
Glu Leu Phe Ala Lys Ile Tyr Glu Asp Ala Gly Lys Pro Arg Ala Val
        290                 295             300
Arg Gly Leu Ala Thr Asn Val Ala Asn Tyr Asn Ala Trp Ser Ile Ser
305                 310             315                 320
Ser Pro Pro Pro Tyr Thr Ser Pro Asn Pro Asn Tyr Asp Glu Lys His
                325             330                 335
Tyr Ile Glu Ala Phe Arg Pro Leu Leu Glu Ala Arg Gly Phe Pro Ala
            340             345                 350
Gln Phe Ile Val Asp Gln Gly Arg Ser Gly Lys Gln Pro Thr Gly Gln
        355                 360             365
Lys Glu Trp Gly His Gly Cys Asn Ala Ile Gly Thr Gly Phe Gly Met
        370                 375             380
Arg Pro Thr Ala Asn Thr Gly His Gln Tyr Val Asp Ala Phe Val Trp
385                 390             395                 400
Val Lys Pro Gly Gly Glu Cys Asp Gly Thr Ser Asp Thr Thr Ala Ala
            405                 410             415
Arg Tyr Asp Tyr His Cys Gly Leu Glu Asp Ala Leu Lys Pro Ala Pro
            420                 425             430
Glu Ala Gly Gln Trp Phe Gln Ala Tyr Phe Glu Gln Leu Leu Arg Asn
        435                 440             445
Ala Asn Pro Pro Phe
    450

<210> SEQ ID NO 46
<211> LENGTH: 440
<212> TYPE: PRT
<213> ORGANISM: Phanerochaete chrysosporium

<400> SEQUENCE: 46

Ala Ser Ser Glu Trp Gly Gln Cys Gly Gly Ile Gly Trp Thr Gly Pro
1               5                   10                  15
Thr Thr Cys Val Ser Gly Thr Thr Cys Thr Val Leu Asn Pro Tyr Tyr
            20                  25                  30
Ser Gln Cys Leu Pro Gly Ser Ala Val Thr Thr Ser Val Ile Thr
            35                  40                  45
Ser His Ser Ser Ser Val Ser Ser Val Ser Ser His Ser Gly Ser Ser
        50                  55                  60
Thr Ser Thr Ser Ser Pro Thr Gly Pro Thr Gly Thr Asn Pro Pro Pro
65                  70                  75                  80
Pro Pro Ser Ala Asn Asn Pro Trp Thr Gly Phe Gln Ile Phe Leu Ser
                85                  90                  95
Pro Tyr Tyr Ala Asn Glu Val Ala Ala Ala Lys Gln Ile Thr Asp
```

```
            100                 105                 110
Pro Thr Leu Ser Ser Lys Ala Ala Ser Val Ala Asn Ile Pro Thr Phe
        115                 120                 125
Thr Trp Leu Asp Ser Val Ala Lys Ile Pro Asp Leu Gly Thr Tyr Leu
    130                 135                 140
Ala Ser Ala Ser Ala Leu Gly Lys Ser Thr Gly Thr Lys Gln Leu Val
145                 150                 155                 160
Gln Ile Val Ile Tyr Asp Leu Pro Asp Arg Asp Cys Ala Ala Lys Ala
            165                 170                 175
Ser Asn Gly Glu Phe Ser Ile Ala Asn Asn Gly Gln Ala Asn Tyr Glu
            180                 185                 190
Asn Tyr Ile Asp Gln Ile Val Ala Gln Ile Gln Gln Phe Pro Asp Val
            195                 200                 205
Arg Val Val Ala Val Ile Glu Pro Asp Ser Leu Ala Asn Leu Val Thr
        210                 215                 220
Asn Leu Asn Val Gln Lys Cys Ala Asn Ala Lys Thr Thr Tyr Leu Ala
225                 230                 235                 240
Cys Val Asn Tyr Ala Leu Thr Asn Leu Ala Lys Val Gly Val Tyr Met
            245                 250                 255
Tyr Met Asp Ala Gly His Ala Gly Trp Leu Gly Trp Pro Ala Asn Leu
            260                 265                 270
Ser Pro Ala Ala Gln Leu Phe Thr Gln Val Trp Gln Asn Ala Gly Lys
        275                 280                 285
Ser Pro Phe Ile Lys Gly Leu Ala Thr Asn Val Ala Asn Tyr Asn Ala
        290                 295                 300
Leu Gln Ala Ala Ser Pro Asp Pro Ile Thr Gln Gly Asn Pro Asn Tyr
305                 310                 315                 320
Asp Glu Ile His Tyr Ile Asn Ala Leu Ala Pro Leu Leu Gln Gln Ala
            325                 330                 335
Gly Trp Asp Ala Thr Phe Ile Val Asp Gln Gly Arg Ser Gly Val Gln
            340                 345                 350
Asn Ile Arg Gln Gln Trp Gly Asp Gly Cys Asn Ile Lys Gly Ala Gly
        355                 360                 365
Phe Gly Thr Arg Pro Thr Thr Asn Thr Gly Ser Gln Phe Ile Asp Ser
    370                 375                 380
Ile Val Trp Val Lys Pro Gly Gly Glu Cys Asp Gly Thr Ser Asn Ser
385                 390                 395                 400
Ser Ser Pro Arg Tyr Asp Ser Thr Cys Ser Leu Pro Asp Ala Ala Gln
            405                 410                 415
Pro Ala Pro Glu Ala Gly Thr Trp Phe Gln Ala Tyr Phe Gln Thr Leu
            420                 425                 430
Val Ser Ala Ala Asn Pro Pro Leu
        435                 440

<210> SEQ ID NO 47
<211> LENGTH: 30
<212> TYPE: DNA
<213> ORGANISM: Artificial
<220> FEATURE:
<223> OTHER INFORMATION: Primer sequence

<400> SEQUENCE: 47
accaaaagat ctatgagatt tccttcaatt                                    30

<210> SEQ ID NO 48
<211> LENGTH: 30
```

-continued

```
<212> TYPE: DNA
<213> ORGANISM: Artificial
<220> FEATURE:
<223> OTHER INFORMATION: Primer sequence

<400> SEQUENCE: 48
tgagcagcta gccctttat ccaaagatac                                    30

<210> SEQ ID NO 49
<211> LENGTH: 30
<212> TYPE: DNA
<213> ORGANISM: Artificial
<220> FEATURE:
<223> OTHER INFORMATION: Primer sequence

<400> SEQUENCE: 49
aaaagggcta gctgctcaag cgtctggggc                                   30

<210> SEQ ID NO 50
<211> LENGTH: 36
<212> TYPE: DNA
<213> ORGANISM: Artificial
<220> FEATURE:
<223> OTHER INFORMATION: Primer sequence

<400> SEQUENCE: 50
gagctcagat ctggtacctt acaggaacga tgggtt                            36

<210> SEQ ID NO 51
<211> LENGTH: 39
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (19)..(20)
<223> OTHER INFORMATION: n is a, c, g, or t

<400> SEQUENCE: 51
cagcaacagt ggggagacnn stgcaatgtg atcggcacc                         39

<210> SEQ ID NO 52
<211> LENGTH: 21
<212> TYPE: DNA
<213> ORGANISM: Artificial
<220> FEATURE:
<223> OTHER INFORMATION: Primer sequence

<400> SEQUENCE: 52
agcacaaata acgggttatt g                                            21

<210> SEQ ID NO 53
<211> LENGTH: 23
<212> TYPE: DNA
<213> ORGANISM: Artificial
<220> FEATURE:
<223> OTHER INFORMATION: Primer sequence

<400> SEQUENCE: 53
gcaacacctg gcaattcctt acc                                          23

<210> SEQ ID NO 54
<211> LENGTH: 22
<212> TYPE: DNA
<213> ORGANISM: Artificial
<220> FEATURE:
<223> OTHER INFORMATION: Primer sequence
```

<400> SEQUENCE: 54
ctagctgatc actgaggtac cg                                              22

<210> SEQ ID NO 55
<211> LENGTH: 22
<212> TYPE: DNA
<213> ORGANISM: Artificial
<220> FEATURE:
<223> OTHER INFORMATION: Primer sequence

<400> SEQUENCE: 55
aattcggtac ctcagtgatc ag                                              22

<210> SEQ ID NO 56
<211> LENGTH: 40
<212> TYPE: DNA
<213> ORGANISM: Artificial
<220> FEATURE:
<223> OTHER INFORMATION: Primer sequence

<400> SEQUENCE: 56
ggtatctttg gataaaaggg ctagctcgga gtggggacag                           40

<210> SEQ ID NO 57
<211> LENGTH: 35
<212> TYPE: DNA
<213> ORGANISM: Artificial
<220> FEATURE:
<223> OTHER INFORMATION: Primer sequence

<400> SEQUENCE: 57
ggagatcgaa ttcggtacct acagcggcgg gttgg                                35

<210> SEQ ID NO 58
<211> LENGTH: 27
<212> TYPE: DNA
<213> ORGANISM: Artificial
<220> FEATURE:
<223> OTHER INFORMATION: Primer sequence

<400> SEQUENCE: 58
cagtggggag acgggtgcaa catcaag                                         27

<210> SEQ ID NO 59
<211> LENGTH: 22
<212> TYPE: DNA
<213> ORGANISM: Artificial
<220> FEATURE:
<223> OTHER INFORMATION: Primer sequence

<400> SEQUENCE: 59
gtctccccac tgttggcgga tg                                              22

<210> SEQ ID NO 60
<211> LENGTH: 19
<212> TYPE: DNA
<213> ORGANISM: Artificial
<220> FEATURE:
<223> OTHER INFORMATION: Primer sequence

<400> SEQUENCE: 60
gccagcattg ctgctaaag                                                  19

<210> SEQ ID NO 61
<211> LENGTH: 54

```
<212> TYPE: DNA
<213> ORGANISM: Artificial
<220> FEATURE:
<223> OTHER INFORMATION: Primer sequence

<400> SEQUENCE: 61
aaggatgacg atgacaagga attcctcgag gctagctgtg ccccgacttg gggc        54

<210> SEQ ID NO 62
<211> LENGTH: 54
<212> TYPE: DNA
<213> ORGANISM: Artificial
<220> FEATURE:
<223> OTHER INFORMATION: Primer sequence

<400> SEQUENCE: 62
agcggccgct taccgcgggt cgacgggccc ggtacctcag aacggcggat tggc        54

<210> SEQ ID NO 63
<211> LENGTH: 29
<212> TYPE: DNA
<213> ORGANISM: Artificial
<220> FEATURE:
<223> OTHER INFORMATION: Primer sequence

<400> SEQUENCE: 63
gaatggggcc acgggtgcaa tgccattgg                                   29

<210> SEQ ID NO 64
<211> LENGTH: 22
<212> TYPE: DNA
<213> ORGANISM: Artificial
<220> FEATURE:
<223> OTHER INFORMATION: Primer sequence

<400> SEQUENCE: 64
gtggccccat tccttctggc cg                                          22

<210> SEQ ID NO 65
<211> LENGTH: 22
<212> TYPE: DNA
<213> ORGANISM: Artificial
<220> FEATURE:
<223> OTHER INFORMATION: Primer sequence

<400> SEQUENCE: 65
cgaggcaagg gcagcgcaat cg                                          22

<210> SEQ ID NO 66
<211> LENGTH: 25
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (12)..(13)
<223> OTHER INFORMATION: n is a, c, g, or t

<400> SEQUENCE: 66
cccttgcctc gnnsggcgaa tactc                                       25

<210> SEQ ID NO 67
<211> LENGTH: 26
<212> TYPE: DNA
<213> ORGANISM: Artificial
<220> FEATURE:
<223> OTHER INFORMATION: Primer sequence
```

```
<400> SEQUENCE: 67
gccgcctggc ttgacccaga caaacg                                    26

<210> SEQ ID NO 68
<211> LENGTH: 25
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (11)..(12)
<223> OTHER INFORMATION: n is a, c, g, or t

<400> SEQUENCE: 68
gccaggcggc nnstgtgacg gcacc                                     25

<210> SEQ ID NO 69
<211> LENGTH: 24
<212> TYPE: DNA
<213> ORGANISM: Artificial
<220> FEATURE:
<223> OTHER INFORMATION: Primer sequence

<400> SEQUENCE: 69
ctcgccgcct ggcttgaccc agac                                      24

<210> SEQ ID NO 70
<211> LENGTH: 25
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (12)..(13)
<223> OTHER INFORMATION: n is a, c, g, or t

<400> SEQUENCE: 70
caggcggcga gnnsgacggc accag                                     25

<210> SEQ ID NO 71
<211> LENGTH: 26
<212> TYPE: DNA
<213> ORGANISM: Artificial
<220> FEATURE:
<223> OTHER INFORMATION: Primer sequence

<400> SEQUENCE: 71
gaggcgccgg ttgcaaggca tctggg                                    26

<210> SEQ ID NO 72
<211> LENGTH: 28
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (13)..(14)
<223> OTHER INFORMATION: n is a, c, g, or t

<400> SEQUENCE: 72
ccggcgcctc aannsggtgc ttggttcc                                  28

<210> SEQ ID NO 73
<211> LENGTH: 21
```

```
<212> TYPE: DNA
<213> ORGANISM: Artificial
<220> FEATURE:
<223> OTHER INFORMATION: Primer sequence

<400> SEQUENCE: 73
cgagatcttc gagggcgtaa c                                              21

<210> SEQ ID NO 74
<211> LENGTH: 24
<212> TYPE: DNA
<213> ORGANISM: Artificial
<220> FEATURE:
<223> OTHER INFORMATION: Primer sequence

<400> SEQUENCE: 74
gctcacccgg gaagaccaca tggc                                           24

<210> SEQ ID NO 75
<211> LENGTH: 24
<212> TYPE: DNA
<213> ORGANISM: Artificial
<220> FEATURE:
<223> OTHER INFORMATION: Primer sequence

<400> SEQUENCE: 75
ccgtatagta tcgcatgcaa ttgc                                           24

<210> SEQ ID NO 76
<211> LENGTH: 33
<212> TYPE: DNA
<213> ORGANISM: Artificial
<220> FEATURE:
<223> OTHER INFORMATION: Primer sequence

<400> SEQUENCE: 76
gccgacaacc atggtgcaat acacagaggg tga                                 33

<210> SEQ ID NO 77
<211> LENGTH: 33
<212> TYPE: DNA
<213> ORGANISM: Artificial
<220> FEATURE:
<223> OTHER INFORMATION: Primer sequence

<400> SEQUENCE: 77
catcaccatg gtctccttca cctccctcct cgc                                 33

<210> SEQ ID NO 78
<211> LENGTH: 33
<212> TYPE: DNA
<213> ORGANISM: Artificial
<220> FEATURE:
<223> OTHER INFORMATION: Primer sequence

<400> SEQUENCE: 78
cttgagcagc tagcctggcg cttctccaca gcc                                 33

<210> SEQ ID NO 79
<211> LENGTH: 21
<212> TYPE: DNA
<213> ORGANISM: Artificial
<220> FEATURE:
<223> OTHER INFORMATION: Primer sequence

<400> SEQUENCE: 79
cctggtgacc aacctcggta c                                              21
```

-continued

<210> SEQ ID NO 80
<211> LENGTH: 22
<212> TYPE: DNA
<213> ORGANISM: Artificial
<220> FEATURE:
<223> OTHER INFORMATION: Primer sequence

<400> SEQUENCE: 80
gtggggagac gggtgcaatg tg                                              22

<210> SEQ ID NO 81
<211> LENGTH: 22
<212> TYPE: DNA
<213> ORGANISM: Artificial
<220> FEATURE:
<223> OTHER INFORMATION: Primer sequence

<400> SEQUENCE: 81
cacattgcac ccgtctcccc ac                                              22

<210> SEQ ID NO 82
<211> LENGTH: 20
<212> TYPE: DNA
<213> ORGANISM: Artificial
<220> FEATURE:
<223> OTHER INFORMATION: Primer sequence

<400> SEQUENCE: 82
cctctgggcc cccagataag                                                 20

<210> SEQ ID NO 83
<211> LENGTH: 447
<212> TYPE: PRT
<213> ORGANISM: Trichoderma reesei

<400> SEQUENCE: 83

```
Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Ser Gly Glu Tyr Ser Ile Ala Asp Gly Gly Val
            180                 185                 190
```

```
Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
        260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
        340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
        420                 425                 430

Ala Tyr Phe Val Gln Leu Leu Thr Asn Ala Asn Pro Ser Phe Leu
        435                 440                 445

<210> SEQ ID NO 84
<211> LENGTH: 447
<212> TYPE: PRT
<213> ORGANISM: Trichoderma reesei

<400> SEQUENCE: 84

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125
```

```
Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Arg Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Glu Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 85
<211> LENGTH: 447
<212> TYPE: PRT
<213> ORGANISM: Trichoderma reesei

<400> SEQUENCE: 85

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60
```

Ser Ser Ala Thr Pro Pro Gly Ser Thr Thr Arg Val Pro Pro
65                  70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Gly Gly Glu Tyr Ser Ile Ala Asp Gly Gly Val
            180                 185                 190

Ala Lys Tyr Lys Asn Tyr Ile Asp Thr Ile Arg Gln Ile Val Val Glu
    195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 86
<211> LENGTH: 447
<212> TYPE: PRT
<213> ORGANISM: Trichoderma reesei

<400> SEQUENCE: 86

```
Ala Ser Cys Ser Ser Val Trp Gly Gln Cys Gly Gly Gln Asn Trp Ser
  1               5                  10                  15

Gly Pro Thr Cys Cys Ala Ser Gly Ser Thr Cys Val Tyr Ser Asn Asp
             20                  25                  30

Tyr Tyr Ser Gln Cys Leu Pro Gly Ala Ser Ser Ser Ser Ser Ser Thr
             35                  40                  45

Arg Ala Ala Ser Thr Thr Ser Arg Val Ser Pro Thr Thr Ser Arg Ser
 50                  55                  60

Ser Ser Ala Thr Pro Pro Gly Ser Thr Thr Thr Arg Val Pro Pro
 65                  70                  75                  80

Val Gly Ser Gly Thr Ala Thr Tyr Ser Gly Asn Pro Phe Val Gly Val
                 85                  90                  95

Thr Pro Trp Ala Asn Ala Tyr Tyr Ala Ser Glu Val Ser Ser Leu Ala
             100                 105                 110

Ile Pro Ser Leu Thr Gly Ala Met Ala Thr Ala Ala Ala Val Ala
             115                 120                 125

Lys Val Pro Ser Phe Met Trp Leu Asp Thr Leu Asp Lys Thr Pro Leu
 130                 135                 140

Met Glu Gln Thr Leu Ala Asp Ile Arg Thr Ala Asn Lys Asn Gly Gly
 145                 150                 155                 160

Asn Tyr Ala Gly Gln Phe Val Val Tyr Asp Leu Pro Asp Arg Asp Cys
                 165                 170                 175

Ala Ala Leu Ala Ser Ala Gly Glu Tyr Ser Ile Ala Asp Gly Gly Val
             180                 185                 190

Ala Lys Tyr Lys Asn Tyr Ile Asp Thr Ile Arg Gln Ile Val Val Glu
             195                 200                 205

Tyr Ser Asp Ile Arg Thr Leu Leu Val Ile Glu Pro Asp Ser Leu Ala
 210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
             245                 250                 255

Asn Val Ala Met Tyr Leu Asp Ala Gly His Ala Gly Trp Leu Gly Trp
             260                 265                 270

Pro Ala Asn Gln Asp Pro Ala Ala Gln Leu Phe Ala Asn Val Tyr Lys
             275                 280                 285

Asn Ala Ser Ser Pro Arg Ala Leu Arg Gly Leu Ala Thr Asn Val Ala
 290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
             325                 330                 335

Leu Ala Asn His Gly Trp Ser Asn Ala Phe Phe Ile Thr Asp Gln Gly
             340                 345                 350

Arg Ser Gly Lys Gln Pro Thr Gly Gln Gln Gln Trp Gly Asp Trp Cys
             355                 360                 365

Asn Val Ile Gly Thr Gly Phe Gly Ile Arg Pro Ser Ala Asn Thr Gly
             370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
             405                 410                 415

Leu Pro Asp Ala Leu Gln Pro Ala Pro Gln Ala Gly Ala Trp Phe Gln
```

```
                    420                 425                 430
Ala Tyr Phe Val Gln Leu Leu Thr Asn Ala Asn Pro Ser Phe Leu
            435                 440                 445
```

<210> SEQ ID NO 87
<211> LENGTH: 447
<212> TYPE: PRT
<213> ORGANISM: Trichoderma reesei

<400> SEQUENCE: 87

```
Ala Ser Cys Ser Ser Val Trp Gly Gln Cys Gly Gly Gln Asn Trp Ser
1               5                   10                  15

Gly Pro Thr Cys Cys Ala Ser Gly Gly Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Ser Thr Ser Arg Ser
50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
```

```
                355                 360                 365
Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly His Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 88
<211> LENGTH: 447
<212> TYPE: PRT
<213> ORGANISM: Trichoderma reesei

<400> SEQUENCE: 88

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Ala Val Ala
            115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
```

```
                290                 295                 300
Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Trp Gly Asp Trp Cys
                355                 360                 365

Asn Val Ile Gly Thr Gly Phe Gly Ile Arg Pro Ser Ala Asn Thr Gly
                370                 375                 380

Asp Ser Leu Leu Asp Ser Phe Val Trp Val Lys Pro Gly Gly Thr Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
                435                 440                 445

<210> SEQ ID NO 89
<211> LENGTH: 447
<212> TYPE: PRT
<213> ORGANISM: Trichoderma reesei

<400> SEQUENCE: 89

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
                35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Ala Val Ala
                115                 120                 125

Lys Val Pro Ser Phe Met Trp Leu Asp Thr Leu Asp Lys Thr Pro Leu
                130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
                210                 215                 220

Asn Leu Val Thr Asn Leu Gly Thr Pro Lys Cys Ala Asn Ala Gln Ser
```

```
                225                 230                 235                 240
Ala Tyr Leu Glu Cys Ile Asn Tyr Ala Val Thr Gln Leu Asn Leu Pro
                    245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Trp Gly Asp Trp Cys
            355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Ser Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
            435                 440                 445

<210> SEQ ID NO 90
<211> LENGTH: 447
<212> TYPE: PRT
<213> ORGANISM: Trichoderma reesei

<400> SEQUENCE: 90

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
        130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
```

```
                    165                 170                 175
Ala Ala Leu Ala Ser Asn Gly Glu Tyr Ser Ile Ala Asp Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
        260                 265                 270

Pro Ala Asn Gln Asp Pro Ala Ala Gln Leu Phe Ala Asn Val Tyr Lys
    275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
        340                 345                 350

Arg Ser Gly Lys Gln Pro Thr Gly Gln Gln Trp Gly Asp Trp Cys
    355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Val
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Gln Ala Gly Ala Trp Phe Gln
        420                 425                 430

Ala Tyr Phe Val Gln Leu Leu Thr Asn Ala Asn Pro Ser Phe Leu
    435                 440                 445

<210> SEQ ID NO 91
<211> LENGTH: 447
<212> TYPE: PRT
<213> ORGANISM: Trichoderma reesei

<400> SEQUENCE: 91

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
```

```
            100                 105                 110
Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Met
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 92
<211> LENGTH: 447
<212> TYPE: PRT
<213> ORGANISM: Trichoderma reesei

<400> SEQUENCE: 92

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
```

```
                35                  40                  45
Arg Ala Ala Ser Thr Thr Ser Arg Val Ser Pro Thr Thr Ser Arg Ser
 50                  55                  60

Ser Ser Ala Thr Pro Pro Gly Ser Thr Thr Arg Val Pro Pro
 65                  70                  75                  80

Val Gly Ser Gly Thr Ala Thr Tyr Ser Gly Asn Pro Phe Val Gly Val
                 85                  90                  95

Thr Pro Trp Ala Asn Ala Tyr Tyr Ala Ser Glu Val Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Thr
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 93
<211> LENGTH: 447
```

```
<212> TYPE: PRT
<213> ORGANISM: Trichoderma reesei

<400> SEQUENCE: 93
```

| | | | | | | | | | | | | | | |
|---|---|---|---|---|---|---|---|---|---|---|---|---|---|---|

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Gly Ser Thr Thr Thr Arg Val Pro Pro
65              70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
            165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
            210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Ser
385                 390                 395                 400

```
Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 94
<211> LENGTH: 447
<212> TYPE: PRT
<213> ORGANISM: Trichoderma reesei

<400> SEQUENCE: 94

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335
```

```
Leu Ala Asn His Gly Trp Ser Asn Ala Phe Phe Ile Thr Asp Gln Gly
            340                 345                 350

Arg Ser Gly Lys Gln Pro Thr Gly Gln Gln Trp Gly Asp Trp Cys
        355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Val Gly Ala Trp Phe Gln
            420                 425                 430

Ala Tyr Phe Val Gln Leu Leu Thr Asn Ala Asn Pro Ser Phe Leu
        435                 440                 445
```

<210> SEQ ID NO 95
<211> LENGTH: 447
<212> TYPE: PRT
<213> ORGANISM: Trichoderma reesei

<400> SEQUENCE: 95

```
Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270
```

```
Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Leu Gly Ala Trp Phe Gln
                420                 425                 430

Ala Tyr Phe Val Gln Leu Leu Thr Asn Ala Asn Pro Ser Phe Leu
            435                 440                 445

<210> SEQ ID NO 96
<211> LENGTH: 447
<212> TYPE: PRT
<213> ORGANISM: Trichoderma reesei

<400> SEQUENCE: 96

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
            130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205
```

-continued

```
Tyr Ser Asp Ile Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ser Gly Ala Trp Phe Gln
            420                 425                 430

Ala Tyr Phe Val Gln Leu Leu Thr Asn Ala Asn Pro Ser Phe Leu
            435                 440                 445
```